US008067557B2

(12) United States Patent
Choi

(10) Patent No.: US 8,067,557 B2
(45) Date of Patent: Nov. 29, 2011

(54) OCL-2A3 COMPOSITIONS AND USES THEREOF

(75) Inventor: Yongwon Choi, Bryn Mawr, PA (US)

(73) Assignee: The Trustees of The University of Pennsylvania, Philadelphia, PA (US)

( * ) Notice: Subject to any disclaimer, the term of this patent is extended or adjusted under 35 U.S.C. 154(b) by 0 days.

(21) Appl. No.: 11/520,030

(22) Filed: Sep. 13, 2006

(65) Prior Publication Data

US 2007/0071741 A1  Mar. 29, 2007

Related U.S. Application Data

(63) Continuation-in-part of application No. 10/368,087, filed on Feb. 14, 2003, now Pat. No. 7,160,994.

(60) Provisional application No. 60/368,638, filed on Mar. 28, 2002.

(51) Int. Cl.
*C07H 21/04* (2006.01)
*C12N 1/20* (2006.01)
*C12N 15/85* (2006.01)

(52) U.S. Cl. ............ 536/23.1; 435/252.1; 435/325

(58) Field of Classification Search .............. None
See application file for complete search history.

(56) References Cited

U.S. PATENT DOCUMENTS 4,946,778 A  8/1990  Ladner et al.

FOREIGN PATENT DOCUMENTS

| EP | 1 087 230 AI | 3/2001 |
|---|---|---|
| JP | 2001122798 | 8/2001 |
| WO | WO 88/00205 | 1/1988 |
| WO | WO 00/13024 | 3/2000 |

OTHER PUBLICATIONS

Abe, E., Mocharla, H., Yamate, T., Taguchi, Y. & Manolagas, S. C. Meltrin-alpha, a fusion protein involved in multinucleated giant cell and osteoclast formation. Calcif Tissue Int 64, 508-515 (1999).
Centrella et al., "Transforming Growth Factor (3 Is a Bifunctional Regulator of Replication and Collagen Synthesis in Osteoblast-enriched Cell Cultures from Fetal Rat Bone", J. Biol. Chem. 1987 262 (6) :2869-2874.
Chen, E. H. & Olson, E. N. Unveiling the mechanisms of cell-cell fusion. Science 308, 369-373 (2005).
Chenu et al., "Transforming growth factor (3 inhibits formation of osteoclast-like cells in long-term human marrow cultures", Proc. Natl. Acad. Sci. USA 1988 85:5683-5687.
Choi, S. J., Han, J. H. & Roodman, G. D. ADAM8: a novel osteoclast stimulating factor. J Bone Miner Res 16, 814-822 (2001).
Hsu et al., "Tumor necrosis factor receptor family member RANK mediates osteoclast differentiation and activation induced by osfceoprotegerin ligand", Proc. Natl. Acad. Sci. USA 1999 96:3540-3545.
Hunt et al., "Cellular mechanisms of bone resorption in breast carcinoma", British Journal of Cancer 2001 35 (1).
Isgaard et al., "Effects of local administration of GH and IGF-1 on longitudinal bone growth in rats", Am. J. Physiol. 250 (Endocrinol. Metab. 13):E367-E372 1986.
Jacquin, C., Gran, D. E., Lee, S. K, Lorenzo, J. A & Aguila, H. L Identification of multiple osteoclast precursor populations in murine bone marrow. J Bone Miner Res 21, 67-77 (2006).
Joyce et al., "Transforming Growth Factor-(3 and the Initiation of Chondrogenesis and Osteogenesis in the Rat Femur", J. Cell Biology 1990 110:2195-2207.
Kadono, Y. et al. Strength of TRAF6 signalling determines osteoclastogenesis. EMBO Rep 6, 171-176 (2005).
Kiebzak et al., "Bone Status of Senescent Female Rats:Chemical, Morphometric, and Biomechanical Analyses", J. Bone and Mineral Research 1988 3(4):439-446.
Kim et al., "A Novel Member of the Leukocyte Receptor Complex Regulates Osteoclast ifferentiation1", J. Exp, Med. 2002 195:201-209.
Kohler and Milstein, "Continuous cultures of fused cells secreting antibody of predefined specificity", Nature 1975 256:495-497.
Kontani, K, Moskowitz, I. P. & Rothman, J. H. Repression of cell-cell fusion by components of the C. elegans vacuolar ATPase complex. Dev Cell 8, 787-794 (2005).
Kozbor and Roder, "The production of monoclonal antibodies from human lymphocytes", Immunology Today 1983 4 (3) :72-79.
Lee, S. K et al. Interleukin-7 influences osteoclast function in vivo but is not a critical factor in ovariectomy-induced bone loss. J Bone Miner Res 21, 695-702 (2006).
Li, Y. P., Chen, W., Liang, Y., Li, E. & Stashenko, P. Atp6i-deficient mice exhibit severe osteopetrosis due to loss of osteoclast-mediated extracellular acidification. Nat Genet 23, 447-451 (1999).
Mohler, W. A. et al. The type I membrane protein EFF-1 is essential for developmental cell fusion. Dev Cell 2, 355-362 (2002).
Montero, A. et al. Disruption of the fibroblast growth factor-2 gene results in decreased bone mass and bone formation. J Clin Invest 105, 1085-1093 (2000).
Nishi, T. & Forgac, M. The vacuolar (H+)-ATPases—nature's most versatile proton pumps. Nat Rev Mol Cell Biol 3, 94-103 (2002).
Nishi, T., Kawasaki-Nishi, S. & Forgac, M. Expression and function of the mouse V-ATPase d subunit isoforms. J Biol Chem 278, 46396-46402 (2003).
Noda and Camilliere, "In Vivo Stimulation of Bone Formation by Transforming Growth Factor-f5", Endocrinology 1989 124:2991-2294.
Rho, J. et al. Gene expression profiling of osteoclast differentiation by combined suppression subtractive hybridization (SSH) and cDNA microarray analysis. DNA Cell Biol 21, 541-549 (2002).
Rho, J., Gong, S., Kim, N. & Choi, Y. TDAG51 is not essential for Fas/CD95 regulation and apoptosis in vivo. Mol Cell Biol 21, 8365-8370 (2001).
Slovik et al., "Restoration of Spinal Bone in Osteoporotic Men by Treatment with Human Parathyroid Hormone (1-34) and 1,25-Dihydroxyvitamin D", J. Bone & Min. Res. 1986 1:377-381.
Smith, A. N., Borthwick, K. J. & Keret, F. E. Molecular cloning and characterization of novel tissue-specific isoforms of the human vacuolar H(+)-ATPase C, G and d subunits, and their evaluation in autosomal recessive distal renal tubular acidosis. Gene 297, 169-177 (2002).

(Continued)

*Primary Examiner* — Anand Desai
(74) *Attorney, Agent, or Firm* — Pearl Cohen Zedek Latzer, LLP; Mark S. Cohen

(57) ABSTRACT

This invention relates to osteoclast-specific genes and proteins. Specifically, the invention relates to OCL-2A3 or Atp6v0d2, the gene encoding it and uses thereof in methods and treatment of bone disorders.

8 Claims, 17 Drawing Sheets

OTHER PUBLICATIONS

Stevens, T. H. & Forgac, M. Structure, function and regulation of the vacuolar (H+)-ATPase Annu Rev Cell Dev Biol 13, 779-808 (1997).

Suda, T., Jimi, E., Nakamura, I. & Takahashi, N. Role of 1a,25-dihydroxyvitamin D3 in osteoclast differentiation and function. Methods Enzymol. 282, 223-235 (1997).

Sun-Wada, G. H., Yoshimizu, T., Imai-Senga, Y., Wada, Y. & Futai, M. Diversity of mouse proton-translocating ATPase: presence of multiple isoforms of the C, d and G subunits. Gene 302, 147-153 (2003).

Takami, M., Woo, J. T. & Nagai, K. Osteoblastic cells induce fusion and activation of osteoclasts through a mechanism independent of macrophage-colony-stimulating factor production. Cell Tissue Res 298, 327-334 (1999).

Teitelbaum, S. L. Bone resorption by osteoclasts. Science 289, 1504-1508 (2000).

Verrier, S., Hogan, A., McKie, N. & Horton, M. ADAM gene expression and regulation during human osteoclast formation. Bone 35, 34-46 (2004).

Walsh, M. C. et al. Osteoimmunology: Interplay Between the Immune System and Bone Metabolism. Annu Rev Immunol 24, 33-63 (2005).

Yagi, M. et al. DC-STAMP is essential for cell-cell fusion in osteoclasts and foreign body giant cells. J Exp Med 202, 345-351 (2005).

a b

OCL-2A3 COMPOSITIONS AND USES THEREOF

CROSS REFERENCE TO RELATED APPLICATIONS

This application is a Continuation-in-part Application of U.S. patent application Ser. No. 10/368,087, filed 14 Feb. 2003 now U.S. Pat. No. 7,160,994, which claims priority form U.S. Provisional Patent Application No. 60/368,638, filed 28 Mar. 2002 now expired, both which are hereby to incorporated by reference in their entirety.

FIELD OF INVENTION

Provided herein, are osteoclast-specific genes and proteins. Specifically, the invention relates to OCL-2A3, the gene encoding it and uses thereof in methods for treatment of bone diorders.

BACKGROUND OF THE INVENTION

Bone is dynamic tissue that is remodeled constantly throughout life. Living bone tissue is replenished by the processes of resorption and deposition of bone matrix and minerals. This temporally and spatially coupled process, termed bone remodeling, is accomplished largely by two cell populations, the osteoclasts and osteoblasts. The remodeling process is initiated when osteoclasts are recruited from the bone marrow or the circulation to the bone surface. The matrix and minerals of the bone are subsequently replaced by osteoblasts recruited to the resorbed bone surface from the bone marrow. Resorption of bone is carried out mainly by osteoclasts, which are multinucleated cells that are formed by fusion of hematopoietic stem cells related to the mononuclear phagocyte series. Resorption of bone takes place in scalloped spaces where the osteoclasts are attached to components of the bone matrix. Osteoclasts have been linked to many diseases, including: marble disease, osteoporosis, fracture or trauma, bone metastasis, cancer, osteosarcoma, hypercalcemia and rheumatoid arthritis.

Increased osteoclast numbers and bone resorption are found in breast cancer metastasis (Hunt, et al. (2001) Br. J. Cancer (Scotland), 85(1):78-84). Methods for identifying a compound useful for the treatment of bone disorders caused by osteoclast differentiation are described in EP 1087230. Osteoclast differentiation inhibitors, such as notch ligand polypeptides, useful to treat bone disorders are disclosed in JP2001122798. TGF-beta has also been shown to stimulate proliferation and matrix synthesis of osteoblastic cells (Centrella, et al. (1987) J. Biol. Chem. 262:2869-2874), to inhibit the formation and activity of osteoclastic cells (Chenu, et al. (1988) Proc. Natl. Acad. Sci. U.S.A. 85:683-5687; Kiebzak, et al. (1988) J. Bone Min. Res. 3:439-446), and to stimulate local bone formation in vivo (Joyce, et al. (1990) J. Cell. Biol. 110:2195-2207; Noda and Camilliere (1989) Endocrinology 124:2991-2294). Other factors reported to stimulate bone growth include bone morphogenetic proteins (WO 88/00205), insulin-like growth factor (IGF) (Isgaard, et al. (1986) Am. J. Physiol. 250:E367-72), and parathyroid hormone (Slovik, et al. (1986) J. Bone & Min. Res. 1:377-381).

Methods for diagnosing skeletal disorders such as osteoporosis and osteoarthritis using a specific marker comprising IL-1 alpha, IL-1 beta, IL-6 and its receptor are described in WO 00/13024.

Since it is highly desirable to be able to establish a predictive assay whereby the predisposition of individuals to a skeletal disorder such as osteoarthritis or osteoporosis; and can give an indication of the probability of an individual progressing to a severe case, which could enable individuals to take steps to delay onset of disease and/or targeting of individuals for treatment, it is desirable to identify Osteoclast-specific genes and proteins that are useful in detecting and isolating osteoclasts including agents which modulate osteoclast function, which can then be used in the assays and treatment of skeletal disorders.

SUMMARY OF THE INVENTION

In one embodiment, the invention provides an isolated mammalian osteoclast-specific nucleic acid sequence comprising SEQ ID NO:1, SEQ ID NO:2, SEQ ID NO:3 or SEQ ID NO:4, including variants and fragments thereof.

In another embodiment, provided herein is a method for detecting OCL-2A3 osteoclast specific expressing cells in a mixed cells population, comprising: identifying cells expressing SEQ ID NO.s 1-4 or 5-6, including variants, fragments and mutants, thereof whereby expression of said sequences indicate a OCL-2A3 osteoclast cell.

In one embodiment, provided herein is a method for identifying a modulator of a cell expressing OCL-2A3 function comprising: contacting the cell with a candidate agent; and analyzing said agent for its ability to modulate the expression of SEQ ID NO.s 1-4, genes regulated by the expression of SEQ ID NO.'s 1-4, or activity of a polypeptide encoded thereby, whereby an ability of the candidate agent to down-regulate or upregulate the expression of SEQ ID NO.s 1-4, genes regulated by the expression of SEQ ID NO.'s 1-4, or its encoded polypeptides indicate the agent is a modulator.

In one embodiment, provided herein, is a method of increasing bone mass in a subject, comprising the step of administering to said subject an agent able to inhibit the expression or function of a gene encoding OCL-2A3 in the subject, thereby inhibiting bone resorption, increasing bone formation or a combination thereof.

In another embodiment, provided herein is a method of inhibiting bone resorption in a subject, comprising administering to said subject and agent capable of inhibiting the expression or function of a gene encoding OCL-2A3, thereby inhibiting cell-to-cell fusion or osteoclast maturation.

In one embodiment, provided herein is a method of treating a pathology associated with defects in bone metabolism, remodeling or both in a subject, comprising administering to said subject an effective amount of a composition comprising an agent able to inhibit the expression or function of a gene encoding OCL-2A3 in the subject, thereby inhibiting bone resorption, increasing bone formation or a combination thereof.

In another embodiment, provided herein is a method of inhibiting osteoclast cell fusion, comprising the step of contacting the osteoclast cell with an agent able to inhibit the expression or function of a gene encoding OCL-2A3 in the subject, thereby downregulating the expression of ADAM protein's mRNA.

In one embodiment, provided herein is a transgenic mouse and progeny thereof whose genome comprises a nucleic acid which does not encode murine OCL-2A3.

In another embodiment, provided herein is a method for identifying in vivo a biological activity of a compound, said method comprising the steps of: providing a transgenic mouse whose genome comprises a nucleic acid which does not encode murine OCL-2A3; administering said compound to said mouse; determining an expressed pathology of said mouse; and identifying a in vivo biological activity of said compound.

In one embodiment, provided herein is a transgenic mouse and progeny thereof whose genome comprises a nucleic acid which encodes murine, or human OCL-2A3.

In another embodiment, provided herein is a method for identifying in-vivo a biological activity of a compound, said method comprising the steps of: providing a transgenic mouse whose genome comprises a nucleic acid which encodes murine or human OCL-2A3; administering said compound to said mouse; determining an expressed pathology of said mouse; and identifying a in-vivo biological activity of said compound.

In one embodiment, provided herein is a method of enhancing bone formation a subject, comprising the step of inhibiting OCL-2A3 expression or function in said subject, thereby increasing osteoblast numbers, enhancing anabolic activity of osteoblasts, increasing new bone formation, or combination thereof.

BRIEF DESCRIPTION OF THE DRAWINGS

FIG. 12 shows real-time PCR of RNA from wild-type and Atp6v0d2$^{-/-}$ osteoclasts. BMs isolated from wild-type and Atp6v0d2$^{-/-}$ mice were induced to become osteoclasts by treatment with M-CSF and TRANCE. RNA was collected at the indicated times after stimulation and was subjected to real-time PCR for analysis of expression of putative fusion and adhesion molecules.

DETAILED DESCRIPTION OF THE INVENTION

Figure 1:
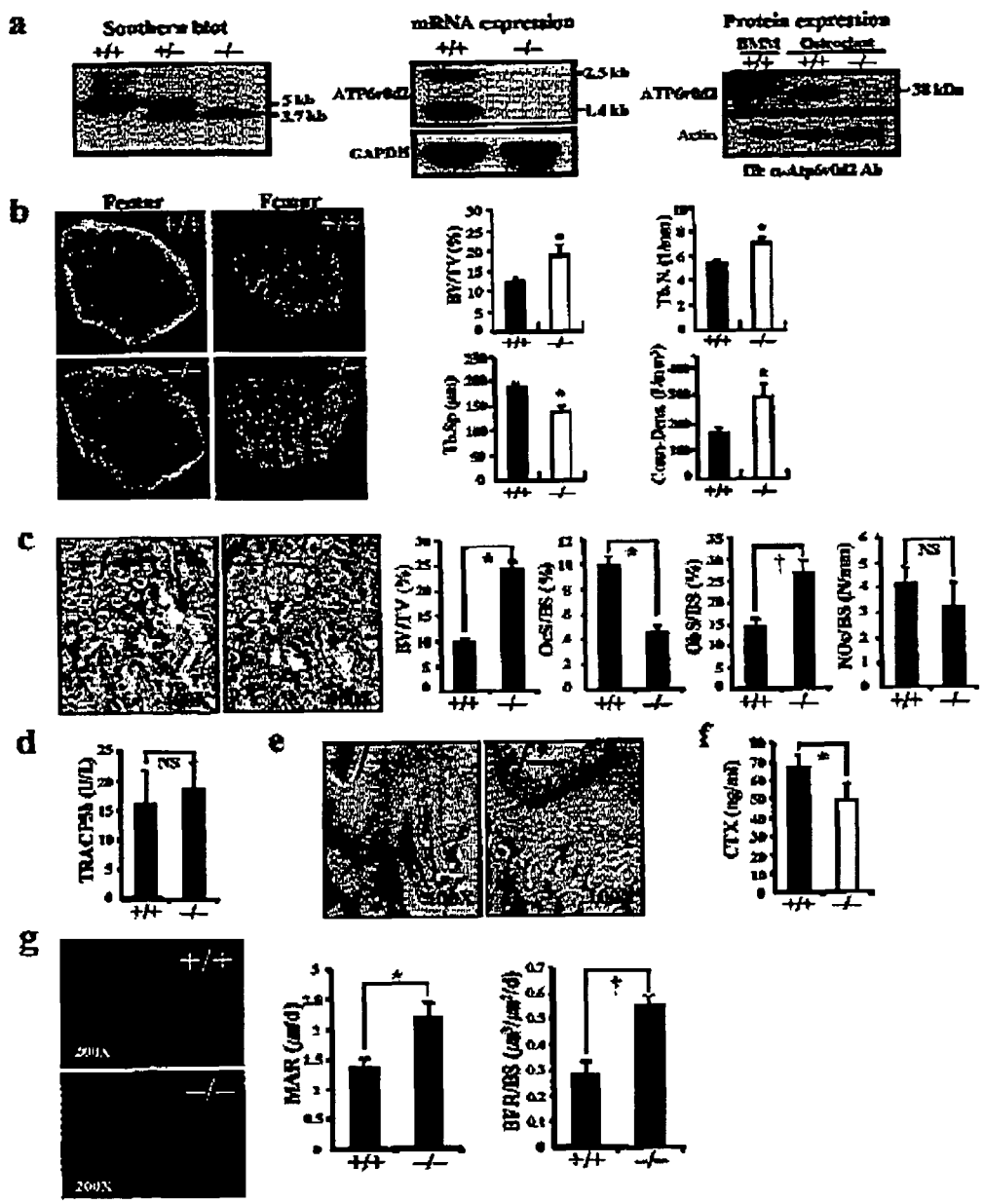
FIG. 1. shows that deletion of Atp6v0d2 leads to defective osteoclasts and increased bone formation. (a) Confirmation of Atp6v0d2 deletion by Southern blot (left). Genomic DNA from Atp6v0d2$^{+/+}$, Atp6v0d2$^{+/-}$ and Atp6v0d2$^{-/-}$ mice was isolated, digested with SphI, and probed with "Probe 1". Wild-type and null alleles show ~5 kb and 3.7 kb, respectively. Atp6v0d2 RNA expression in osteoclasts (middle). Atp6v0d2 protein expression (right). Whole cell extracts from wild-type osteoclast precursors (BMM) and wild-type (+/+) or Atp6v0d2$^{-/-}$ osteoclasts were examined with rabbit anti-Atp6v0d2 polyclonal Ab by western analysis. (b) Tibias, femurs and vertebra from 8 to 10-week-old control, wild-type (+/+) and Atp6v0d2$^{-/-}$ mice were examined by µCT. (left) Two or (right) three dimensional reconstruction of bones revealed increased bone mass in Atp6v0d2$^{-/-}$ compared with control littermates. Three-dimensional trabecular structural parameters in the secondary spongiosa of the distal femur; bone volume fraction (BV/TV), trabecular number (Tb.N), trabecular spacing (Tb.Sp), trabecular connectivity density (Conn-Dens). *$P<0.05$. Data are expressed as mean±s.e.m., n=6-8. (c) Static histomorphometry analysis of femurs from 6-7 week old Atp6v0d2$^{-/-}$ mice and control littermates (+/+): bone volume (BV/TV), osteoclast surface per bone surface (OcS/BS), osteoblast surface per bone surface (ObS/BS), osteoclast number per bone surface (NOc/BS). *$P<0.005$, †$P<0.05$, NS: not significant. Data are expressed as mean±s.e.m., n=4. (d) Serum TRAP5b were measured by ELISA. NS, not significant (e) Alcian blue staining on femurs from 6-7 week old Atp6v0d2$^{-/-}$ mice and control littermates (+/+). (f) Serum carboxy-terminal collagen crosslinks (CTX) measure by ELISA. *$P<0.05$ (g) Dynamic histomorphometry analysis of femurs from 6-7 week old Atp6v0d2$^{-/-}$ mice and control littermates (+/+): mineral apposition rate (MAR), bone formation rate (trabecular bone surface) (BFR/BS). *$P<0.05$, †$P<0.01$. Data are expressed as mean±s.e.m., n=4-5. For values other than presented here see the Supplementary Tables 1-3.

This invention relates in one embodiment to a novel factor required for optimal cell-cell fusion. In another embodiment, that factor is OCL-2A3, which is used interchangably herein with the term "Atp6v0d2".

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

In one embodiment, bone homeostasis is maintained by the balanced activities of matrix-producing osteoblasts and bone-resorbing osteoclasts. Osteoclasts are multinucleated, giant cells of hematopoietic origin and are formed by the fusion of mononuclear pre-osteoclasts derived from myeloid lineage cells. In one embodiment, fusion-mediated giant cell formation is critical for osteoclast maturation, and without it, in another embodiment, bone resorption is not efficient. In one embodiment, Atp6v0d2 is required for efficient Pre-osteoclast fusion.

In one embodiment, v-ATPase refers to vacuolar-type H$^±$ ATPase, a multisubunit enzyme, which is located in the osteoclast ruffled border membrane and maintains a low pH in the extracellular lacuna. In another embodiment, V-ATPase subunit mRNAs are highly expressed in resorbing osteoclasts, and the transcripts are polarized to the vincinity of the ruffled border area. V-ATPase is first expressed in the late osteoclast precursors, and in one embodiment, is considered an osteoclast phenotype marker. The v-ATPase complex is organized in one embodiment, into a peripheral V1 domain, composed of eight subunits (A to H) for ATP hydrolysis, and a membrane integral V0 domain, containing five subunits (a, d, c, c', and c") for proton translocation. Protons for this V-ATPase are generated by a cytoplasmic carbonic anhydrase II. Multiple isoforms of v-ATPase subunits show distinct cell-type and tissue-specific expressions, and these isoforms account in one embodiment, for diverse physiological properties of ubiquitous v-ATPases in distinct cell types. Two isoforms of v-ATPase V0 subunit d; d1 and d2, have been identified in mouse and human. In one embodiment, OCL-2A3 gene encodes proteins identical to v-ATPase subunit d2 (Atp6v0d2).

In one embodiment, provided herein is an isolated mammalian osteoclast-specific nucleic acid sequence set forth in:

AGGACTCGGAGCCACTTCAGCCTGAG-CAGTATGCTTG (SEQ ID NO: 1)

AGACTGCAGAGCTGTACTTCAATGTG-GACCATGGCTA

CCTGGAGGGCCTGGTTCGAGGATG-CAAAGCCAGCCTC

CTAACTCAGCAGGACTATGTCAAC-CTAGTGCAGTGTG

AGACCTTGGAAGACCTGAAAAT-TCATCTCCAGACCAC

GGACTATGGCAACTTCCTGGCTAAT-GAAACAAATCCT

CTCACTGTTTCCAAAATTGACACG-GAGATGAGGAAGA

AGCTCTGCAGAGAGTTTGACTATTTCCG-GAATCATTC

CTTGGAGCCCCTGAGCACATTTCTCAC-CTACATGACA

-continued

TGCAGCTATATGATAGACAATATAATTC-
TACTTATGA

ATGGGGCCTTGCAAAAGAAATCTGT-
GAAAGAAGTTCT

AGCCAAGTGTCACCCACTGGGC-
CGTTTCACAGAGATG

GAAGCTGTCAACATTGCAGAGACCCCCT-
CAGATCTCT

TCAAGGCTGTGCTGGTTGAAACACCATT-
AGCTCCATT

CTTTCAAGATTGTATGTCTGAAAA-
CACTCTTGATGAA

CTGAATATTGAATTACTGCGCAATAAAC-
TATACAAGT

CTTACCTTGAGGCATTCTACAAATTCTG-
CAAGGATCA

CGGTGATGTCACAGCAGACGTTATGT-
GTCCCATTCTT

GAGTTTGAGGCCGACAGACGCGCTT-
TAATCATCACTC

TGAACTCATTTGGCACTGAACTAAG-
CAAAGAAGACAG

GGAGACCCTCTTCCCCACCTGCGGCAG-
GCTCTATCCA

GAGGGGTTGCGGTTGTTAGCTCAAGCT-
GAAGACTTTG

AGCAGATGAAGAGAGTGGCAGATAAT-
TATGGAGTTTA

CAAGCCTTTGTTTGACGCTGTCGGTG-
GCAGTGGGGGG

AAGACACTGGAAGACGTTTTCTAT-
GAGAGAGAGGTAC

AGATGAATGTGCTGGCATTCAACAG-
GCAATTCCATTA

TGGTGTGTTTTATGCGTATGTAAAGT-
TGAAGGAGCAA

GAGATGAGAAATATCGTGTGGATAGCA-
GAATGCATCT

CACAGAGGCATCGAACTAAAATCAA-
CAGCTACATTCC

AATTTTATAAGCCAGTGTACAGAAGAT-
CATACATGTT

GCCATGAAGTTATTGAGGAAAG-
GAAGGGGATTGTGT

CACATTATCTAGATTATATAAAG-
TAAGTCATACCAC

CTTTCCATAAACTACATGTCCACTG-
GAAGCCCAAGTA

AACAGAACTTGAAACAAAATATGC-
CTTTCTTGGTTTC

CAACAAGCCCCAGTGGTTTTTTCACATT-
TATGACTTC

CTGCTCACTGGCCTCATACGT-
TCATTTTCATTGACCC

TGTGGCACTTTTTGTATTCTCATTGGGT-
CAGACTAAA

-continued

ATCATAGGTAATCAGGT-
TCAAAAAAAAAAAAAAAAA

AAAA;

or

AGGACTCGGAGCCACTTCAGCCTGAG-     (SEQ ID NO: 2)
CAGTATGCTTG

AGACTGCAGAGCTGTACTTCAATGTG-
GACCATGGCTA

CCTGGAGGGCCTGGTTCGAGGATG-
CAAAGCCAGCCTC

CTAACTCAGCAGGACTATGTCAAC-
CTAGTGCAGTGTG

AGACCTTGGAAGACCTGAAAAT-
TCATCTCCAGACCAC

GGACTATGGCAACTTCCTGGCTAAT-
GAAACAAATCCT

CTCACTGTTTCCAAAATTGACACG-
GAGATGAGGAAGA

AGCTCTGCAGAGAGTTTGACTATTTCCG-
GAATCATTC

CTTGGAGCCCCTGAGCACATTTCTCAC-
CTACATGACA

TGCAGCTATATGATAGACAATATAATTC-
TACTTATGA

ATGGGCCTTGCAAAAGAAATCTGT-
GAAAGAAGTTCT

AGCCAAGTGTCACCCACTGGGC-
CGTTTCACAGAGATG

GAAGCTGTCAACATTGCAGAGACCCCCT-
CAGATCTCT

TCAAGGCTGTGCTGGTTGAAACACCATT-
AGCTCCATT

CTTTCAAGATTGTATGTCTGAAAA-
CACTCTTGATGAA

CTGAATATTGAATTACTGCGCAATAAAC-
TATACAAGT

CTTACCTTGAGGCATTCTACAAATTCTG-
CAAGGATCA

CGGTGATGTCACAGCAGACGTTATGT-
GTCCCATTCTT

GAGTTTGAGGCCGACAGACGCGCTT-
TAATCATCACTC

TGAACTCATTTGGCACTGAACTAAG-
CAAAGAAGACAG

GGAGACCCTCTTCCCCACCTGCGGCAG-
GCTCTATCCA

GAGGGGTTGCGGTTGTTAGCTCAAGCT-
GAAGACTTTG

AGCAGATGAAGAGAGTGGCAGATAAT-
TATGGAGTTTA

CAAGCCTTTGTTTGACGCTGTCGGTG-
GCAGTGGGGGG

AAGACACTGGAAGACGTTTTCTAT-
GAGAGAGAGGTAC

AGATGAATGTGCTGGCATTCAACAG-
GCAATTCCATTA

-continued

```
TGGTGTGTTTTATGCGTATGTAAAGT-
TGAAGGAGCAA

GAGATGAGAAATATCGTGTGGATAGCA-
GAATGCATCT

CACAGAGGCATCGAACTAAAATCAA-
CAGCTACATTCC

AATTTTATAAGCCAGTGTACAGAAGAT-
CATACATGTT

GCCATGAAGTTATTGAGGAAAG-
GAAGGGGGATTGTGT

CACATTATCTAGATTATATAAAAG-
TAAGTCATACCAC

CTTTCCATAAACTACATGTCCACTG-
GAAGCCCAAGTA

AACAGAACTTGAAACAAAATATGC-
CTTTCTTGGTTTC

CAACAAGCCCCAGTGGTTTTTTCACATT-
TATGACTTC

CTGCTCACTGGCCTCATACGT-
TCATTTTCATTGACCC

TGTGGCACTTTTTGTATTCTCATTGGGT-
CAGACTAAA

ATCATAGGTAATCAGGTTCTTCACGAGT-
TCTTTTCCG

TTCTTCTCCCCAAGCTCAAACACT-
GCTTTGCCTTTTA

CGTGTTTGGTCCTTCCATGCATTCAC-
GAAAATGCAAA

GCTGGGGGTAGCTAACATACACCATGCT-
TGGTGAAGA

CACGTTCCCTTCCTTTCCCCCAA-
GACTTTTGAGAAAG

ATAGATTCCCCAAATGCAAGCATTGT-
TAAATTTATTA

CTAAATTAGATTATCAACGCACACATA-
GAGACAGAGA

GAGAGAGAGAGAGACAGACAGACAGACA-
GACAGAAGG

ATGAATAACTTATATCGATATGTATAC-
CAGTGGTTCT

GTCATACTTTATTCCAGAAAATCCAAC-
TAATTGTACT

TTATTCCTTCAGATAGATGTAGATACAG-
CATGGTTGC

TACATAAAGTTGAAACAATGCAGAGGT-
TGCTCAGAAA

AAGAAAAATAGCAAAATGTGTCTC-
CAATCTTTTCTTT

AAATAGGAAATTTTTCTTAAATATAGTC-
TATGCTTGC

TCTGCTTCACAAATTAAATCTGTGCAGT-
CAACATGAT

GACTCAGCAGGTAAGAGCTTGAAGT-
CAACTCCATGAG

TTCGATTCCTGGAATCTCACATATG-
GAAGGAGGGAAC

TGCAAAACTACAAGATCATCTTTAATC-
CTTTAATCTT

TACTTATGCACCCCACCACTACACA-
CACTTACAAAAG

AATTTTAAAGAAGGGCACAGAAATAAT-
GTGAACTAAT

TTTACTATACACTCTCTATATACACAT-
GCTATGTAGA

ATAGTATGCATAAACTAAGGAGCACAA-
CATTTTTATG

TAGAATAATCATTTATAAATATAA-
CAAAAATAATGTT

TTGTTGAACTAAGAAGAAAGCCAAGTGC-
CTACTCCTT

GACTGCAGATGCAATTTACCCAGCTGC-
CTCCTGCCCA

GACCAACACACCTTCTCAACCACCTTA-
GACTGTCCTC

TCAAACCCTGACCCAAAAGAAACCCTTC-
CCTTTCTAA

ACTGTTGTTTCAGGTATTTTGTGGCAG-
CAACACAACA

AAGTAACTAATACAGAAAACTGATACT-
GCCATTGCTA

CAATAAACTTGATTTGGGATTGC-
CAAAAAAAAAAA

AAAAAAAA;
or

GGAAACTAGTCACAAAAACCCTGACTAT-    (SEQ ID NO: 3)
CACCTGATA

GATTGCTTGTGCTGCCTGATAAT-
TACTCGCACTTTTC

CCAGGCTAGTGCAAATCTTCAGGGGC-
CGTCCAGGACT

ACAGAGCTGTTTCACCCTACCTTGGCT-
TCAATCTCTT

CCCCCATGCTCGAAGGTGCGGAGCTG-
TACTTCAACGT

GGACCATGGCTACCTGGAGGGCCTGGT-
TCGAGGATGC

AAGGCCAGCCTCCTGACCCAGCAAGAC-
TATATCAACC

TGGTCCAGTGTGAGACCCTAGAAGACCT-
GAAAATTCA

TCTCCAGACTACTGATTATGG-
TAACTTTTTGGCTAAT

CACACAAATCCTCTTACTGTTTC-
CAAAATTGACACTG

AGATGAGGAAAAGACTATGTG-
GAGAATTTGAGTATTT

CCGGAATCATTCCCTGGAGCCCCTCAG-
CACATTTCTC

ACCTATATGACGTGCAGTTATATGATA-
GACAATGTGA

TTCTGCTGATGAATGGTGCATTGCA-
GAAAAAATCTGT
```

```
-continued
GAAAGAAATTCTGGGGAAGTGCCAC-
CCCTTGGGCCGT

TTCACAGAAATGGAAGCTGTCAACATTG-
CAGAGACAC

CTTCAGATCTCTTTAATGCCATTCT-
GATCGAAACGCC

ATTAGCTCCATTCTTCCAAGACTGCAT-
GTCTGAAAAT

GCTCTAGATGAACTGAATATTGAATTGC-
TACGCAATA

AACTATACAAGTCTTACCTTGAG-
GCATTTCTATAAAT

TCTGTAAGAATCATGGTGATGTCACAG-
CAGAAGTTAT

GTGTCCCATTCTTGAGTTTGAGGCCGA-
CAGACGTGCT

TTTATCATCACTCTTAACTCCTTTG-
GCACTGAATTGA

GCAAAGAAGACCGAGAGACCCTCTATC-
CAACCTTCGG

CAAACTCTATCCTGAGGGGTTGCGGCT-
GTTGGCTCAA

GCAGAAGACTTTGACCAGATGAAGAACG-
TAGCGGATC

ATTACGGAGTATACAAACCTT-
TATTTGAAGCTGTAGG

TGGCAGTGGGGGAAAGACATTGGAG-
GACGTGTTTTAC

GAGCGTGAGGTACAAATGAATGTGCTG-
GCATTCAACA

GACAGTTCCACTACGGTGTGTTTTATG-
CATATGTAAA

GCTGAAGGAACAGGAAATTAGAAATAT-
TGTGTGGATA

GCAGAATGTATTTCACAGAGGCATC-
GAACTAAAATCA

ACAGTTACATTCCAATTTTATAAC-
CCAAGTAAGGTTC

TCAAATGTAGAAAATTATAAATGT-
TAAAAGGAAGTTA

TTGAAGAAAATAAAAGAAATTATGT-
TATATTAAAAAA

AAAAAAAAAAAA
or:

GGAAACTAGTCACAAAAACCCTGACTAT-        (SEQ ID NO: 4)
CACCTGATA

GATTGCTTGTGCTGCCTGATAAT-
TACTCGCACTTTTC

CCAGGCTAGTGCAAATCTTCAGGGGC-
CGTCCAGGACT

ACAGAGCTGTTTCACCCTACCTTGGCT-
TCAATCTCTT

CCCCCATGCTCGAAGGTGCGGAGCTG-
TACTTCAACGT

GGACCATGGCTACCTGGAGGGCCTGGT-
TCGAGGATGC

AAGGCCAGCCTCCTGACCCAGCAAGAC-
TATATCAACC

TGGTCCAGTGTGAGACCCTAGAAGACCT-
GAAAATTCA

TCTCCAGACTACTGATTATGG-
TAACTTTTTGGCTAAT

CACACAAATCCTCTTACTGTTTC-
CAAAATTGACACTG

AGATGAGGAAAAGACTATGTG-
GAGAATTTGAGTATTT

CCGGAATCATTCCCTGGAGCCCCTCAG-
CACATTTCTC

ACCTATATGACGTGCAGTTATATGATA-
GACAATGTGA

TTCTGCTGATGAATGGTGCATTGCA-
GAAAAAATCTGT

GAAAGAAATTCTGGGGAAGTGCCAC-
CCCTTGGGCCGT

TTCACAGAAATGGAAGCTGTCAACATTG-
CAGAGACAC

CTTCAGATCTCTTTAATGCCATTCT-
GATCGAAACGCC

ATTAGCTCCATTCTTCCAAGACTGCAT-
GTCTGAAAAT

GCTCTAGATGAACTGAATATTGAATTGC-
TACGCAATA

AACTATACAAGTCTTACCTTGAGGCAT-
TCTATAAATT

CTGTAAGAATCATGGTGATGTCACAGCA-
GAAGTTATG

TGTCCCATTCTTGAGTTTGAGGCCGACA-
GACGTGCTT

TTATCATCACTCTTAACTCCTTTG-
GCACTGAATTGAG

CAAAGAAGACCGAGAGACCCTCTATC-
CAACCTTCGGC

AAACTCTATCCTGAGGGGTTGCGGCTGT-
TGGCTCAAG

CAGAAGACTTTGACCAGATGAAGAACG-
TAGCGGATCA

TTACGGAGTATACAAACCTT-
TATTTGAAGCTGTAGGT

GGCAGTGGGGAAAGACATTGGAG-
GACGTGTTTTACG

AGCGTGAGGTACAAATGAATGTGCTG-
GCATTCAACAG

ACAGTTCCACTACGGTGTGTTTTATG-
CATATGTAAAG

CTGAAGGAACAGGAAATTAGAAATAT-
TGTGTGGATAG

CAGAATGTATTTCACAGAGGCATCGAAC-
TAAAATCAA

CAGTTACATTCCAATTTTATAACCAAG-
TAAGGTTCT

CAAATGTAGAAAATTATAAATGT-
TAAAAGGAAGTTAT
```

-continued

TGAAGAAAATAAAAGAAATTATGT-
TATATTATCTAGA

CTACACAAAAGTAAGCCACACTATATCT-
TCATGAGTT

GCAAATCCATGGAAACACAGTAAAC-
CAGCCCTGAAAC

AAAGCATTTCCTTGTTTTCAGTGG-
TATTAGATCTTGT

TTCCACATGTCTGTCTCATTCT-
TCACTGGGCCTTACA

GGTTAGTTTTAATTAACTCTATGG-
TATTTTTCTTATT

CTTGTTTGATCATGTTAAAAATTGGAC-
CTAATAAAAG

TATTTTATTCTTGCTTTTCCATGCT-
TCTCTACAGGTC

CAAATACTGAATGTCTCCTT-
TACTTTTTCTCTTTTAA

ATTTTTTTCTAGACAGGGTCTCACTCT-
GTCACCTAGG

CTACAGTGCAGTGGTGTGATCACAGCT-
CACTGCAGCC

TCGACTTCCCAGGCTCAAGTGATCCTC-
CCAGCTCTCA

GCCTCCAAAGTAGCTGGCACTACAAGTG-
TACACCCCC

ACACAAGGCTAAGTTTTGTATTTTTTG-
TAGAGACAGG

GTTTCAACATATTATCCAGGCTGGTGTC-
GAATTCCTG

GGCTCCAGGGATCCACAGTCCCCCTTG-
GCCTCCCAAA

GTGTTGGGATTACATGCATGAGCCACT-
GTGCTGGGCT

TCATTTACATTTTAACTGTCTGTTCCT-
TGCCTAGATT

CACAGAAATCCAAAGCTGTATGTAGT-
CAACATGGTTC

ACAAGTGTTGGAAAATGT-
GTTTTTTGTTTTGTTTGT

TTTGTTTCGTTTTGTTTTGAGACA-
GAGTTTCCCTCTG

TCGCCCAGGCTAGAGTGCAATGGCGT-
GATCTCGGCTC

ACTGCAACCTCCACCTCCCAGATTCAAG-
CAACTCTCT

GCCTCAGCCTCCCGAGTAGCTGGGATTA-
CAAGCACCC

ACCACTACACTCAGCTAATTTTTTG-
TATTTTTAGTAG

AGCCGGGGTTTCACCATCTTGGCCAG-
GCTGATCTTGA

ACTCCTGAGCTCATGATCCACCCGCCT-
CAGCCTCCCA

AAGTGCTGGGATTACAGGCCCCTTGT-
TCAGCCACTGC

-continued

ACCTGGCCCCT-
TATTTTGTTTTTGTTTTCTAATATAC

TTTGATGTAATCAGCTTGAGAAAGCAA-
CACAATTTCA

AATCCTATCTTCTAGATGCAAGCAGTGT-
TAAATTTGT

TAATAAATTTGCTTTTCACACCTTTCTT-
TAAATAAAA

GGTATATCTCTCTT-
TAAAAAAAAAAAAAAAAAAAAA

AA, including variants and fragments thereof.

In one embodiment provided herein is an isolated nucleic acid molecule, degenerate variants thereof, fragments thereof, or analogs or derivatives thereof, which encodes Atp6v0d2, conserved variants thereof, fragments thereof, or analogs or derivatives thereof. Examples of such isolated nucleic acid molecules comprise a DNA sequence of SEQ ID No.s 1-4, degenerate variants of these sequences, fragments thereof, or analogs or derivatives thereof. These isolated nucleic acid molecules encode in another embodiment Atp6v0d2, including a full length, or naturally occurring forms of this enzyme subunit, and any antigenic fragments thereof from any animal; such as mammalian, or in another embodiment human, source.

In one embodiment, due to degenerate nature of codons in the genetic code, OCL-2A3, or in another embodiment—Atp6v0d2 provided herein, can be encoded by numerous degenerate variants of isolated nucleic acid molecules provided herein. "Degenerate nature" refers in one embodiment to the use of different three-letter codons to specify a particular amino acid pursuant to the genetic code. As is well known in the art; the following codons can be used in certain embodiments to interchangeably code for each specific amino acid:

| Amino Acid | Notation | Interchangeable Codons |
|---|---|---|
| Phenylalanine | Phe (F) | UUU or UUC |
| Leucine | Leu (L) | UUA or UUG or CUU or CUC or CUA or CUG |
| Isoleucine | Ile (I) | AUU or AUC or AUA |
| Valine | Val (V) | GUU or GUC of GUA or GUG |
| Serine | Ser (S) | UCU or UCC or UCA or UCG or AGU or AGC |
| Proline | Pto (P) | CCU or CCC or CCA or CCG |
| Threonine | Thr (T) | ACU or ACC or ACA or ACG |
| Alanine | Ala (A) | GCU or GCG or GCA or GCG |
| Tyrosine | Tyr (Y) | UAU or UAC |
| Histidine | His (H) | CAU or CAC |
| Glutamine | Gln (Q) | CAA or CAG |
| Asparagine | Asn (N) | AAU or AAC |
| Lysine | Lys (K) | AAA or AAG |
| Aspartic Acid | Asp (D) | GAU or GAC |

-continued

| Amino Acid | Notation | Interchangeable Codons |
|---|---|---|
| Glutamic Acid | Glu (E) | GAA or GAG |
| Cystein | Cys (C) | UGU or UGC |
| Arginine | Arg (R) | CGU or CGC or CGA or CGG or AGA or AGG |
| Glycine | Gly (G) | GGU or GGC or GGA or GGG |
| Termination Codon | | UAG (amber) or UAA (ochre) or UGA (opal) |

It should be understood that the codons specified above are for RNA sequences. The corresponding codons for DNA have a T substituted for U.

In one embodiment, provided herein is vector comprising the isolated nucleic acid sequence encoding OCL-2A3, or in another embodiment—Atp6v0d2. In one embodiment, the term "vector" refers to a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control. Provided herein are cloning vectors comprising the isolated nucleic acid molecule of the present invention, or degenerate variants thereof, fragments thereof, analogs or derivatives thereof, and an origin of replication. In one embodiment, the term "origin of replication" refers to those DNA sequences that participate in DNA synthesis. In one embodiment, provided herein is a vector comprising an isolated nucleic acid molecule comprising a sequence as set forth in SEQ ID NO.s 1-4, degenerate variants thereof, fragments thereof, or analogs or derivatives thereof, which encodes OCL-2A3, or in another embodiment—Atp6v0d2, conserved variants thereof, fragments thereof, or analogs or derivatives thereof, and an origin of replication. In another embodiment, the vector as provided herein comprises an isolated nucleic acid molecule hybridizable under standard hybridization conditions to an isolated nucleic acid molecule comprising a sequence as set forth in SEQ ID NO. 1-4, degeneratevariants thereof, fragments thereof, or analogs or derivatives thereof, and an origin of replication. A large number of vector-host systems known in the art may be used. In one embodiment, the vectors are a plasmid, cosmid, yeast artificial chromosome (YAC), BAC, adenovirus, lentivirus, adeno-associated virus, retovirus, P1, bacteriophage or eukaryotic viral DNA, so long as the vector system is compatible with the host cell used in certain embodiments.

In other embodiments, vectors having applications in the present invention include, but are not limited to E. coli. bacteriophages such as lambda derivatives, or plasmids such as pBR322 derivatives or pUC plasmid derivatives, e.g., pGEX-vectors, pmal-c, pFLAG, etc. The insertion an isolated nucleic acid molecule as provided hereinul to a cloning vector can, for example, be accomplished by ligating the isolated nucleic acid molecule into a vector which has complementary cohesive termini. In another embodiment, if the complementary restriction sites used to fragment the isolated nucleic acid, degenerate variants thereof, fragments thereof, or analogs or derivatives thereof, or an isolated nucleic acid hybridizable thereto under standard hybridization conditions, are not present in the vector, the ends of the isolated nucleic acid molecule, degenerate variants thereof, fragments thereof, or analogs or derivatives thereof, or an isolated nucleic acid molecule hybridizable thereto under standard hybridization conditions may be enzymatically modified. In one embodiment, any site desired may be produced by ligating nucleotide sequences (linkers) onto the DNA termini; these ligated linkers may comprise in other embodiments, specific chemically synthesized oligonucleotides encoding restriction endonuclease recognition sequences. Such recombinant molecules are introduced in other embodiments into host cells via transformation, transfection, infection, electroporation, etc., so that many copies of an isolated nucleic acid molecule of the present invention, degeneratevariants thereof, fragments thereof, or analogs or derivatives thereof can be generated. In one embodiment, cloned isolated nucleic acid molecule are contained on a shuttle vector plasmid, which provides for expansion in a cloning cell, e.g., E. coli, and facile purification for subsequent insertion into an appropriate expression cell line, if such is desired. For example, a shuttle vector, referring to a vector that can replicate in more than one type of organism, can be prepared for replication in both E. coli and Saccharomyces cerevisiae by linking sequences from an E. coli plasmid with sequences from the yeast 2μ. plasmid.

In one embodiment, provided herein is a polypeptide encoded by the isolated nucleic acid set forth in SEQ ID NO.s 1-4, degenerate variants thereof, fragments thereof, or analogs or derivatives thereof, which encodes OCL-2A3, or in another embodiment—Atp6v0d2, conserved variants thereof, fragments thereof, or analogs or derivatives thereof, and an origin of replication. In another embodiment the nucleic acid encodes an amino acid sequence having the sequence as set forth in:

Met-Leu-Glu-Thr-Ala-Glu-Leu-Tyr-    (SEQ ID NO. 5)
Phe-Asn-Val-Asp-His-Gly-Tyr-Leu-
Glu-Gly-Leu-Val-Arg-Gly-Cys-Lys-
Ala-Ser-Leu-Leu-Thr-Gln-Gln-Asp-
Tyr-Val-Asn-Leu-Val-Gln-Cys-Glu-
Thr-Leu-Glu-Asp-Leu-Lys-Ile-His-
Leu-Gln-Thr-Thr-Asp-Tyr-Gly-Asn-
Phe-Leu-Ala-Asn-Glu-Thr-Asn-Pro-
Leu-Thr-Val-Ser-Lys-Ile-Asp-Thr-
Glu-Met-Arg-Lys-Lys-Leu-Cys-Arg-
Glu-Phe-Asp-Tyr-Phe-Arg-Asn-His-
Ser-Leu-Glu-Pro-Leu-Ser-Thr-Phe-
Leu-Thr-Tyr-Met-Thr-Cys-Ser-Tyr-
Met-Ile-Asp-Asn-Ile-Ile-Leu-Leu-
Met-Asn-Gly-Ala-Leu-Gln-Lys-Lys-
Ser-Val-Lys-Glu-Val-Leu-Ala-Lys-
Cys-His-Pro-Leu-Gly-Arg-Phe-Thr-
Glu-Met-Glu-Ala-Val-Asn-Ile-Ala-
Glu-Thr-Pro-Ser-Asp-Leu-Phe-Lys-
Ala-Val-Leu-Val-Glu-Thr-Pro-Leu-
Ala-Pro-Phe-Phe-Gln-Asp-Cys-Met-

-continued
```
Ser-Glu-Asn-Thr-Leu-Asp-Glu-Leu-
Asn-Ile-Glu-Leu-Leu-Arg-Asn-Lys-
Leu-Tyr-Lys-Ser-Tyr-Leu-Glu-Ala-
Phe-Tyr-Lys-Phe-Cys-Lys-Asp-His-
Gly-Asp-Val-Thr-Ala-Asp-Val-Met-
Cys-Pro-Ile-Leu-Glu-Phe-Glu-Ala-
Asp-Arg-Arg-Ala-Leu-Ile-Ile-Thr-
Leu-Asn-Ser-Phe-Gly-Thr-Glu-Leu-
Ser-Lys-Glu-Asp-Arg-Glu-Thr-Leu-
Phe-Pro-Thr-Cys-Gly-Arg-Leu-Tyr-
Pro which may have, for example, modifications rendering the peptides more stable while in a body or more capable of penetrating into cells, such as ostoeclast cell in certain embodiments. Such modifications include, but are not limited to N terminal, C terminal or peptide bond modification, including, but not limited to, backbone modifications, and residue modification, each of which represents an additional embodiment of the invention. Methods for preparing peptidomimetic compounds are well known in the art and are specified, for example, in Quantitative Drug Design, C. A. Ramsden Gd., Chapter 17.2, F. Choplin Pergamon Press (1992).

In one embodiment, the term "antibody" include complete antibodies (e.g., bivalent IgG, pentavalent IgM) or fragments of antibodies in other embodiments, which contain an antigen binding site. Such fragment include in one embodiment Fab, $F(ab')_2$, Fv and single chain Fv (scFv) fragments. In one embodiment, such fragments may or may not include antibody constant domains. In another embodiment, F(ab)'s lack constant domains which are required for complement fixation. scFvs are composed of an antibody variable light chain ($V_L$) linked to a variable heavy chain ($V_H$) by a flexible linker. scFvs are able to bind antigen and can be rapidly produced in bacteria. The invention includes antibodies and antibody fragments which are produced in bacteria and in mammalian cell culture. An antibody obtained from a bacteriophage library can be a complete antibody or an antibody fragment. In one embodiment, the domains present in such a library are heavy chain variable domains ($V_H$) and light chain variable domains ($V_L$) which together comprise Fv or scFv, with the addition, in another embodiment, of a heavy chain constant domain ($C_{H1}$) and a light chain constant domain ($C_L$). The four domains (i.e., $V_H$-$C_{H1}$ and $V_L$-$C_L$) comprise an Fab. Complete antibodies are obtained in one embodiment, from such a library by replacing missing constant domains once a desired $V_H$-$V_L$ combination has been identified.

The antibodies described herein can be monoclonal antibodies (Mab) in one embodiment, or polyclonal antibodies in another embodiment. Antibodies of the invention which are useful for the compositions, methods and contraceptives described herein can be from any source, and in addition may be chimeric. In one embodiment, sources of antibodies can be from a mouse, or a rat, or a human in other embodiments. Antibodies of the invention which are useful for the compositions, methods and contraceptives of the invention have reduced antigenicity in humans, and in another embodiment, are not antigenic in humans. Chimeric antibodies as described herein contain in one embodiment, human amino acid sequences and include humanized antibodies which are non-human antibodies substituted with sequences of human origin to reduce or eliminate immunogenicity, but which retain the binding characteristics of the non-human antibody. In one embodiment, the antibody used to inhibit function of Atp6v0d2 or OCL-2A3, is a Atp6v0d2 or OCL-2A3-specific monoclonal antibody (MoAb).

In certain embodiments, the antibodies employed in the compositions described herein and used in the methods described herein, will be "humanized", part-human or human antibodies. In one embodiment, "Humanized" antibodies are chimeric monoclonal antibodies from mouse, rat, or other non-human species, bearing human constant and/or variable region domains ("part-human chimeric antibodies"). Various humanized monoclonal antibodies for use in the present invention will be chimeric antibodies wherein at least a first antigen binding region, or complementarity determining region (CDR), of a mouse, rat or other non-human monoclonal antibody is operatively attached to, or "grafted" onto, a human antibody constant region or "framework". "Humanized" monoclonal antibodies for use herein may also be monoclonal antibodies from non-human species wherein one or more selected amino acids have been exchanged for amino acids more commonly observed in human antibodies. This can be readily achieved through the use of routine recombinant technology, particularly site-specific mutagenesis In one embodiment, the isolated nucleic acids used in the compositions and methods described herein have a nucleic acid sequence of about 62.5 to about 99% similarity with the nucleic acid coding sequence of SEQ ID NOs: 1-4, including variants and fragments thereof.

In one embodiment, the similarity Atp6v0d2 or OCL-2A3 gene encoding the Atp6v0d2 or OCL-2A3 protein described herein, which is used in the methods and compositions described herein refers to the sequence exhibiting substantial complimentarity to its refernce sequence. In another embodiment, "complementarity" indicates that the oligonucleotide has a base sequence containing an at least 15 contiguous base region that is at least 70% complementary, or in another embodiment at least 80% complementary, or in another embodiment at least 90% complementary, or in another embodiment 100% complementary to an-at least 15 contiguous base region present on a reference gene sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization). The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 15 contiguous bases being compared, which may range from 0-3 base mismatches, so long as their functionality for the purpose used is not compromised.

In another embodiment, the similarity Atp6v0d2 or OCL-2A3 gene encoding the Atp6v0d2 or OCL-2A3 protein as described herein, which is used in the methods and compositions described herein refers to the sequence being sufficiently complimentary to its reference sequence. "Sufficiently complementary" refers in one embodiment to a contiguous nucleic acid base sequence that is capable of hybridizing to another base sequence by hydrogen bonding between a series of complementary bases. In another embodiment, complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are at least about 80% in one embodiment, or at least about 90% in another embodiment, or about 100% complementary to a sequence to which an oligonucleotide is intended to specifically hybridize in another embodiment. Appropriate hybridization conditions are well known to those skilled in the art, can be predicted readily based on base sequence composition, or can be determined empirically by using routine testing (e.g., See Sambrook et al., Molecular Cloning. A Laboratory Manual, 2$^{nd}$ ed. (Cold Spring Harbor Laboratory Press, Cold Spring Harbor, N.Y., 1989).

In one embodiment the Atp6v0d2 or OCL-2A3 gene has a nucleotide sequence having at least 60% similarity with the nucleic acid coding sequence of SEQ ID NO.s: 1-4. In another embodiment the nucleic acid has a nucleotide sequence having at least 87% similarity with the nucleic acid coding sequence of SEQ ID NO.s: 1-4. In another embodiment the nucleic acid has a nucleotide sequence having at least 90% similarity with the nucleic acid coding sequence of SEQ ID NO.s: 1-4. In another embodiment the nucleic acid has a nucleotide sequence having at least 95% similarity with the nucleic acid coding sequence of SEQ ID NO.s: 1-4.

It will be appreciated by those skilled in the art that DNA sequence polymorphisms that lead to changes in the amino acid sequences of Atp6v0d2 or OCL-2A3 may exist within a population (e.g., the human population). Such genetic polymorphism in the Atp6v0d2 or OCL-2A3 gene may exist among individuals within a population due to natural allelic variation. An allele is one of a group of genes which occur alternatively at a given genetic locus. Such natural allelic variations can typically result in 1-5% variance in the nucleotide sequence of the Atp6v0d2 or OCL-2A3 gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms in Atp6v0d2 or OCL-2A3 that are the result of natural allelic variation and that do not alter the functional activity of Atp6v0d2 or OCL-2A3 are intended to be within the scope of the invention. Moreover, nucleic acid molecules encoding Atp6v0d2 or OCL-2A3 proteins from other species (Atp6v0d2 or OCL-2A3 homologues), which have a nucleotide sequence which differs from that of a human Atp6v0d2 or OCL-2A3, are intended to be within the scope of the invention. Nucleic acid molecules corresponding to natural allelic variants and homologues of the Atp6v0d2 or OCL-2A3 cDNA of the invention can be isolated based on their identity to the human Atp6v0d2 or OCL-2A3 nucleic acids disclosed herein using the human cDNAs, or a portion thereof, as a hybridization probe according to standard hybridization techniques under stringent hybridization conditions. For example, splice variants of human and mouse Atp6v0d2 or OCL-2A3 cDNA can be isolated based on identity to human and mouse Atp6v0d2 or OCL-2A3.

In one embodiment, provided herein is a Atp6v0d2 or OCL-2A3 polypeptide, having an amino acid sequence having at least 60% similarity with the amino acid sequence of SEQ ID NO.s: 5-6. In another embodiment the nucleic acid has a nucleotide sequence having at least 87% similarity with the nucleic acid coding sequence of SEQ ID NO.s: 5-6. In another embodiment the nucleic acid has a nucleotide sequence having at least 90% similarity with the nucleic acid coding sequence of SEQ ID NO.s: 5-6. In another embodiment the nucleic acid has a nucleotide sequence having at least 95% similarity with the nucleic acid coding sequence of SEQ ID NO.s: 5-6, including in other embodiments, variants and fragments thereof as describe herein.

In one embodiment, the nucleotide sequences, as well as variants and fragments thereof as describe herein, and the amino acid sequences as well as variants and fragments thereof as describe herein and are set forth in SEQ ID NO.s 1-4 and 5-6, are used in the compositions ande methods described hereinbelow.

In one embodiment, provided herein is a method for detecting osteoclast specific OCL-2A3 expressing cells in a mixed cells population, comprising: identifying cells expressing SEQ ID NO.s 1-4 or 5-6, including variants, fragments and mutants, thereof whereby expression of said sequences indicate a OCL-2A3 osteoclast cell. In another embodiment, OCL-2A3, refers to Atp6v0d2.

In another embodiment, provided herein is a method for identifying a modulator of a cell expressing OCL-2A3 function comprising: contacting the cell with a candidate agent; and analyzing said agent for its ability to modulate the expression of SEQ ID NO.s 1-4, genes regulated by the expression of SEQ ID NO.'s 1-4, or activity of a polypeptide encoded thereby, whereby an ability of the candidate agent to downregulate or upregulate the expression of SEQ ID NO.s 1-4, genes regulated by the expression of SEQ ID NO.'s 1-4, or its encoded polypeptides indicate the agent is a modulator.

In one embodiment, "contacting" a cell with a substance refers to (a) providing the substance to the environment of the cell (e.g., solution, in vitro culture medium, anatomic fluid or tissue) or (b) applying or providing the substance directly to the surface of the cell, in either case so that the substance comes in contact with the surface of the cell in a manner allowing for biological interactions between the cell and the substance, which in another embodiment, is the candidate agent.

It is to be understood that the use of the term "modulates" is to refer to stimulating, enhancing, inhibiting or abrogating, as defined herein. Modulating Atp6v0d2 refers to Atp6v0d2 expression. In another embodiment, Atp6v0d2 activity is modulated, as described. In another embodiment, effects of Atp6v0d2 expression and/or activity are via Atp6v0d2 ubiquitination and/or degradation.

In one embodiment, the agent identified using the methods described herein, is used in the compositions and methods described herein. In another embodiment, provided herein is a composition for use in modulating OCL-2A3 function comprising the agent identified using the methods described herein. In one embodiment, provided herein is a method for treatment of a disease linked to OCL-2A3, comprising the step of administering to a patient suffering from such a disease the compositions described herein.

In one embodiment, provided herein is a method of increasing bone mass in a subject, comprising the step of administering to said subject an agent able to inhibit the expression or function of a gene encoding OCL-2A3 in the subject, thereby inhibiting bone resorption, increasing bone formation or a combination thereof.

The desired dosage of active compound in the compositions described herein, which may be used for the methods described herein will vary, depending on the mode of administration, the condition to be treated, the overall condition of the subject, and the compound administered. It is well within the capability of a competent technician to determine the appropriate dosage for a particular patient in light of these factors. It is anticipated that in one non-limiting embodiment, where the systemic administration of the compositions described herein by injection is desired, the appropriate dosage will be between 1 mg to 20 mg of the agent able to inhibit the expression or function of a gene encoding OCL-2A3 in the subject per kg body weight. Depending on the subject and the condition to be treated, in one embodiment, dosages will be between about 1 to about 10 mg per kg body weight for subjects whose existing bone density is not extremely low; or, in another embodiment, between about 10 mg to about 20 mg per kg body weight for subjects whose bone density is extremely low.

Where localized administration of the compositions described herein is desired, the to appropriate localized dosage can be determined with reference to the level of compound desired in the treatment area. In another embodiment, the total dosage required for localized treatment will be lower than that level required for systemic treatment, and in one embodiment, the appropriate localized dosage will be ten to one-hundred fold lower than the amount of compound required for systemic treatment.

Figure 18:
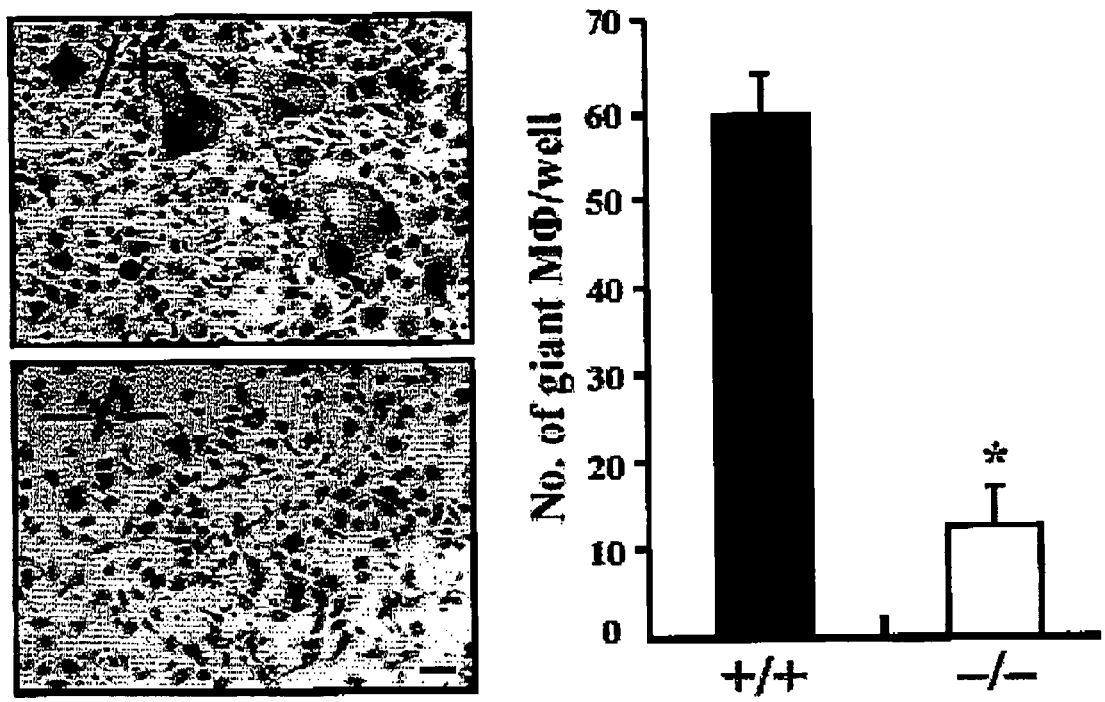
FIG. 18 shows that disruption of Atp6v0d2 affects cytokine-induced macrophage cell fusion. Although significantly less than in osteoclasts, Atp6v0d2 expression can be detected in macrophages (FIG. 1). Macrophages from wild-type and Atp6v0d2$^{-/-}$ cells were treated with IL-3 and IL-4 to induce giant cell formation. Cells were stained with May-Gruenwald Giemsa. Giant cells (>100 μm in diameter) that contain more than 5 nuclei were counted. Data represent mean±s.d. *P<0.001; Scale bar=100 μm.

In one embodiment, Atp6v0d2 is a novel factor required for optimal cell-cell fusion. In another embodiment, cytokine-induced fusion of macrophages is severely impaired in the absence of Atp6v0d2 (FIG. 18). In another embodiment, the involvement of Atp6v0d2 in cell-cell fusion is tissue-specific, since Atp6v0d2-deficient mice do not show gross defects in other tissues or in the generation of offspring. in another embodiment, the role of v-ATPase complex subunits as cell-cell fusion regulators has been preserved during evolution from nematodes to vertebrates.

Figure 8:
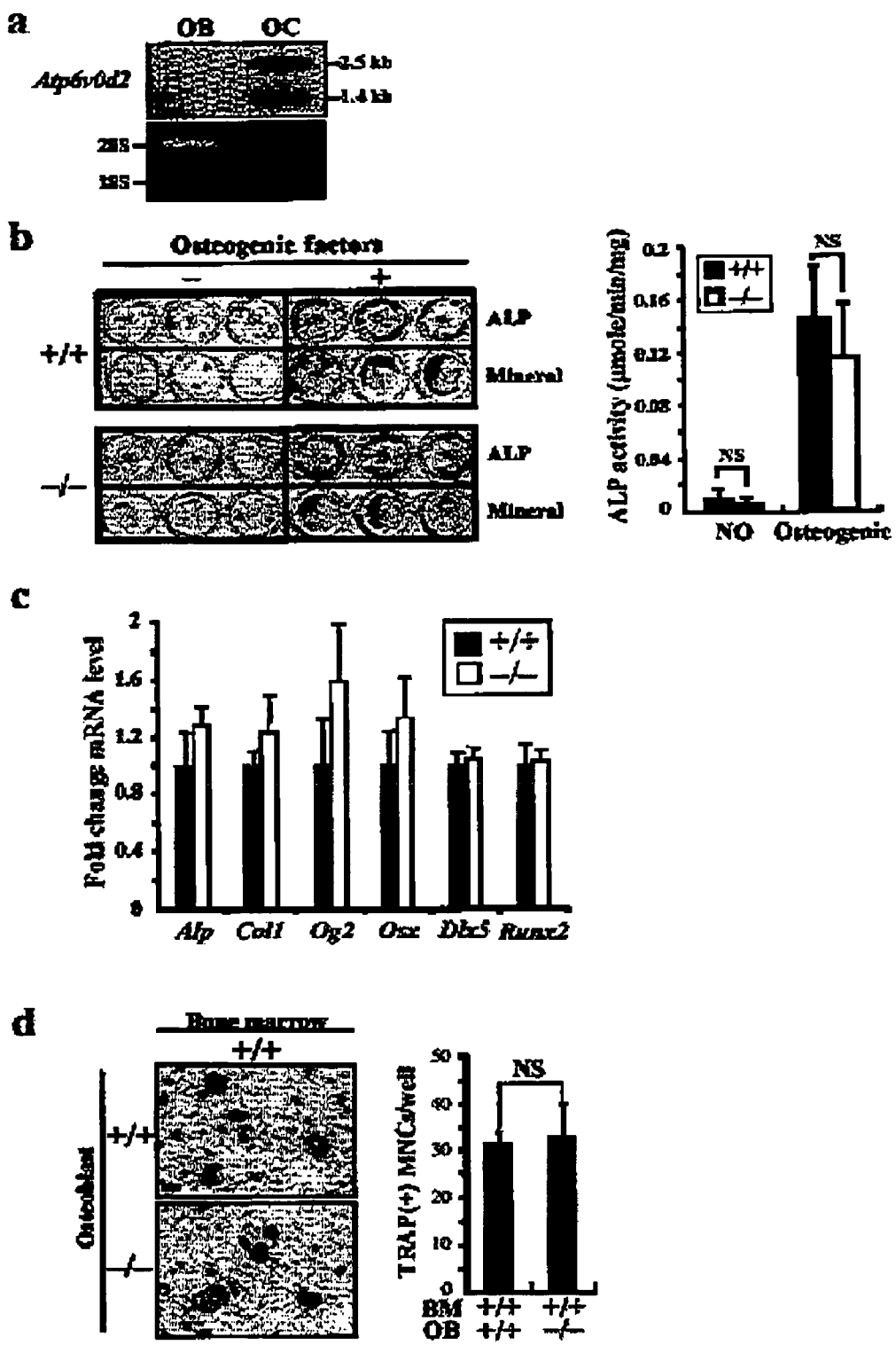
FIG. 8 shows that osteoblast function and differentiation are not affected by Atp6v0d2 deficiency. (a) Total RNA was isolated from in vitro differentiated osteoblasts, and analyzed for Atp6v0d2 mRNA by northern blot. Even longer exposure does not exhibit any detectable Atp6v0d2 mRNA in osteoblasts. (b) Osteoblast differentiation was assessed by ALP activity and mineralized nodule. (c) Quantitative RT-PCR analysis of osteoblast markers during osteoblastogenic culture conditions. RNA was prepared on day 8 for alkaline phosphatase (Alp), distal-less homeobox (Dlx5), osterix (Osx), and runt-related transcription factor 2 (Runx2), and on day 10 for collagen Type Ia (Col1) and osteocalcin (Og2). The expression level in Atp6v0d2−/− osteoblasts, relative to that in wild-type control littermate osteoblasts, is indicated as a ratio. None showed any statistically significant difference. (d) Bone-marrow cells from wild-type mice were co-cultured for 8 days with osteoblasts derived from calvarias of wild-type littermates or Atp6v0d2−/− mice in presence of 1α,25(OH)$_2$D$_3$, and PGE$_2$. TRAP$^+$ MNCs were counted. Data represent mean±s.d. NS, not significant, Scale bar=100 μm.

In one embodiment, Atp6v0d2 dificient subjects surprisingly exhibit dramatic increase in osteoblast area (ObS/BS) as well as bone formation rate (MAR, BFR/BS) (FIG. 1c, g). In another embodiment, Atp6v0d2 deletion does not affect anabolic osteoblast differentiation as well as expression of osteoblast differentiation markers such as Dlx5, Osx or RUNX2 in vitro (FIG. 8). Thus increased osteoblast activity wherein Atp6v0d2 expression or function is inhibited using the compositions, agents and methods described herein, is due to osteoblast-extrinsic factors such as mutant osteoclasts in certain embodiments.

In one embodiment, the agent used in the compositions and methods described herein, affects the maturation or function of osteoclasts in the subject. In another embodiment, osteoclasts treated with the compositions and agents described herein are smaller than wild-type osteoclasts, which are usually >100 μm in diameter. The formation of large (>100 μm) osteoclasts containing more than 5 nuclei and an actin ring will greatly diminish in the presence of agents capable of inhibiting the expression or function of Atp6v0d2.

In one embodiment, the agent used in the compositions and methods described herein, is a siRNA, a miRNA, a virus, polyamides, triple-helix-forming agents, antisense RNA, synthetic peptide nucleic acids (PNAs), agRNA, LNA/DNA copolymers, or a combination thereof, specific against the gene encoding OCL-2A3.

In one embodiment, the term "siRNA" refers to RNA interference, which in another embodiment refers to the process of sequence-specific post-transcriptional gene silencing in animals, mediated by short interfering RNAs (siRNAs). In another embodiment, the process of post-transcriptional gene silencing is an evolutionarily-conserved cellular defense mechanism used to prevent the expression of foreign genes. Such protection from foreign gene expression evolved in one embodiment, in response to the production of double-stranded RNAs (dsRNAs) derived from viral infection or in another embodiment, from the random integration of transposon elements into a host genome via a cellular response that specifically destroys homologous single-stranded RNA of viral genomic RNA. In one embodiment, the presence of dsRNA in cells triggers the RNAi response.

In one embodiment, the term "conserved", refers to amino acid sequences comprising the peptides or nucleotides described herein, which remain in one embodiment, essentially unchanged throughout evolution, and exhibit homology among various species producing the protein.

The presence of long dsRNAs in cells stimulates in another embodiment, the activity of a ribonuclease III enzyme referred to as dicer. Dicer is involved in one embodiment, in the processing of the dsRNA into short pieces of dsRNA known as short interfering RNAs (siRNAs). Short interfering RNAs derived from dicer activity are in another embodiment about 21 to about 23 nucleotides in length and comprise about 19 base pair duplexes. Small RNAs function in one embodiment, by base-pairing to complementary RNA or DNA target sequences. When bound to RNA, small RNAs trigger RNA cleavage in another embodiment, or translational inhibition of the target sequence in another embodiment. When bound to DNA target sequences, small interfering RNAs mediate in one embodiment, DNA methylation of the target sequence. The consequence of these events, in one embodiment, is the inhibition of gene expression, which, in another embodiment is the Atp6v0d2 gene described herein. In one embodiment, the agent used for reducing the function of Atp6v0d2 gene or its encoded protein, is a siRNA specific for the nucleic acide encoding Atp6v0d2.

In one embodiment, the siRNA of the Atp6v0d2 gene described herein, exhibit substantial complimentarity to its target sequence. In another embodiment, "complementarity" indicates that the oligonucleotide has a base sequence containing an at least 15 contiguous base region that is at least 70% complementary, or in another embodiment at least 80% complementary, or in another embodiment at least 90% complementary, or in another embodiment 100% complementary to an-at least 15 contiguous base region present of a target gene sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization). The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 15 contiguous bases being compared, which may range from 0-3 base mismatches, so long as their functionality for the purpose used is not compromised.

In one embodiment, the siRNA of the Atp6v0d2 gene described herein is sufficiently complimentary to its target sequence. "Sufficiently complementary" refers in one embodiment to a contiguous nucleic acid base sequence that is capable of hybridizing to another base sequence by hydrogen bonding between a series of complementary bases. In another embodiment, complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are at least about 80% in one embodiment, or at least about 90% in another embodiment, or about 100% complementary to a sequence to which an oligonucleotide is intended to specifically hybridize in another embodiment. Appropriate hybridization conditions are well known to those skilled in the art, can be predicted readily based on base sequence composition, or can be determined empirically by using routine testing (e.g., See Sambrook et al., Molecular Cloning. A Laboratory Manual, 2$^{nd}$ ed. (Cold Spring Harbor Laboratory Press, Cold Spring Harbor, N.Y., 1989).

The term "nucleic acid" as used in connection with siRNA, refers in one embodiment to a polymer or oligomer composed of nucleotide units (ribonucleotides, deoxyribonucleotides or related structural variants or synthetic analogs thereof) linked via phosphodiester bonds (or related structural variants or synthetic analogs thereof). Thus, the term refers to a nucleotide polymer in which the nucleotides and the linkages between them are naturally occurring (DNA or RNA), as well as various analogs, for example and without limitation, peptide-nucleic acids (PNAs), phosphoramidates, phosphorothioates, methyl phosphonates, 2-O-methyl ribonucleic acids, and the like. In one embodiment, the siRNAs used in the compositions and methods of the invention, are nucleic acid sequences.

In one embodiment, minor groove-binding N-methylpyrrole (Py) and N-methylimidazole (Im) polyamides (peptides) uniquely recognize each of the four Watson-Crick base pairs. Antiparallel pairing of imidazole with pyrrole (Im/Py) recognizes in one embodiment, a G-C base pair, whereas in another embodiment, a Py/Py pair recognizes either an A-T or T-A base pair. The binding constant and sequence-specificity of the Py-Im hairpin polyamides are similar to that of a transcription factor. Therefore, many genes, are silenced in other embodiments, by competitive binding of Py-Im hairpin polyamides to their regulatory sequences. Gene expression is controlled in one embodiment, by a combination of multiple common trascription factors. Inhibition of gene expression through the binding of Py-Im polyamides to regulatory sequences is unique to a specific gene, and contains part of the recognition sequence of the transcription factor together with the unique flanking sequences. In another embodiment, targeting Py-Im polyamide to the coding region is more straightforward when selecting a unique sequence. In one embodiment, the agent used to silence the Atp6v0d2 gene in the methods and compositions described herein, is Py-Im polyamide specific for the miRNA region of that is comprised in SEQ ID NO. 1-4, or to regulatory sequences is unique to Atp6v0d2 in another embodiment. In another embodiment, the agent used to silence the Atp6v0d2 gene in the methods and compositions described herein, is a synthetic polyamide nucleic acid (PNA) specific for the coding region of Atp6v0d2, or to regulatory sequences, which is unique to Atp6v0d2 in another embodiment.

The term "miRNA" refers in one embodiment, to microRNA, a class of small RNA molecules or a small non-coding RNA molecules, that are capable of causing interference, inhibition of RNA translation into protein, and can cause post-transcriptional silencing of specific genes in cells. In one embodiment, miRNAs refers to small temporal RNAs (stRNAs), which belong to a class of non-coding microRNAs, shown in another embodiment to control gene expression either by repressing translation or by degrading the targeted mRNAs that are generally 20-28 nt (nucleotides) in length. In one embodiment, miRNA s or stRNAs are not encoded by any microgenes, but are generated from aberrant, dsRNAs by an enzyme called Dicer, which cuts double-stranded RNA into little pieces.

In one embodiment, the polyamides used in the compositions and methods described herein, which, in another embodiment are referred to as "peptide nucleic acid" (PNA) or "synthetic peptide nucleic acids", is an alkylating Py-Im polyamides that show sequence-specific DNA alkylation. In another embodiment, alkylation of a template strand in the a region comprised in SEQ ID NO.'s 1-4 of Atp6v0d2, by Py-Im polyamide-cyclopropylpyrroloindole (CPI) conjugates with a vinyl linker results in the production of truncated mRNA, effectively inhibiting transcription of Atp6v0d2 in vitro. In one embodiment, Py-Im tetra-hydro-cyclo-propa-benzindolone (CBI) conjugates with indole linkers are the alkylating polyamides used as the agent capable of inhibiting the expression or function of Atp6v0d2, or OCL-2A3 gene, because indole-CBI has increased chemical stability under acidic and basic conditions.

In one embodiment, oligodeoxynucleotides inhibit cellular transcription by binding to duplex DNA to form a triple helix. Due to the possibility of long-term inhibition of the gene product, oligodeoxynucleotides that can bind duplex DNA have advantages over those that bind mRNA or proteins. These oligodeoxynucleotides are generally called triplex forming oligonucleotides (TFOs). By using DNA-specific TFOs, the inhibition of expression of several cellular genes has been demonstrated, including the oncogene, c-myc, the human immunodeficiency virus-1, the alpha chain of the interleukin 2 receptor, the epidermal growth factor receptor, the progesterone responsive gene and the mouse insulin receptor. In one embodiment, the oligonucleotides used in the methods and compositions described herein, can bind to duplex DNA and form triple helices in a sequence-specific manner and will silence expression or function of Atp6v0d2.

In one embodiment, homopyrimidine DNA strand (triplex forming oligonucleotide, TFO) can bind to a homopurine/homopyrimide DNA duplex in the major groove by forming Hoogsteen base pairs with the homopurine strand. The Hoogsteen base pairing scheme mediates sequence specific recognition of the double stranded DNA by the TFO where in one to embodiment, an AT base pair is recognized by a T; and a GC base pair by a C that is protonated at $N3^+$. In another embodiment, homopurine strands specifically form a DNA triplex in which the AT base pair is contacted by an A; and the GC base pair by a G. In one embodiment, the agent capable of inhibiting the expression or function of Atp6v0d2 gene is a triple-helix-forming agents. In another embodiment, the triple-helix-forming agents are olygonucletides. In one embodiment, oligonucleotide-mediated triplex formation prevent transcription factor binding to promoter sites and block mRNA synthesis in vitro and in vivo.

In another embodiment, DNA intercalating or cross-linking agents are used to prolong oligonucleotide-duplex interactions.

In one embodiment, the term "TFO" or "triplex forming oligonucleotide" refers to the synthetic oligonucleotides of the present invention which are capable of forming a triple helix by binding in the major groove with a duplex DNA structure.

In another embodiment, the term "bases" refers to both the deoxyribonucleic acids and ribonucleic acids. The following abbreviations are used, "A" refers to adenine as well as to its deoxyribose derivative, "T" refers to thymine, "U" refers to uridine, "G" refers to guanine as well as its deoxyribose derivative, "C" refers to cytosine as well as its deoxyribose derivative. A person having ordinary skill in this art would readily recognize that these bases may be modified or derivatized to optimize the methods described herein, without changing the scope of the invention.

In one embodiment oligomeric antisense compounds, particularly oligonucleotides, are used in modulating the function of nucleic acid molecules of Atp6v0d2, ultimately modulating the amount of mRNA produced. This is accomplished by providing antisense compounds which specifically hybridize with one or more nucleic acids as described in SEQ ID NO.'s 1-4 including variant or fragments thereof. As used herein, the terms "target nucleic acid" and "nucleic acid encoding Atp6v0d2, RNA (including pre-mRNA and mRNA) transcribed from such DNA, and also cDNA derived from such RNA. The specific hybridization of an oligomeric compound with its target nucleic acid interferes in another embodiment, with the normal function of the nucleic acid. The modulation of function of a target nucleic acid by compounds which specifically hybridize to it, is referred to in one embodiment as "antisense". In one embodiment, the functions of DNA to be interfered with using the antisense oligonucleotides described herein, which are used in the methods, vaccines and compositions described herein, include replication and transcription. In another embodiment, functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the function of Atp6v0d2. In one embodiment, inhibition of gene expression is preferred and mRNA is a preferred target. In one embodiment, since many genes (including Atp6v0d2) have multiple transcripts, "inhibition" also includes an alteration in the ratio between gene products, such as alteration of mRNA splice products.

In one embodiment, specific nucleic acids are targeted for antisense. "Targeting" an antisense compound to a particular nucleic acid, in one embodiment, is a multistep process. The process usually begins with the identification of a nucleic acid sequence whose function is to be inhibited. This may be, for example, a cellular gene (or mRNA transcribed from the gene) whose expression is associated with a particular disorder or disease state, or a nucleic acid molecule from an infectious agent. In one embodiment, the target is a nucleic acid molecule encoding Atp6v0d2. The targeting process also includes in another embodiment, determination of a site or sites within this gene for the antisense interaction to occur such that the desired effect, e.g., inhibition of expression of the protein such as menin, will result. In one embodiment, an intragenic site is the region encompassing the translation initiation or termination codon of the open reading frame (ORF) of the gene. Since, the translation initiation codon is in one embodiment 5'-AUG (in transcribed mRNA molecules; 5'-ATG in the corresponding DNA molecule), the translation initiation codon is referred to in one embodiment as the "AUG codon," the "start codon" or the "AUG start codon". In another embodiment, a minority of genes have a translation initiation codon having the RNA sequence 5'-GUG, 5'-UUG or 5'-CUG, and 5'-AUA, 5'-ACG and 5'-CUG and have been shown to function in vivo. Thus, the terms "translation initiation codon" and "start codon" encompasses in other embodiments, many codon sequences, even though the initiator amino acid in each instance is typically methionine (in eukaryotes) or formylmethionine (in prokaryotes). In another embodiment, "start codon" and "translation initiation codon" refer to the codon or codons that are used in vivo to initiate translation of an mRNA molecule transcribed from a gene encoding Atp6v0d2 including variant or fragments thereof, regardless of the sequence(s) of such codons.

In certain embodiments, a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer in one embodiment, to a portion of such a mRNA or gene that encompasses from about 25 to about 50 contiguous nucleotides in either direction (i.e., 5' or 3') from a translation initiation codon. In another embodiment, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," refers in one embodiment to the region between the translation initiation codon and the translation termination codon, is a region which may be targeted effectively. Other target regions include in other embodiments, the 5' untranslated region (5'UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises in one embodiment, an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap. The 5' cap region is a preferred target region in one embodiment.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be target regions in one embodiment, and are particularly useful in situations where aberrant splicing is implicated in disease, or where an overproduction of a particular mRNA splice product is implicated in disease in other embodiment, such as symptoms associated with HSV infection. Aberrant fusion junctions due to rearrangements or deletions are also preferred targets. In one embodiment, introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect. In one embodiment, the term "hybridization" refers to hydrogen bonding, which may be Watson-Crick, Hoogsteen or reversed Hoogsteen hydrogen bonding, between complementary nucleoside or nucleotide bases. In one embodiment, adenine and thymine are complementary nucleotide bases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, or in the case of in vitro assays, under conditions in which the assays are performed.

Antisense compounds are used in one embodiment, as research reagents and diagnostics. In another embodiment, antisense oligonucleotides, which are able to inhibit gene function, such as the Atp6v0d2 gene, with extreme specificity, are used by those of ordinary skill to elucidate the function of particular genes. Antisense compounds are used in another embodiment, to distinguish between functions of various members of a biological pathway. Antisense modulation has, in one embodiment of the agents described in the methods and compositions described herein, been harnessed for research use.

In one embodiment, the specificity and sensitivity of antisense agents described herein, is also harnessed for therapeutic uses. Antisense oligonucleotides are employed in one embodiment, as therapeutic moieties in the treatment of disease states in animals and man, such as, in another embodiment, those associated with imbalanced bone resorption and anabolic bone formation. In one embodiment, antisense oligonucleotides are safely and effectively administered to humans. In one embodiment oligonucleotides are useful therapeutic modalities that can be configured to be useful in treatment regimes of cells, tissues and animals, especially humans. In one embodiment, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

In one embodiment, the oligonucleotides used in the methods and compositions described herein, are synthetic peptide nucleic acids (PNAs) which interact with the nucleotide sequence encoding Atp6v0d2, comprising SEQ. ID No.'s 1-4 including variant or fragments thereof in a sequence-specific manner and silence function of Atp6v0d2. In another embodiment, the oligonucleotides used in the methods and compositions described herein, are locked nucleic acid (LNA), which interact with the nucleotide sequence encoding Atp6v0d2, comprising SEQ. ID No.'s 1-4 including variant or fragments thereof, forming a LNA/DNA co-polymer, in a sequence-specific manner and substantially silence the function of Atp6v0d2.

In one embodiment, the term "locked nucleic acid" (LNA) refers to a synthetic nucleic acid analogue, incorporating "internally bridged" nucleoside analogues. Synthesis of LNA, and properties thereof, have been described by a number of authors: Nielsen et al, (1997 J. Chem. Soc. Perkin Trans. 1, 3423); Koshkin et al, (1998 Tetrahedron Letters 39, 4381); Singh & Wengel (1998 Chem. Commun 1247); and Singh et al, (1998 Chem. Commun. 455). As with PNA, LNA exhibits in certain embodiments, greater thermal stability when paired with DNA, than do conventional DNA/DNA heteroduplexes. In one embodiment, LNA can be joined to DNA molecules by conventional techniques. Therefore, in one embodiment, LNA is to be preferred over PNA, for use in the agents of the methods and compositions described herein.

In one embodiment, the target specific regions of the agent that is able to inhibit gene function, such as the Atp6v0d2 gene including variant or fragments thereof, may comprise LNA and/or PNA and the arm region comprise DNA, with the agent further comprising a destabilizing moiety.

In another embodiment, the agent capable of inhibiting expression or function of Atp6v0d2 gene, or its encoded protein is an agPNA. In another embodiment, this antibody is referred to as antigenic PNA.

In one embodiment, inhibiting function of Atp6v0d2 in the methods described herein, comprises administering to the subject an agent able to inhibit the function of a OCL-2A3. In another embodiment, that agent is an antibody as described hereinabove. In one embodiment, the antibody is polyclonal or monoclonal antibody, or a functional fragment thereof, such as Fab, a Fab', and a $F(ab')_2$ in certain embodiments, which is specific against OCL-2A3.

In one embodiment, the agents described herein, are used in the methods described hereinbelow.

In another embodiment, provided herein is a method of inhibiting bone resorption in a subject, comprising administering to said subject and agent capable of inhibiting the expression or function of a gene encoding OCL-2A3, thereby inhibiting osteoclast cell-to-cell fusion or osteoclast maturation. As used herein, the term "bone resorption" refers to the undesired loss of bone caused at least in part by osteoclast activity. In another embodiment, the term "inhibit" refers to a decrease the amount, quality, or effect of a particular activity and is used interchangeably with the terms "reduce", "minimize", and "lessen" and refers to, in other embodiments, the reduction of expression or function of Atp6v0d2 by the administration of a therapeutically effective amount of the agents and compositions described herein to a patient, using the methods described herein.

In one embodiment, the term "therapeutically effective amount" refers to an amount of a compound which produces a medicinal effect observed as reduction in the rate of bone loss in an individual, or in another embodiment, increase in bone formation (both as measured in density or rate) when a therapeutically effective amount of an agent or compositions as described herein, is administered to an individual who is susceptible to or suffering from a disease characterized by bone loss. Therapeutically effective amounts are typically determined by the effect they have compared to the effect observed when a composition which includes no active ingredient (i.e. a control) is administered to a similarly situated individual. In another embodiment, the term "diseases characterized by bone loss refers to diseases, conditions, disorders and syndromes which have as a symptom or pathology a decrease in bone mass or density.

Theses diseases are Osteoporosis, Rickets, osteomalacia, renal osteodystrophy, Paget's disease of the bone, osteogenesis imperfecta (OI), osteosarcoma, Ewing's sarcoma, multiple myeloma, metastatic breast and prostate cancer, oral bone loss, osteopenia, rheumatoid arthritis (RA), osteoarthritis (OA), or a combination thereof.

In one embodiment, the term "treatment", or "treating" refers to any process, action, application, therapy, or the like, wherein a subject, including a human being, is subjected to medical aid with the object of improving the subject's condition, directly or indirectly. The term "treating" refers also to reducing incidence, or alleviating symptoms, eliminating recurrence, preventing recurrence, preventing incidence, improving symptoms, improving prognosis or combination thereof in other embodiments. "Treating" embraces in another embodiment, the amelioration of an existing condition. The skilled artisan would understand that treatment does not necessarily result in the complete absence or removal of symptoms. Treatment also embraces palliative effects: that is, those that reduce the likelihood of a subsequent pathology. The alleviation of a condition that results in a more serious condition is encompassed by this term. Therefore, in one embodiment, provided herein a method of treating a pathology, such as osteoporosis in another embodiment; associated with increased bone resorption, decreased bone formation or acombination thereof, in a human subject, administering to said subject an effective amount of a composition comprising an agent able to inhibit the expression or function of a gene encoding OCL-2A3 in the subject, thereby to inhibiting bone resorption, increasing bone formation or a combination thereof and treating a pathology associated with increased bone resorption, decreased bone formation or acombination thereof.

The mineralisation of osteoid tissue of bone is dependent on a suitable supply of mineral, both calcium and phosphate, to that tissue. "Rickets", refers in one embodiment to circumstances where there is failure to provide sufficient mineral resulting in osteomalacia in growing bone with its attendant growth plates and unfused epiphyses. In one embodiment, the methods described herein are used to treat Rickets.

When poor renal function leads to low blood calcium; as the kidney is responsible for both vitamin D metabolism and calcium reabsorption from the glomerular filtrate, the calcium harbored in bones must therefore liberated by increased parathyroid hormone levels to maintain blood calcium concentrations. In circumstances where renal disfunction prevents calcium readsorption, renal osteodystrophy results (ROD). In another embodiment, the agents, compositions and methods described herein are utilized in the treatment of ROD.

In one embodiment, Osteogenesis Imperfecta (OI) refers to a genetic disorder characterized by the causation of several bone fractures and deformities. It affects children since birth, hindering their normal growth and skeletal development. Osteogenesis imperfecta (OI) is a heterogeneous group of heritable connective tissue disorders characterized by fragile and brittle bones, blue sclera, dental malformations, deafness, and hyperextensible ligaments. In one embodiment, bone fragility in OI patients is affected by I) the bone remodeling process resulting in increased bone turnover. In doing so, OI worsens the calcium metabolic state, resulting in Osteopenia, thereby exacerbating bone deformation, or II) the defective muscular development hinders the main physiological stimulus for the architectural development of bones, fostering formation of bone structures that is incapable of bearing load. In another embodiment, bone disorder caused by Osteogenesis Imperfecta is qualitative as well as quantitative, where both the mineralization and conformation of the bone are insufficient to withstand load bearing, resulting in deformations and fractures. In one embodiment, the agents and compositions described herein, are useful in readjusting the bone remodeling process, resulting in decreased bone readsorption and increased bone formation, thereby enabeling load bearing bones.

In one embodiment, the osteoporosis treated using the agents and compositions described herein, utilizing the methods described herein, is primary osteoporosis, idiopathic osteoporosis, age-related osteoporosis, secondary osteoporosis or a combination thereof. In another embodiment, the osteoporosis is associated with idiopathic hyper-calciuria, cystic fibrosis, thyrotoxicosis, celiac, Crohn's disease, ulcerative colitis, Rickets, osteomalacia, renal osteodystrophy, Paget's disease of the bone, osteogenesis imperfecta (OI), osteosarcoma, Ewing's sarcoma, multiple myeloma, metastatic breast and prostate cancer, oral bone loss, osteopenia, rheumatoid arthritis (RA), osteoarthritis (OA), or a combination thereof. In one embodiment, the agents identified by the methods described herein that are used in the compositions described herein for the methods described herein are effective in treating pathologies where bone remodeling is affected by other physiological events and their ensuing pathologies, that result in increased bone resorption and decreased bone formation.

In one embodiment, the physiological events and their ensuing pathologies, that result in increased bone resorption and decreased bone formation are described hereinabove.

Paget disease of bone (PD), the second most common bone disease behind osteoporosis refers in one embodiment, to the a pathology whereby focal regions of excessive bone remodeling, with abnormalities in all phases of the bone remodeling process. Subjects having PD, exhibit or experience in another embodiment pain, or skeletal deformity, neurologic symptoms, pathologic fractures, or deafness in other embodiments. In one embodiment, a subject has one affected bone or have pagetic lesions in multiple bones in another embodiment. PD remains mostly localized, and new lesions in previously unaffected bones after diagnosis seldom develop. In certain embodiments, osteosarcoma develops in the pagetic bone. The initial phase of PD is characterized in one embodiment, by excessive bone resorption in a focal region, and the development of osteolytic lesions. In one embodiment, osteoclasts in pagetic lesions are increased in number, size and in cross-section; are seen to contain up to 100 nuclei, in contrast to normal osteoclasts, which contain 3-20 nuclei.

In one embodiment, provided herein is a method of treating early stage Paget's disease in a subject, comprising administering to the subject, in a focal region of excessive bone resorption, an agent capable of inhibiting the expression or function of Atp6v0d2, thereby arresting bone resorption in the focal region, diminish the nuclei number and size of to osteoclasts and prevents osteoclasts fusion.

In one embodiment, provided herein is a method of inhibiting osteoclast cell fusion, comprising the step of contacting the osteoclast cell with an agent able to inhibit the expression or function of a gene encoding OCL-2A3 in the subject, thereby downregulating the expression of ADAM protein's mRNA. A DAM (a disintegrin and metalloprotease) molecules refers in one embodiment to a family of membrane anchored cell surface glycoproteins. ADAM Proteins have a unique domain organisation, comprising (from the N-terminus to the C-terminus) a prodomain, metalloprotease domain, disintegrin domain, cysteine rich domain, transmembrane domain, and cytoplasmic domain. In one embodiment, owing to their structural features, ADAMs are involved in proteolysis, cell adhesion, cell fusion, and signalling. In another embodiment, only bone, which contains multinucleated osteoclasts, expresses ADAM12 (meltrin-α). In another embodiment, ADAM12 has fusogenic properties and plays a role in the formation of myotubes by the fusion myoblasts. In one embodiment, high expression of ADAM12 in adult bone indicates that ADAM12 is involved in the formation of multinucleated osteoclasts by the fusion of mononuclear stromal cells. In another embodiment, ADAM8 is an autocrine-paracrine factor, regulating OCL activity. ADAM8 is in another embodiment, an active metalloprotease, hydrolyzing a variety of peptide substrates based on the cleavage sites of membrane-bound cytokines, growth factors, and receptors, such as in one embodiment, those responsible for OCL growth and maturation. In one embodiment, the agents identified using the methods of the invention, or other agents described herein, utilized in the compositions described herein and which are used in the methods described herein, result in the downregulation of ADAM8 and ADAM12 mRNA.

In one embodiment, provided herein is a transgenic mouse and progeny thereof whose genome comprises a nucleic acid which does not encode murine OCL-2A3, or in another embodiment, a transgenic mouse and progeny thereof whose genome comprises a nucleic acid which does encode murine or human OCL-2A3. In another embodiment, the transgenic mouse is fertile and transmits the transgene to its offspring.

Mice are used in one embodiment for transgenic animal models because they are easy to house, relatively inexpensive, and easy to breed. However, other non-human transgenic mammals may also be made in accordance with the present invention and in certain embodiments, such as monkeys, sheep, rabbits or rats. In one embodiment, transgenic animals refer to those animals that carry a transgene, which is a cloned gene introduced and stably incorporated, which is passed on in another embodiment, to successive generations. In an embodiment of the present invention, the Atp6v0d2 gene was cloned and stably incorporated into the genome of a mouse. Alternatively, altered portions of the Atp6v0d2 gene sequence may be used in other embodiments. In this manner, the specific function of alternatively spliced gene products may be investigated during animal development and initiation of disease states in order to develop therapeutic strategies or to identify biologically active agents to be used in the methods described herein, or in the compositions described herein.

To create a transgenic mouse, an altered version of the human gene of interest is inserted in one embodiment, into a mouse germ line using standard techniques of oocyte microinjection or transfection or microinjection into stem cells. In another embodiment, if it is desired to inactivate or replace the endogenous gene, homologous recombination using embryonic stem cells may be applied.

For oocyte injection, one or more copies of the human or murine Atp6v0d2 gene sequence can be inserted into the pronucleus of a just-fertilized mouse oocyte. This oocyte is then reimplanted into a pseudo-pregnant foster mother. The liveborn mice can then be screened for integrants using analysis of tail DNA for the presence of the Atp6v0d2 gene sequences, using in another embodiment, the sequences set forth in SEQ ID NO.'s 1-4. The transgene can be either a complete genomic sequence injected as a YAC or chromosome fragment, a cDNA with either the natural promoter or a heterologous promoter, or a minigene containing all of the coding region and other elements found to be necessary for optimum expression.

Retroviral infection of early embryos can also be done to insert the altered gene. In this method, the altered gene is inserted into a retroviral vector which is used to directly infect mouse embryos during the early stages of development to generate a chimera, some of which will lead to germline transmission (Jaenisch, R. 1976. Proc. Natl. Acad. Sci. USA, 73: 1260-1264, which is incorporated herein by reference in its entirety).

In one embodiment, "transfection" refers to a cell that has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary or other cell that is capable of stable growth in vitro for many generations. An organism, such as a plant or animal, that has been transformed with exogenous DNA is termed "transgenic", such as, in one embodiment, the transgenic mouse described herein.

One skilled in the art would readily comprehend that the nucleic acid construct of certain embodiments of the present invention may contain, any suitable nucleic acid sequence which encodes for Atp6v0d2 gene. Such nucleic acid sequence is in another embodiment, the full-length Atp6v0d2 cDNA or may encompass other variants or derivatives of such sequence so long as Atp6v0d2 gene is expressed in other embodiments. Nucleic acid variants are those that comprise in one embodiment, a sequence substantially different from Atp6v0d2 cDNA sequence but that, due to the degeneracy of the genetic code, still encode Atp6v0d2. The variants may be variants made in another embodiment, by recombinant methods such as in one embodiment, mutagenesis techniques. Such nucleic acid variants include in one embodiment, those produced by nucleotide substitutions, deletions or additions. The substitutions, deletions or additions may involve in another embodiment, one or more nucleotides. Alterations in the coding regions may produce in one embodiment, conservative or nonconservative amino acid substitutions, deletions or additions. In one embodiment these substitutions, deletions or additions are silent substitutions, additions and deletions which do not alter the properties and activities of Atp6v0d2 gene. Nucleotide changes present in a variant polynucleotide are silent in one embodiment, which means in another embodiment, that they do not alter the amino acids encoded by the polynucleotide One skilled in the art would also understand that Atp6v0d2 gene may be obtained by a wide variety of techniques that include, but are not limited to, isolation from genomic sources, preparation of cDNAs from isolated mRNA templates, direct synthesis, or a combination thereof. These techniques are well known to those of skill in the art. Furthermore, Atp6v0d2 gene has been previously described and characterized and therefore one skilled in the art would readily comprehend what gene and sequence is encompassed by reference to the "Atp6v0d2" gene. The nucleic acid construct of the present invention include in one embodiment, a regulatory element in order to enhance the expression of Atp6v0d2 transgene.

A transgenic animal carrying one transgene can be further bred to another transgenic animal carrying a second transgenes to create a so-called "double transgenic" animal carrying two transgenes. In one embodiment the invention relates to non-human transgenic animals having a transgene comprising a polynucleotide sequence encoding a Atp6v0d2 of the invention or in another embodiment, having an additional transgene encoding a gene of interest operably linked to a Atp6v0d2 responsive promoter. In one embodiment, the double transgenic mouse of the invention further comprises a polynucleotide sequence, encoding a gene or in another embodiment, a protein of interest, which in one embodiment encodes a gene encoding a detectible marker or a detectible protein. Double transgenic animals having both transgenes (i.e., a Atp6v0d2 transgene and a gene of interest linked to a Atp6v0d2-responsive promoter) are also encompassed by the invention.

In another embodiment, provided herein is a method for identifying in vivo a biological activity of a compound, said method comprising the steps of: providing a transgenic mouse whose genome does not express Atp6v0d2 gene; administering said compound to said mouse; determining an expressed pathology of said mouse; and identifying a in vivo biological activity of said compound.

The compounds referred to can be of any type, including in one embodiment, nucleic acid, polypeptide or other organic molecule. The present invention extends in various aspects to a pharmaceutical composition, medicament, drug or other composition comprising such a compound, a method comprising administration of such a composition, a method comprising administration of such a composition to a patient, e.g., for treatment of bone remodeling and bone formation disorders and pathologies, use of such a compound in the manufacture of a composition for administration, e.g., for treatment of bone remodeling and bone formation disorders and pathologies, and a method of making a pharmaceutical composition comprising admixing such a compound with a pharmaceutically acceptable excipient, vehicle or carrier, and optionally other ingredients.

In the case of transgenic animals, the evaluation of the potentially useful compound for the treatment or prevention of bone remodeling and bone formation disorders and pathologies, can be performed in one embodiment, by administration of the compound to be tested to said transgenic animal, at different doses, and evaluating the physiological response of the animal over time. In another embodiment, the administration of the compound to be assayed can be oral or parenteral, depending on the chemical nature of the compound to be evaluated. In one embodiment, it may be appropriate to administer the compound in question along with cofactors that enhance the effect of the compound.

In another embodiment, provided herein is a method for identifying in vivo a biological activity of a compound, said method comprising the steps of: providing a transgenic mouse whose genome does express murine or human Atp6v0d2 gene; administering said compound to said mouse; determining an expressed pathology of said mouse; and identifying a in vivo biological activity of said compound.

The progeny of a non-human transgenic mammal provided by this invention, such as the progeny of a transgenic mouse described herein can be obtained in one embodiment, by copulation of the transgenic animal with an appropriate individual, or by in vitro fertilization of eggs and/or sperm of the transgenic animals. In another embodiment, the term "progeny" or "progeny of a non-human transgenic mammal" relates to all descendents of a previous generation of the non-human transgenic mammals originally transformed. The progeny can be analysed to detect the presence of the transgene by any of the aforementioned methods.

In one embodiment, the compositions described herein may use the compounds which biological activity was evaluated using the transgenic mice described herein.

In one embodiment, provided herein is a method of enhancing bone formation in a subject, comprising the step of inhibiting OCL-2A3 expression or function in said subject, thereby increasing osteoblast numbers, enhancing anabolic activity of osteoblasts, increasing new bone formation, or combination thereof. In one embodiment, inhibiting the expression or function of OCL-2A3 is done by any of the aforementioned embodiments resulting in the inhibition of the expression or function of OCL-2A3 or Atp6v0d2 in another embodiment.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Materials and Methods:
Targeted Disruption of the Atp6v0d2 Gene

The targeting vector was constructed from pPNT to replace the 330 bp fragment containing exon 1 (a.a. 1-43) of Atp6v0d2 by standard procedures, essentially as described. Flanking homologous genomic DNA was amplified from DNA of E14.1 ES cells by PCR. The linearized targeting constructs were electroporated into E14.1 ES cells, selected by G418 and gancyclovir, as described. Atp6v0d2$^{+/null}$ ES clones were identified by PCR and Southern blot analyses (FIG. 1), then injected into C57BL/6J blastocysts to yield chimeric mice that were subsequently crossed with C57BL/6 mice to yield Atp6v0d2$^{+/-}$ mice. Mice were on a B6/129 background.

RNA and Protein Analysis

RNA was isolated using Trizol (Invitrogen) and subjected to northern blot analysis using the 5'-terminal 440 bp of Atp6v0d2 cDNA and the Atp6v0d1 cDNA for open reading frame, respectively. Real-time PCR was performed using the TaqMan universal PCRmaster mix on an ABI Prism 7000 Sequence Detection System (Applied Biosystems). Taqman primers for indicated genes were from Applied Biosystems. 250 ng of cDNA template generated using SuperScript II (Invitrogen) was used for each reaction. For western blot analysis, equal amounts of cell lysates were subjected to analysis with rabbit polyclonal antibody specific for Atp6v0d2 or anti-FLAG mAb (Sigma). Rabbit anti-Atp6v0d2 polyclonal Abs were raised against Atp6v0d2 peptide (334-350 amino acids, used after purification on the affinity column containing the immunogenic peptide). Specificity was confirmed by the lack of cross-reaction to murine Atp6v0d1 overexpressed in 293 cells.

Histological and Morphometric Analyses

Histological sections (5 μm) were stained with haematoxylin and eosin or for TRAP activity. Isolated bones were evaluated using a desktop μCT imaging system (μCT40; Scanco Medical AG)21. Morphometric parameters were computed using direct 3D approach that does not rely on any assumptions about the underlying bone structure. Differences were considered significant at $p<0.05$.

Osteoclast Formation, F-Actin Staining and Pit Formation

Osteoclasts were prepared from bone-marrow cells using the two standard methods. TRAP assays, F-actin staining, and pit formation were also carried out.

Retrovirus Preparation and Infection

Flag epitope tagged cDNAs for Atp6v0d2 and meltrin-α were cloned into pMX-puro, transfected into PLAT-E cells to generate retroviruses that were used to infect BMMs. Briefly, BMMs were derived by culturing bone-marrow cells (1×10$^7$ cells/dish) for 2 days in the presence of M-CSF (120 ng/ml), using Corning 100 mm suspension dishes (Corning Incorporated Life Science), and incubated with retroviruses in media containing M-CSF (120 ng/ml) and polybrene (5 µg/ml) for 6 h. After washing, BMMs were cultured overnight, detached with Trypsin/EDTA and further cultured with M-CSF (120 ng/ml) and puromycin (2 µg/ml) for 2 days. Puromycin-resistant BMMs were induced to differentiate with M-CSF (30 ng/ml) and TRANCE (150 ng/ml) for an additional 4-5 days.

Preparation of Pre-Osteoclasts and Fusion

Preparation of Mononuclear Pre-Osteoclasts and Subsequent Induction of fusion were performed. In brief, mononuclear pre-osteoclasts were prepared by co-culturing BM cells ($2 \times 10^7$ cells/dish) with calvarial osteoblasts ($2 \times 10^6$ cells/dish) for 6 days in media supplemented with $10^{-8}$ M 1α, 25(OH)$_2$D$_3$ and $10^{-6}$ M PGE$_2$. After removal of floating cells, mononuclear cells were harvested from attached cells by gentle pipetting. TRAP$^+$ mononuclear pre-osteoclasts constituted more than 40-50% of the total cells harvested, and no multinucleated cells were detected. Based on alkaline phosphatase staining, no osteoblasts were detected. To induce fusion, purified mononuclear cells ($1 \times 10^5$ cells/well, 200 µl/well, 96 well plates) were cultured with MCSF (30 ng/ml) and TRANCE (150 ng/ml) for 24 h. Cells were then stained for F-Actin and TRAP, and bone resorption assays were performed, as described above. When trans-well plates were employed, F-actin and TRAP staining were performed on cells in lower wells, since osteoclasts are formed only in lower wells. For heterotypic fusion, pre-osteoclasts from wild-type and Atp6v0d2$^{-/-}$ mice were incubated with Vybrant cell labeling dyes, D$_i$O and D$_i$D (5 µg/ml, Molecular Probes), respectively, for 15 min. After washing, stained wild-type and mutant pre-osteoclasts were mixed at equal numbers and cultured on glass cover discs for 24 h under TRANCE and M-CSF treatment. Cells were then examined using Zeiss Axioplan II fluorescence microscope (Zeiss, Thornwood, N.Y.).

Statistical Analysis

Data are expressed as the mean±standard deviation (s.d) or standard error (s.e.m) of the mean, as indicated, from at least three independent experiments for each experimental condition. Unless stated otherwise, statistical analysis was performed by the two-tailed Student's t-test to analyze differences between groups.

Example 1

OCL-2A3 is Atp6v0d2

Figure 5:
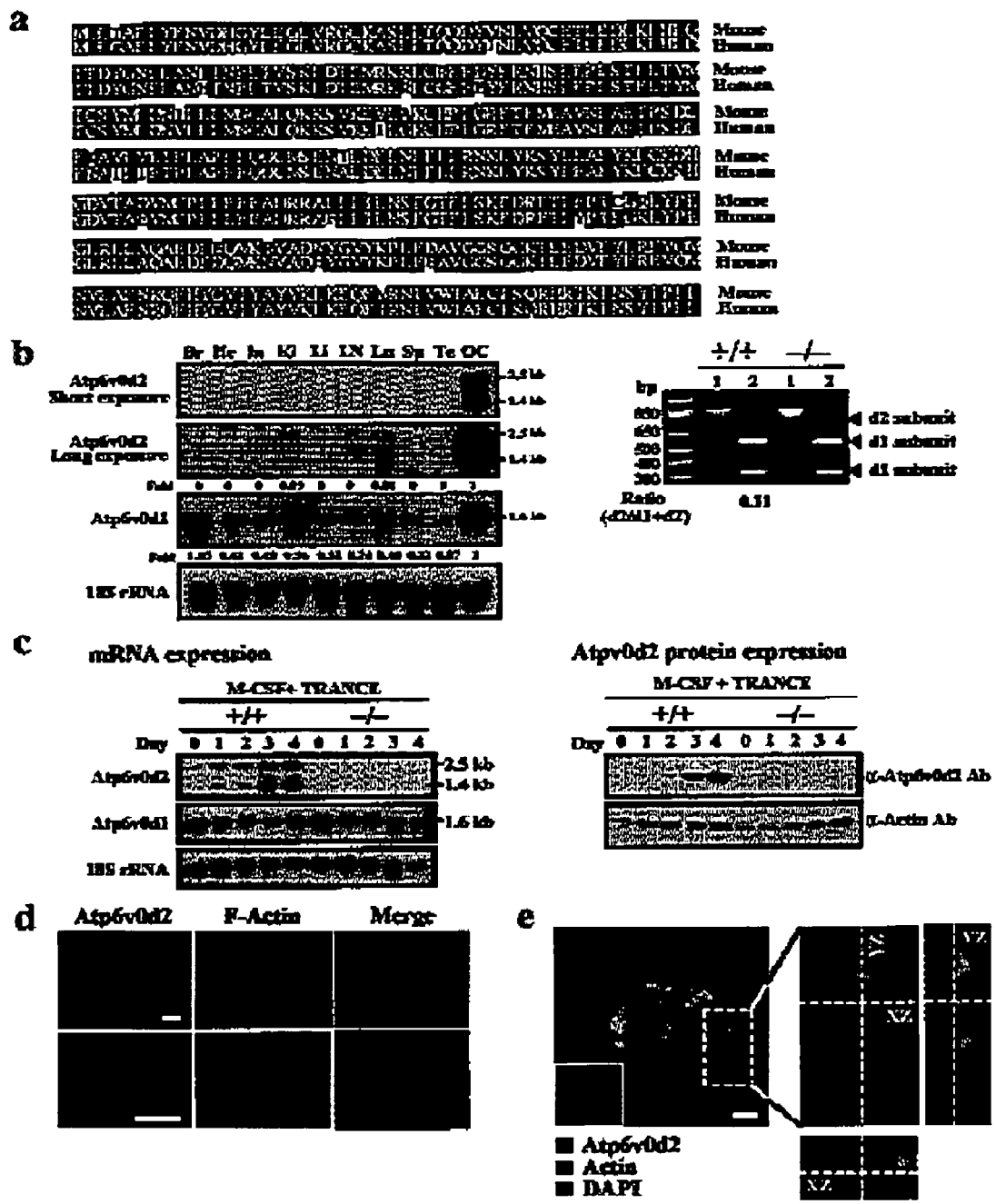
FIG. 5 shows (a) Mouse and human Atp6v0d2 amino acid sequences, identified in this study, are shown. (*) indicates the difference from the published sequences (accession number NP_780615 (SEQ ID NO: 13) for mouse, NP_689778 for human (SEQ ID NO: 14), in which phenylalanine is substituted to isoleucine. (b) (left) Total RNA was isolated and analyzed for Atp6v0d2 and Atp6v0d1 mRNA by northern blot. Two transcripts (approximately 2.5 kb and 1.4 kb) were detected for Atp6v0d2. Relative mRNA expression level was then quantitated with the NIH imaging program (NIH Image 1.62) and normalized to that of 18S rRNA. (right) RT-PCR-based comparison of Atp6v0d1 and Atp6v02 mRNA expression level. To compare an expression level between Atp6v0d1 and Atp6v02, total RNA was isolated from Atp6v0d2−/− and wild-type OCs treated with TRANCE and M-CSF for 4 days using Trizol (Invitrogen). cDNA was generated using SuperScript II (Invitrogen). To alleviate amplification rate difference, c-DNA was first amplified with primer set common for both Atp6v0d1 and Atp6v0d2 (forward primer: 5'-TATG-GCAACTTCCTGGC-3' (SEQ ID NO. 17), Reverse primer: 5'-GCATAAAA(C/G)ACACCA(A/T)AATGGA-3' (SEQ ID NO. 18)). The PCR products were then digested with Pst I restriction enzyme. Atp6v0d1 produced 281 by and 507 by fragments and Atp6v0d2 showed an uncut 788 by fragment. Relative expression level of these fragments was then quantitated with the NIH imaging program (NIH Image 1.62), and used for calculation. (c) Induction of Atp6v0d2 mRNA and protein expression during osteoclast differentiation. BMMs from wild-type and Atp6v0d2−/− mice were treated with M-CSF (30 ng/ml) and TRANCE (150 ng/ml) for 4 days. Total RNA was isolated each day after treatment. Expression of Atp6v0d2 and Atp6v0d1 was determined by northern blot and western analysis. (+/+) wild-type cells, (−/−) Atp6v0d2-deficient cells. (d) Localization of Atp6v0d2 in mature osteoclasts was detected by immunostaining with rabbit anti-Atp6v0d2 polyclonal Ab together with rhodamine-phalloidin for F-actin staining. Overlaid images are shown (merge). The confocal images depict 0.25 μm optical sections. Scale bar indicates 25 μm. (e) Osteoclasts were generated on dentine slices, stained for Atp6v0d2 and F-actin, and analyzed by confocal microscopy. Confocal z-sections were reconstructed as orthogonal view by sections. Boxed area represents one of image plane among z-sections. The localization of Atp6v0d2 and F-Actin was shown by the vertical orthogonal image (YZ) and horizontal orthogonal image (XZ) over dotted line in zoomed area. The inlet shows Atp6v0d2 localization of mononuclear pre-osteoclast (pOC) on dentine slice. The Atp6v0d2 shows even distribution in cytosol of pOC. The images were captured every 0.25 μm distance. Scale bar indicates 25 μm. For (d) and (e), an Olympus Fluoview 1000 laser confocal imaging system (Olympus) and an Olympus IX60 inverted microscope with a 60× oil immersion objective for (d), and 40× or 20× water immersion objectives was used for (e).

Mature osteoclasts possess properties not found in other monocyte-derived cells, despite their shared origin. To understand how osteoclasts differ from macrophages or dendritic cells, comparative mRNA expression profile analyses were previously employed and a cDNA fragment for a novel v-ATPase d subunit homolog was identified, which is highly enriched in osteoclasts. Full-length cDNA analysis shows that the gene encoding OCL-2A3 encodes proteins identical to the recently reported v-ATPase subunit d2 (Atp6v0d2), except for one amino acid residue (FIG. 5). In contrast to previous reports, it is found that the Atp6v0d2 gene produces two transcripts, ~2.5 and ~1.4 kb, which differ only in the 3' untranslated region. Atp6v0d2 expression is highly upregulated during osteoclast differentiation and is most abundant in mature osteoclasts, where it is preferentially found in the plasma membrane region surrounded by the actin ring (FIG. 5).

Example 2

Structure of Atp6v0d2 and its Organization within v-ATPase Complex

The v-ATPase complex is organized into a peripheral V1 domain, composed of eight subunits (A to H) for ATP hydrolysis, and a membrane integral V0 domain, containing five subunits (a, d, c, c', and c") for proton translocation. Multiple isoforms of v-ATPase subunits have been identified that show distinct cell-type and tissue-specific expressions, and these isoforms are proposed to account for diverse physiological properties of ubiquitous v-ATPases in distinct cell types. Two isoforms of v-ATPase V0 subunit d; d1 and d2, have been identified in mouse and human. Although Atp6v0d2 is structurally homologous to the Atp6v0d1, the functional importance of Atp6v0d2 was unknown.

Figure 6:
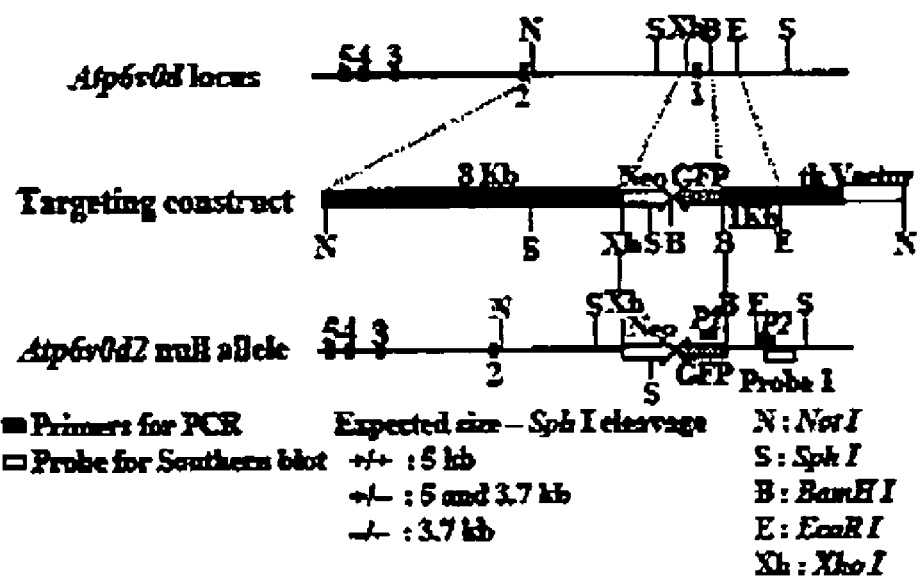
FIG. 6 shows Strategy of Atp6v0d2 disruption. PCR primers for mutant screening (P1 and P2) and probe for Southern analysis (Probe 1) are indicated. Exon 1, containing the start codon, was replaced with the Neo-GFP cassette to yield the Atp6v0d2 null allele.
Figure 7:
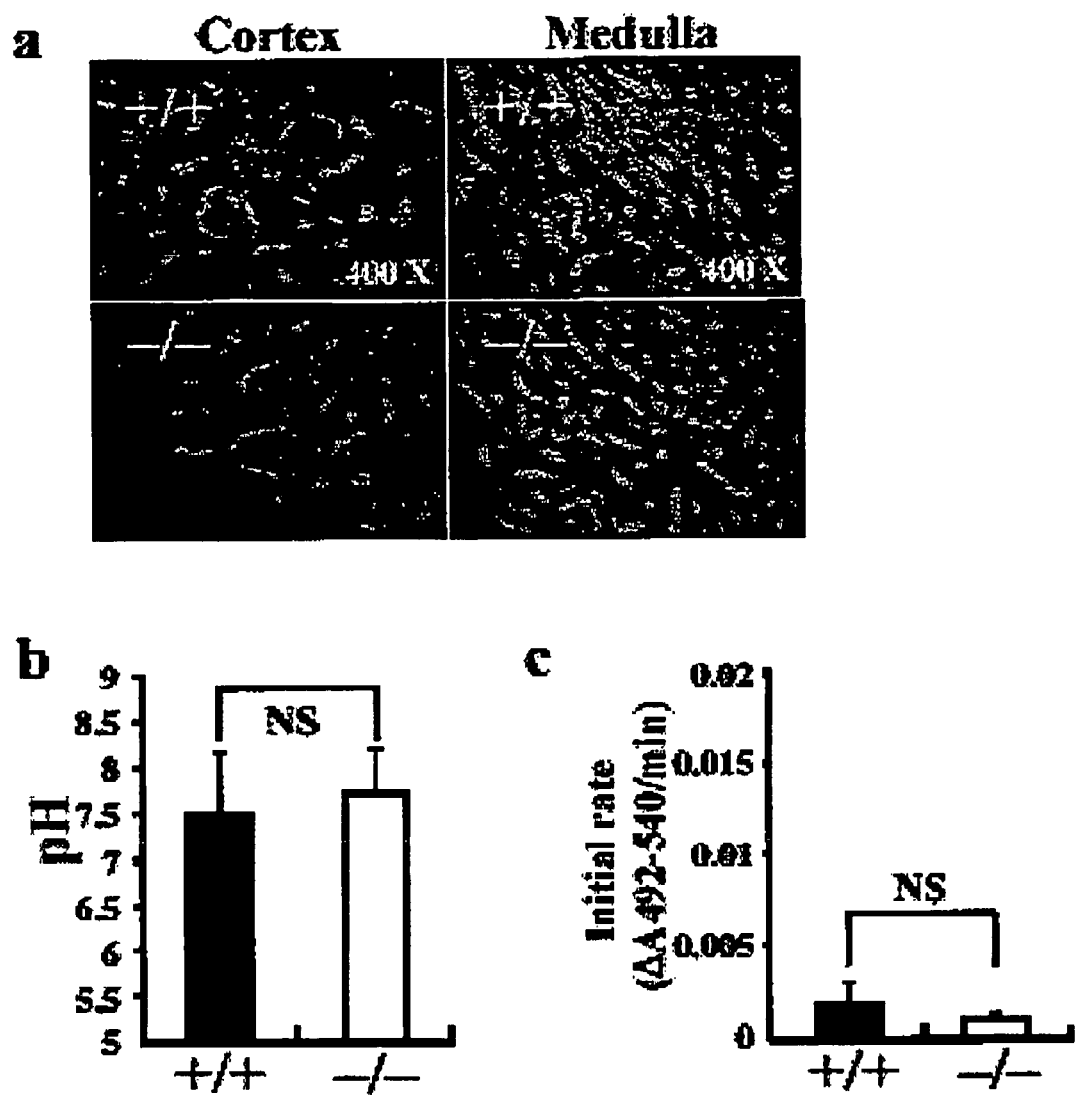
FIG. 7 shows that deficiency of Atp6v0d2 does not affect function of the kidney. (a) Kidneys from wild-type and Atp6v0d2−/− mice were fixed in 10% formalin and subjected to histology. Kidney sections (5 μm) were stained with haematoxylin and eosin according to standard procedures, and morphology of the cortex and medulla were compared between wild-type and mutant. (b) pH in urine from wild-type and Atp6v0d2−/− mice (n=6) was measured. (c) Proton transport assay was performed with microsomal preparations derived from wild-type and Atp6v0d2−/− mouse kidney. Proton transport was monitored as change of absorbance caused by quenching of acridine orange and expressed by initial rate (ΔA492-540/min) Data are mean±s.d. from five experiments. NS, not significant.

To define the function of Atp6v0d2, Atp6v0d2-deficient mice were generated by targeted disruption of exon 1 of Atp6v0d2 (FIG. 6). Northern and western blot analysis confirmed the lack of Atp6v0d2 mRNA and protein expression in Atp6v0d2$^{-/-}$ mice (FIG. 1a). Atp6v0d2$^{-/-}$ mice were born at the expected Mendelian ratio and exhibited normal growth rates, without overt defects. The level of Atp6v0d2 mRNA is extremely low compared to other isoforms. For example, it is at least 10 fold lower than that of d1 subunit in osteoclasts, and at least 200 fold lower than d1 in other tissues (FIG. 5). Consistently, brain, heart, lung, liver, spleen and intestine, appear normal in Atp6v0d2$^{-/-}$ mice. In addition, the kidney of Atp6v0d2$^{-/-}$ mice showed no histological defects, and normal v-ATPase function and subsequent regulation of urinary pH (Supplementary Fig. S3).

Example 3

Atp6v0d2 Deficiency Results in Increased Bone Formation Rate and Decreased Bone Resorption To determine the impact of Atp6v0d2 deficiency on bone, femurs, tibias and vertebrae (L1) were isolated from age and sex-matched, wild-type littermates and Atp6v0d2$^{-/-}$ mice. High-resolution microcomputed tomography (µCT) show significant increases in bone mass and concomitant decreases in bone marrow cavity space in the absence of Atp6v0d2 (FIG. 1b and Table 1). Bone sections stained for tartrate-resistant acid phosphatase (TRAP) revealed the reduced osteoclast surface area (OcS/BS) in Atp6v0d2$^{-/-}$ mice compared to control littermates (FIG. 1c and Supplementary Table S2). However, the number of TRAP(+) cells (NOc/Bpm) in Atp6v0d2$^{-/-}$ bones appears to be comparable to those in control littermate bones (FIG. 1c and Supplementary Table S2). These results suggest that osteoclast maturation/function, rather than differentiation might be affected in Atp6v0d2$^{-/-}$ mice. Consistently, serum TRAP5b levels were comparable in Atp6v0d2$^{-/-}$ and control littermates (FIG. 1d). Defects of osteoclasts in Atp6v0d2$^{-/-}$ mice are also supported by the presence of increased cartilage remnants and reduced serum carboxy-terminal collagen crosslinks (FIG. 1e, f). These results indicate that increased bone mass in Atp6v0d2$^{-/-}$ mice is in part due to defective bone resorption.

TABLE I

Structural Parameters measured by Microcomputed Tomography

| | Mice | No. of mice | BV/TV (%) | Tb. N. (N/mm) | Tb. Th. (μm) | Tb. Sp. (μm) | Conn-Dens (1/mm$^3$) | Cortical thickness (mm) | Cortical Bone area (mm$^2$) |
|---|---|---|---|---|---|---|---|---|---|
| Femur | WT | 6 | 12.3 ± 0.62 | 5.24 ± 0.208 | 43 ± 0.11 | 192 ± 7.4 | 133 ± 21.9 | 0.184 ± 0.009 | 0.74 ± 0.053 |
| | KO | 6 | 18.4 ± 1.98* | 7.04 ± 0.371* | 43 ± 2.47 | 138 ± 9.5* | 296 ± 44.5* | 0.214 ± 0.010* | 0.83 ± 0.056 |
| Tibia | WT | 8 | 11.1 ± 1.17 | 5.99 ± 0.283 | 39 ± 1.06 | 167 ± 8.1 | 107 ± 23.0 | 0.226 ± 0.005 | 0.59 ± 0.022 |
| | KO | 8 | 19.9 ± 3.22* | 8.02 ± 0.371* | 41 ± 2.12 | 121 ± 7.1* | 305 ± 45.6* | 0.238 ± 0.007 | 0.63 ± 0.030 |
| Vertebrae | WT | 8 | 18.1 ± 1.13 | 5.54 ± 0.145 | 41 ± 0.71 | 179 ± 4.9 | 270 ± 17.3 | | |
| (L1) | KO | 8 | 34.0 ± 1.77* | 7.03 ± 0.187* | 52 ± 1.41* | 135 ± 4.2* | 345 ± 18.0* | | |

*p < 0.05 (Only the columns marked with * show statistical differences)

Unexpectedly, Atp6v0d2$^{-/-}$ mice also exhibited dramatic increase in osteoblast area (ObS/BS) as well as bone formation rate (MAR, BFR/BS) (FIG. 1c, g). Atp6v0d2 is not detected in osteoblasts. In addition, Atp6v0d2 deletion did not affect anabolic osteoblast differentiation as well as expression of osteoblast differentiation markers such as Dlx5, Osx or RUNX2 in vitro (FIG. 8). Thus increased osteoblast activity in Atp6v0d2$^{-/-}$ mice is likely due to osteoblast-extrinsic factors—possibly mutant osteoclasts.

Example 4

Atp6v0d2 Regulates the Formation of Large Multinucleated Cells

Figure 2:
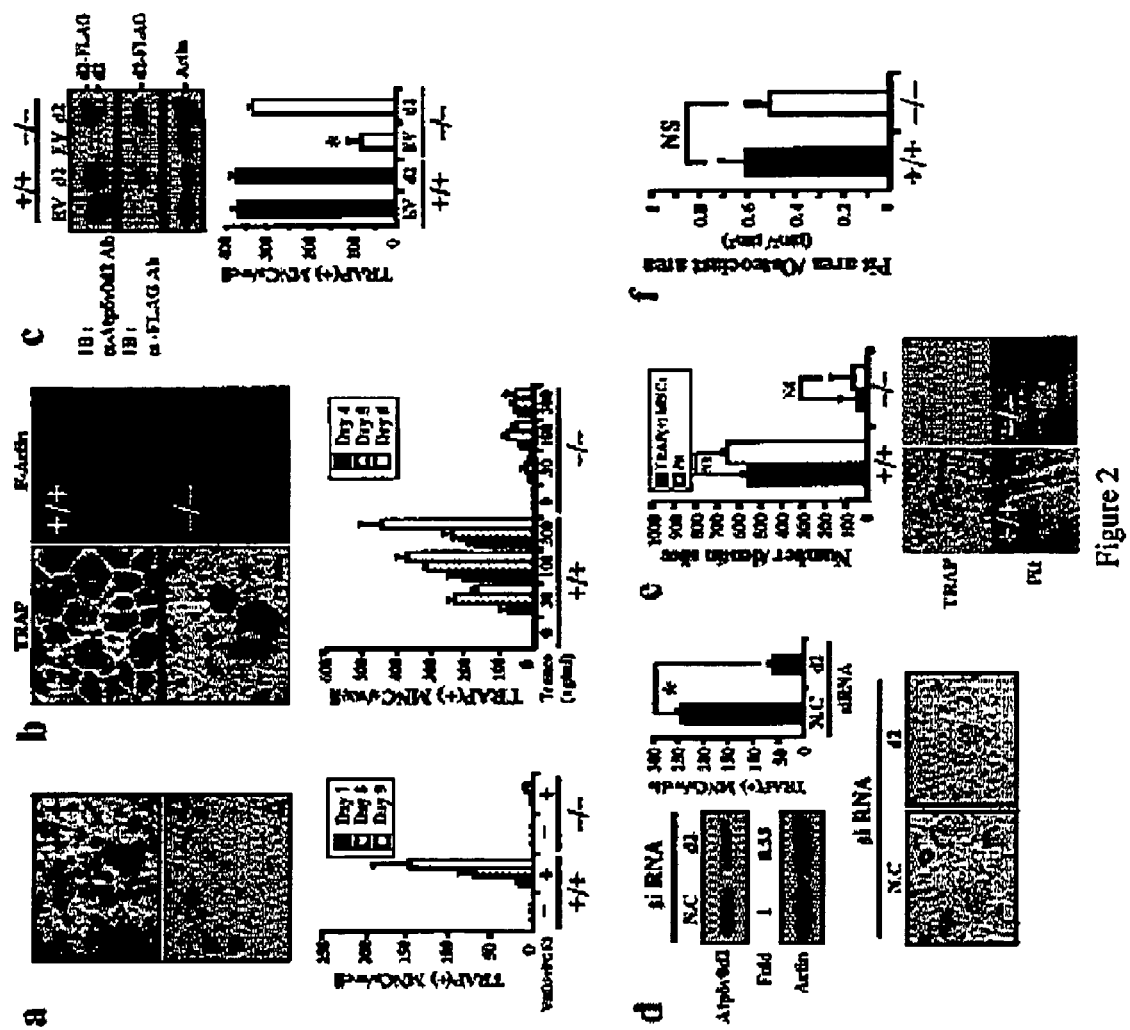
FIG. 2 shows reduced mature osteoclast formation from Atp6v0d2$^{-/-}$ bone marrow cells. (a) Osteoclast differentiation by the co-culture with osteoblasts. (top) TRAP-stained osteoclasts after 9 day culture. (bottom) TRAP$^+$ MNCs were counted. (b) Stromal cell-free osteoclast differentiation. (top) TRAP and F-actin staining after 6 days of stimulation, (bottom) TRAP$^+$ MNCs were counted at the indicated times after stimulation with TRANCE of varying concentrations. (c) Rescue of TRAP$^+$ MNC formation by reintroduction of wild-type Atp6v0d2 in Atp6v0d2$^{-/-}$ BMMs. BMMs from wild-type (+/+) and Atp6v0d2$^{-/-}$ cells were transduced with pMX-puro (EV) or pMX-Atp6v0d2-FLAG (d2-FLAG). (left) Expression of FLAG-tagged Atp6v0d2 determined by western analysis, (right) TRAP$^+$ MNCs were counted. (d) Reduction of TRAP$^+$ MNC formation by siRNA-mediated knock-down of wild-type Atp6v0d2. BMMs from wild-type (+/+) were transfected with control siRNA (N.C) or siRNA for Atp6v0d2 (d2). (top, left) Expression of Atp6v0d2 protein, (top, right) TRAP$^+$ MNCs were counted, (bottom) TRAP-stained osteoclasts. (e) Bone-resorption pits from wild-type (+/+) and Atp6v0d2$^{-/-}$ osteoclasts. Osteoclasts were made by culturing osteoclast precursors with TRANCE and M-CSF (BMM) on dentine slices. Data are expressed as mean±s.d. and are representative of at least three experiments. NS, not significant. (f) Osteoclasts were made on dentine slices, and the mean resorption area was determined using the Via-160 video Image maker-measurement system (Boeckeler Instruments). NS, not significant.
Figure 9:
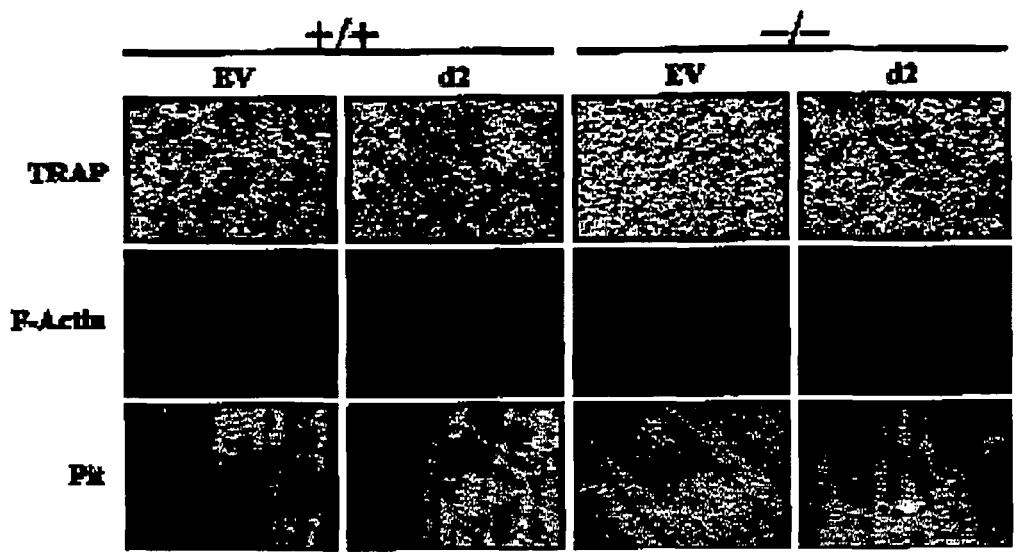
FIG. 9 shows rescue of TRAP$^+$ MNC formation by retrovirus-mediated expression of Atp6v0d2 in Atp6v0d2$^{-/-}$ BMMs. BMMs from wild-type and Atp6v0d2$^{-/-}$ cells were transduced with pMX-puro (empty vector, EV) or pMX-Atp6v0d2 tagged with FLAG (d2).
Figure 10:
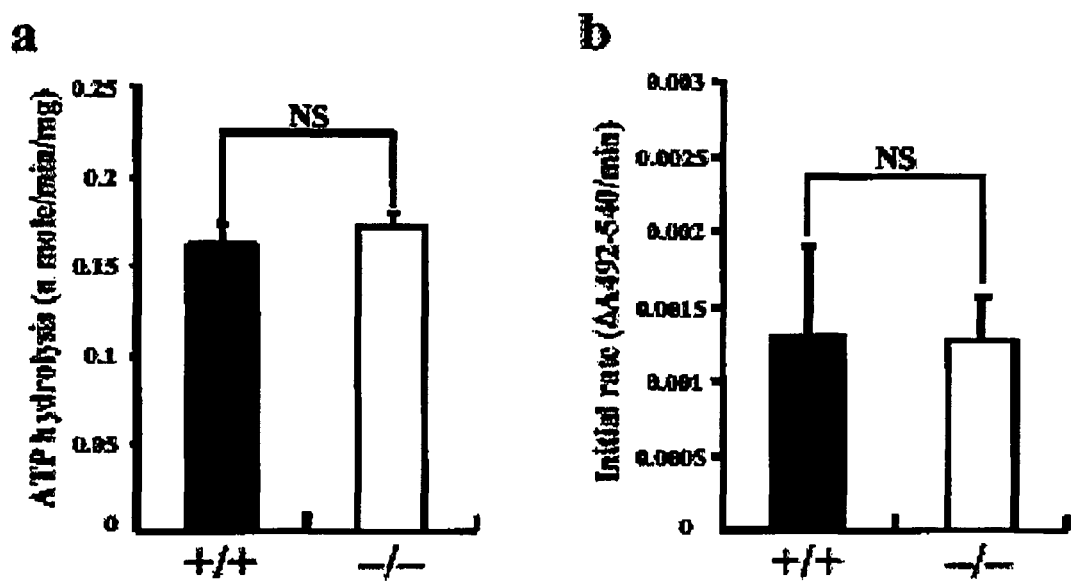
FIG. 10 shows that deficiency of Atp6v0d2 does not affect v-ATPase activity of osteoclasts. Osteoclasts were cultured from wild-type and Atp6v0d2$^{-/-}$ BMMs with M-CSF and TRANCE treatment, and membrane v-ATPases were prepared. (a) ATP hydrolysis activity was measured by assaying the release of inorganic phosphate as described in Methods. (b) Proton transport assay was performed with microsomal preparations derived from wild-type and to Atp6v0d2$^{-/-}$ osteoclasts. Data are mean±s.d., three experiments. NS, not significant.

To examine osteoclast defects in Atp6v0d2$^{-/-}$ mice, two standard in vitro osteoclast culture methods were employed: co-cultures of primary osteoblasts with bone marrow monocyte precursors (BMMs) in the presence of 1α,25(OH)$_2$D$_3$, and stromal cell-free BMM cultures with tumor necrosis factor-related activation-induced cytokine (TRANCE) and macrophage colony-stimulating factor (M-CSF). In both methods, osteoclasts, identified as TRAP$^+$ cells, were generated from BMMs of Atp6v0d2$^{-/-}$ mice (FIG. 2a, b). However, most Atp6v0d2$^{-/-}$ osteoclasts were much smaller than wild-type osteoclasts, which are usually >100 μm in diameter. The formation of large (>100 μm) osteoclasts containing more than 5 nuclei and an actin ring was greatly diminished in the absence of Atp6v0d2 (FIG. 2a,b). This defect was not due to the failure of Atp6v0d2$^{-/-}$ osteoblast to support osteoclast differentiation (FIG. 8), rather due directly to loss of Atp6v0d2 in BMMs; as reintroduction of wild-type Atp6v0d2 into Atp6v0d2$^{-/-}$ BMMs restored their ability to become large TRAP$^+$ multinucleated cells (MNCs) and because, in a complimentary approach, knock-down of Atp6v0d2 in wild-type BMMs reduced the formation of TRAP$^+$ MNCs (FIG. 2c,d and FIG. 9). Although total number of pits on dentine slices formed by Atp6v0d2$^{-/-}$ osteoclasts was markedly reduced (FIG. 2e), it correlates with the degree of reduction in the number of actin-ring positive, large TRAP$^+$ MNCs (FIG. 2e). These results indicate that Atp6v0d2 regulates the formation of large MNCs, but, once formed, bone resorption that normally requires v-ATPase proton pump activity is carried out by Atp6v0d2. Consistently, the mean resorption area formed by wild-type and Atp6v0d2$^{-/-}$ osteoclasts were comparable (FIG. 2f), and the activity of v-ATPases from Atp6v0d2$^{-/-}$ osteoclasts was similar to that of wild-type cells (FIG. 10).

Example 5

Atp6v0d2 Deficiency Results in Decreased Cell Fusion and Osteoclast Maturation

Figure 3:
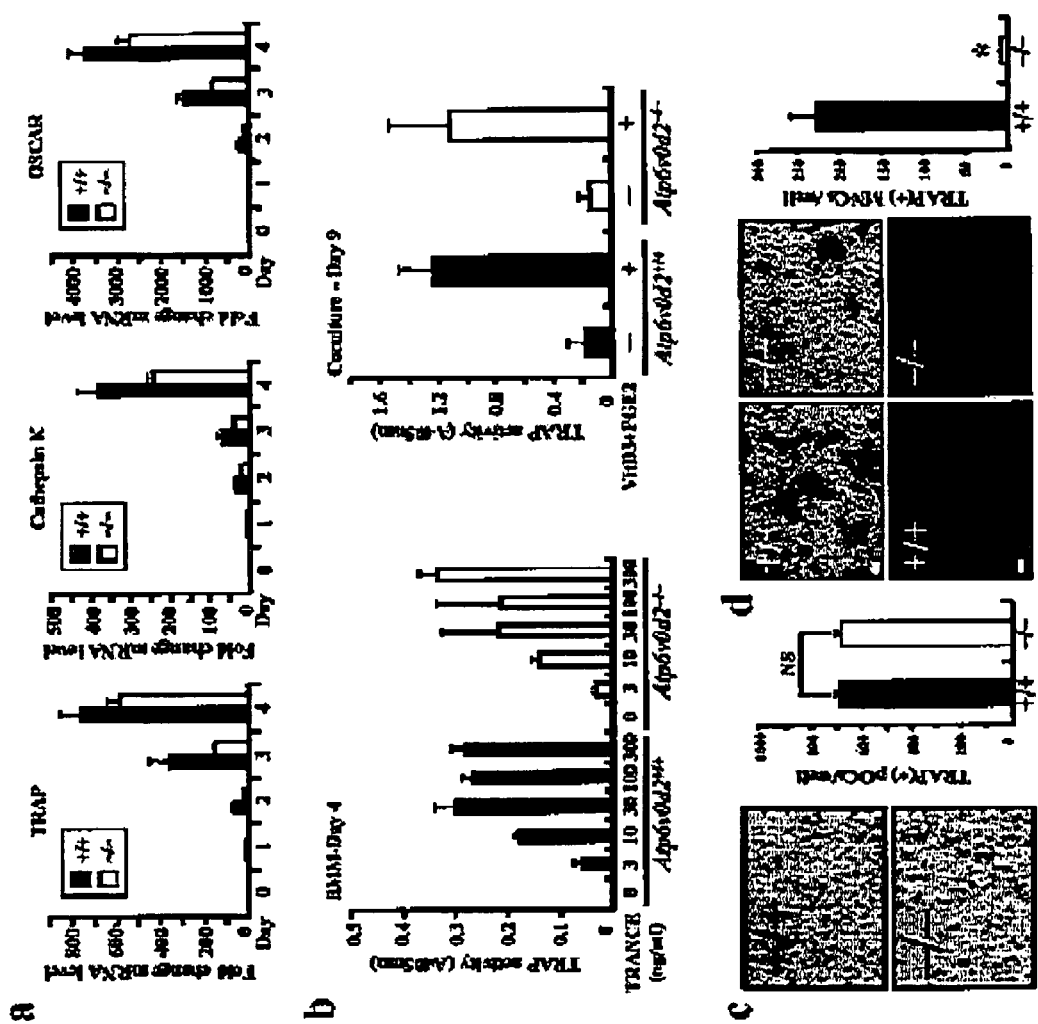
FIG. 3 shows impaired fusion of Atp6v0d2$^{-/-}$ pre-osteoclasts. (a) Real-time PCR analysis of OSCAR, TRAP and cathepsin K. RNA was isolated on the indicated days after stimulation with M-CSF/TRANCE. Day 0 indicates BMMs. (b) Osteoclasts were derived from BMMs, (left) by stimulation with TRANCE of varying concentrations for 4 days or (right) by co-culture with osteoblasts for 9 days. TRAP solution assays were performed. (c) Pre-osteoclasts isolated by co-culture of wild-type (+/+) or Atp6v0d2$^{-/-}$ bone marrow cells with osteoblasts for 4 days. (left) Cells were stained for TRAP, (right) TRAP$^+$ pre-osteoclasts (pOCs) were counted. (d) Purified mononuclear cells from (c) were induced to fuse. (left) Cells were stained for TRAP and F-actin, (right) TRAP$^+$ MNCs are counted. Data are expressed as mean±s.d. and are representative of at least three experiments. NS, not significant; *$P<0.01$, Scale bar=100 µm.

The formation of multinucleated mature osteoclasts depends on the fusion of mononuclear pre-osteoclasts, which are generated by bone marrow precursor differentiation. To determine which steps of these processes are affected by Atp6v0d2 deficiency, the expression of molecular markers signifying differentiated osteoclasts was first examined. By real-time quantitative PCR, mRNA expression levels of osteoclast-associated receptor (OSACR), cathepsin K and TRAP were shown to be comparable between Atp6v0d2$^{-/-}$ and to wild-type osteoclasts (FIG. 3a). The total TRAP activity, accounting for both mono- and multi-nucleated osteoclasts, was comparable between Atp6v0d2$^{-/-}$ and wild-type osteoclast cultures (FIG. 3b), which is consistent with in vivo bone parameters (FIG. 1 and Table 2).

TABLE II

Static histomorphometric parameters of bone structure in femur of wildtype and Atp6v0d2-/- mice.

| | No. of mice | BV/TV (%) | ObS/BS (%) | OcS/BS (%) | NOc/BPm (N/mm$^2$) | Tb. Th. (μm) | Tb. Sp. (μm) | Tb.N. (N/mm) |
|---|---|---|---|---|---|---|---|---|
| WT | 4 | 9.84 ± 0.69 | 14.6 ± 1.52 | 10 ± 0.8 | 4.1 ± 0.72 | 33.9 ± 3.0 | 247.5 ± 34.5 | 3.7 ± 0.42 |
| KO | 4 | 24.2 ± 1.37† | 26.8 ± 3.15* | 4.55 ± 0.51† | 3.15 ± 0.98 | 40.9 ± 5.23 | 133.4 ± 5.41* | 5.22 ± 0.25* |

†P < 0.01,
*P < 0.05 (Only the columns marked with * or † show statistical differences)

Figure 11:
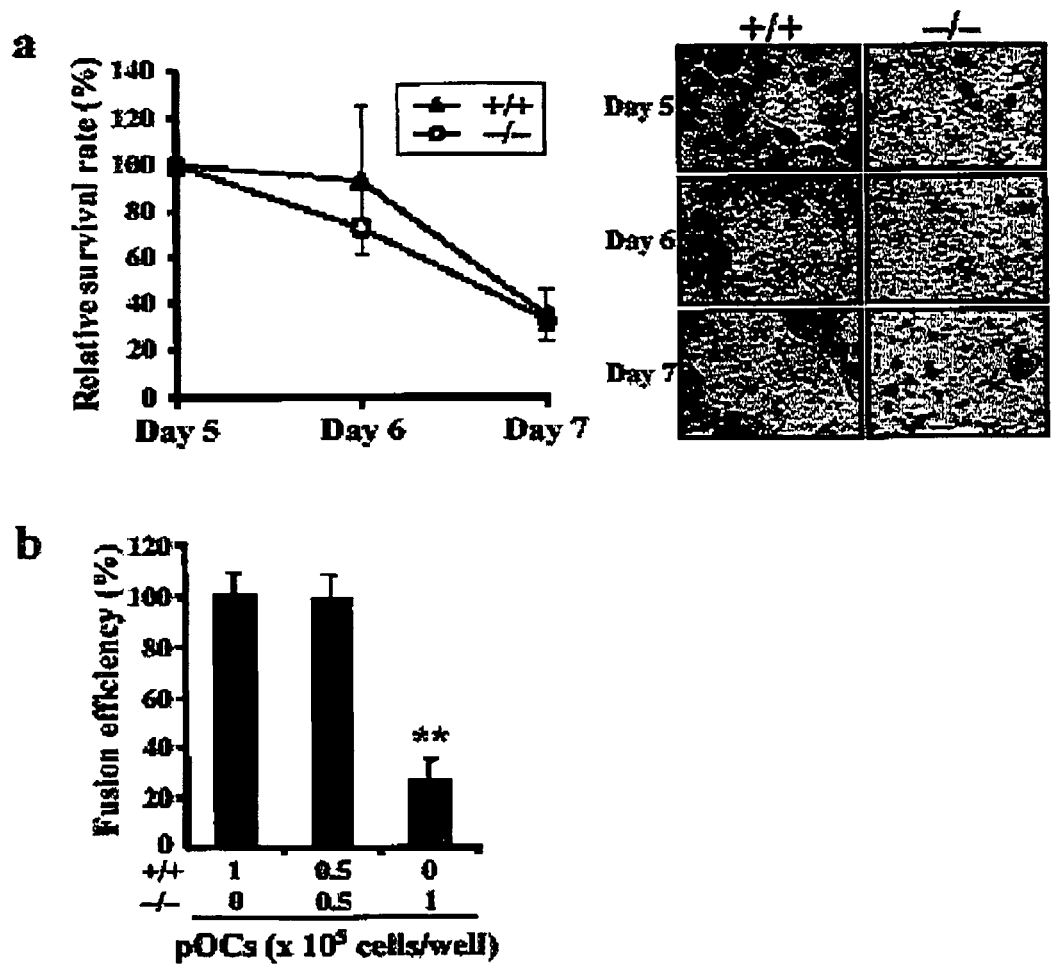
FIG. 11 shows (a) Atp6v0d2 deficiency does not enhance cell death. Relative survival rate was measured as described in the supplementary methods. *apoptotic TRAP$^+$ MNC (b) The efficiency of pre-osteoclast fusion was calculated by dividing the total number of nuclei within TRAP(+) MNCs by the number of TRAP(+) MNCs. Data are expressed as mean±S.D. *, p<0.01.

Moreover, when the efficiency of mononuclear pre-osteoclast formation was directly measured from BMMs of wild-type littermates and Atp6v0d2$^{-/-}$ mice, they did not show significant differences (FIG. 3c). Hence, early steps of osteoclast differentiation, at least up to generating mononuclear pre-osteoclasts, do not seem to be affected by Atp6v0d2 deficiency. We determined next whether subsequent cell-cell fusion of pre-osteoclasts was affected by the deletion of Atp6v0d2, by inducing fusion of purified pre-osteoclasts with TRANCE and M-CSF. When fusion outcome was measured by the number of large TRAP$^+$ MNCs formed, there was significant reduction in the formation of mature giant osteoclasts in the absence of Atp6v0d2 (FIG. 3d). Once formed, however, Atp6v0d2$^{-/-}$ MNCs showed survival rate similar to wild-type (FIG. 11). These results show that Atp6v0d2 is not involved in the differentiation of BMMs up to TRAP$^+$ mononuclear pre-osteoclasts, but it does control subsequent cell-cell fusion to generate multinucleated mature osteoclasts.

Figure 4:
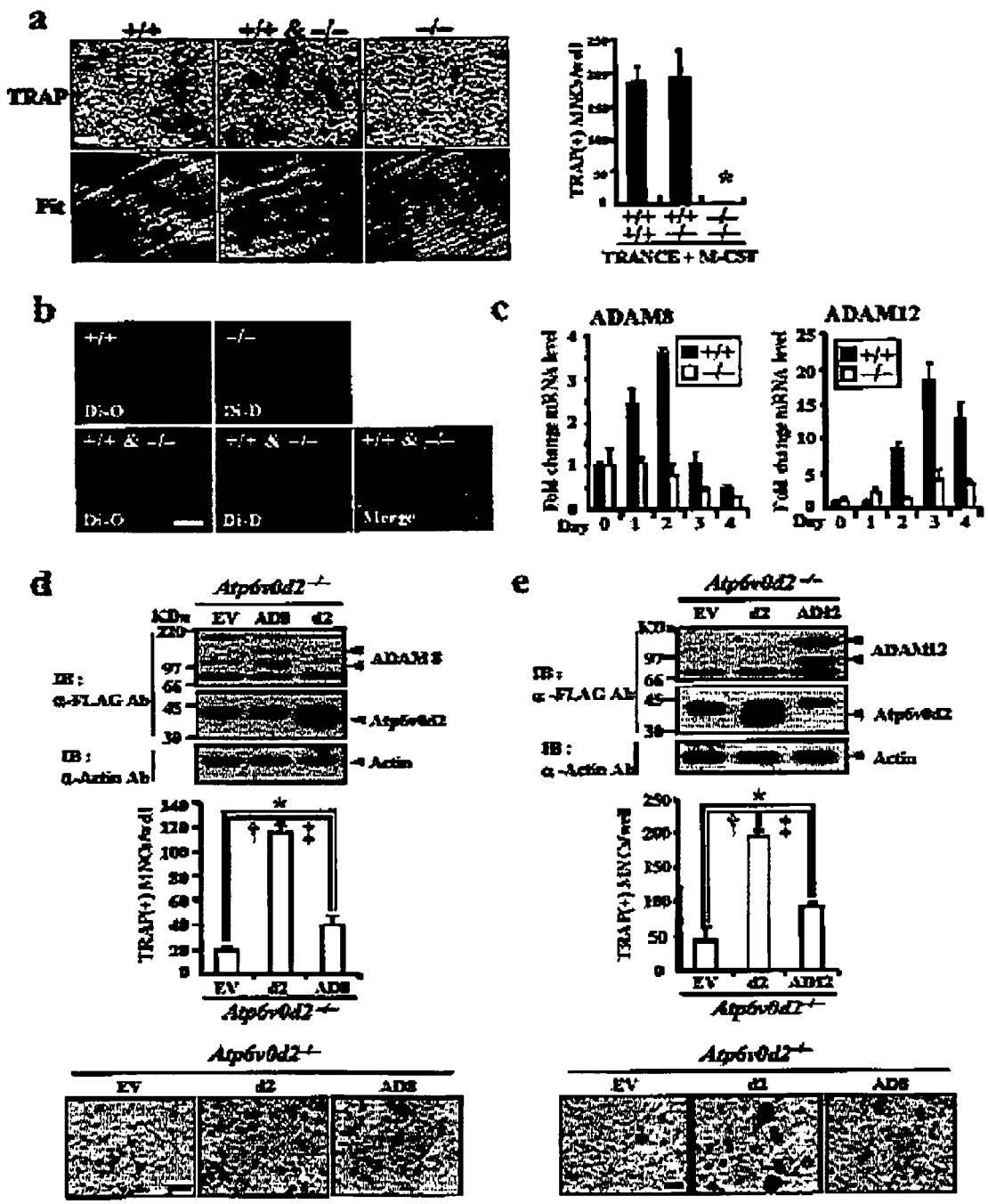
FIG. 4 shows Rescue of cell fusion in Atp6v0d2$^{-/-}$ osteoclasts by ADAM8/12. (a) Pre-osteoclasts from wild-type and Atp6v0d2$^{-/-}$ bone-marrow cells were cultured independently or mixed in the presence of M-CSF and TRANCE for 24 h (+/+; wild-type only, +/+ & -/-; wild-type and mutant cell equal mixture, -/-; mutant cells only). (left) TRAP staining and bone resorption pits, (right) TRAP$^+$ MNCs were counted. *$P<0.01$ (b) For heterotypic fusion, DiO-stained wild-type (+/+) and DiD-stained mutant (-/-) pre-osteoclasts were cultured independently (top) or mixed at equal numbers (bottom) for fusion assays, and examined using fluorescence microscopy. (c) (left) ADAM8 or (right) ADAM12 expression during osteoclast differentiation. RNA was isolated from BMMs (day 0) and subsequently treated with M-CSF/TRANCE (day 1-4). (d, e) Rescue of TRAP$^+$ MNC formation by retrovirus-mediated expression of Atp6v0d2, ADAM8 or ADAM12 in Atp6v0d2$^{-/-}$ BMMs. EV, empty vector; d2, Atp6v0d2-FLAG; ADB, ADAM8-FLAG; AD12, ADAM12-FLAG. Expression of FLAG-tagged Atp6v0d2, ADAM8, or ADAM12 was confirmed by immunoblot analysis using anti-FLAG antibody. TRAP$^+$ MNCs were counted as described above. A representative TRAP staining is also shown. Scale bar=100 µm. Data are expressed as mean±s.d. and are representative of three experiments. *$P<0.05$; †$P<0.01$; ‡$P<0.02$.
Figure 12:
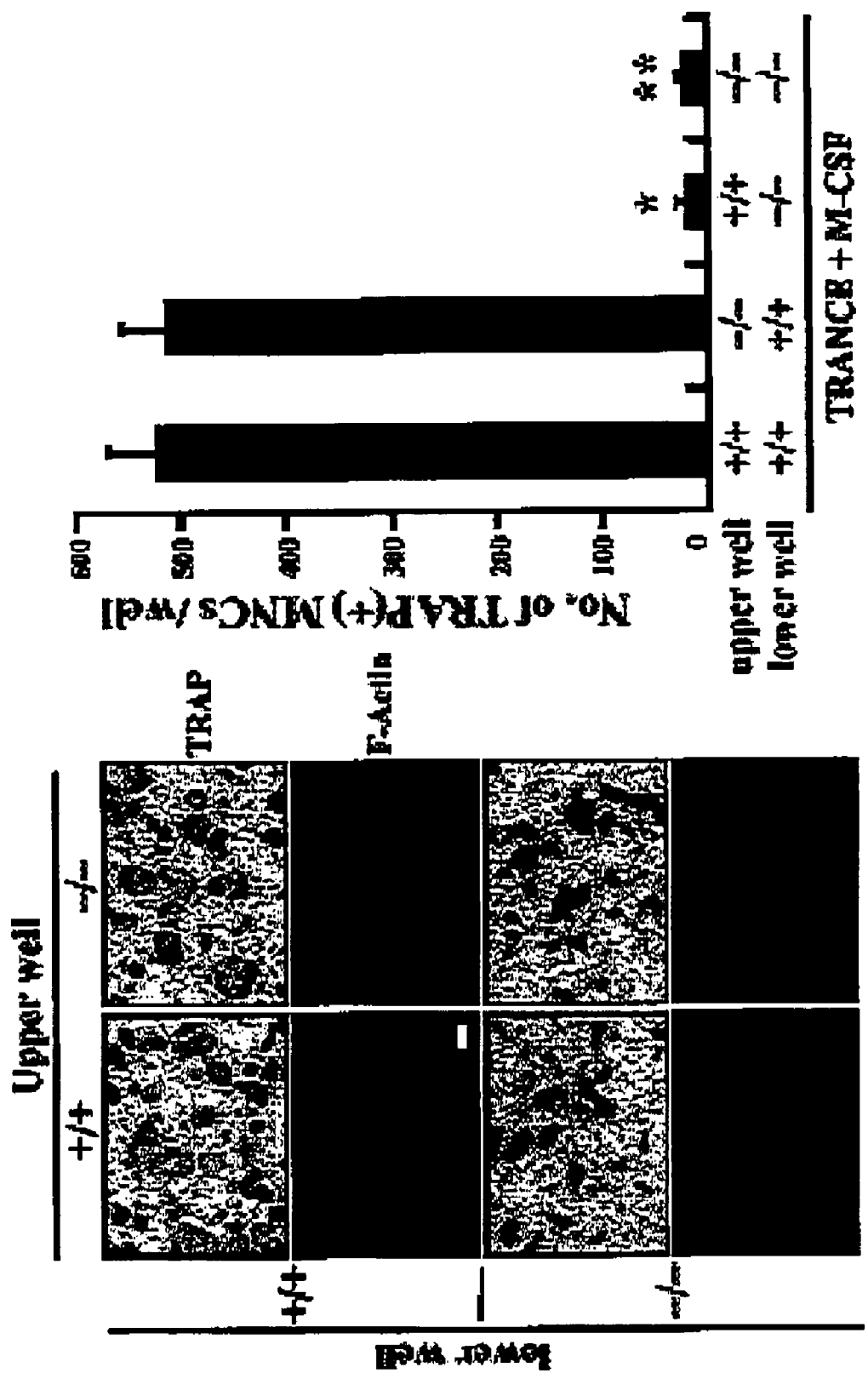
FIG. 12 shows pre-osteoclasts from wild-type or Atp6v0d2$^{-/-}$ BMs were cultured in upper wells or lower wells of 24-transwell plates with M-CSF and TRANCE as indicated. After culture for 24 h, cells were stained for F-actin and TRAP. TRAP$^+$ MNCs were counted. Data are expressed as mean±s.d. NS, not significant; *P<0.001; **P<0.001, Scale bar=100 μm.

The mechanism of cell-cell fusion during osteoclast maturation remains largely unknown. To define the potential mechanism affected by the absence of Atp6v0d2, whether defects in the Atp6v0d2$^{-/-}$ pre-osteoclasts are dominant or recessive to wild-type pre-osteoclasts during fusion was first examined. When wild-type and Atp6v0d2$^{-/-}$ pre-osteoclasts were mixed and then induced to fuse, the formation of large TRAP$^+$ MNCs was restored to a level with fusion efficiency comparable to cultures containing only the wild-type pre-osteoclasts (FIG. 4a and FIG. 11), indicating that wild-type pre-osteoclasts can fuse with Atp6v0d2$^{-/-}$ pre-osteoclasts. Heterotypic fusion was further confirmed by the use of vital dye stained pre-osteoclasts (FIG. 4b). These data show that wild-type cells can restore to the fusion capacity of Atp6v0d2$^{-/-}$ cells. This ability does not appear due to soluble factors produced by wild-type cells, since they cannot rescue the defects of Atp6v0d2$^{-/-}$ cells in trans-well plates (FIG. 12).

Example 6

Atp6v0d2 Deficiency Causes Reduction in the Factors Necessary for Fusion

Figure 13:
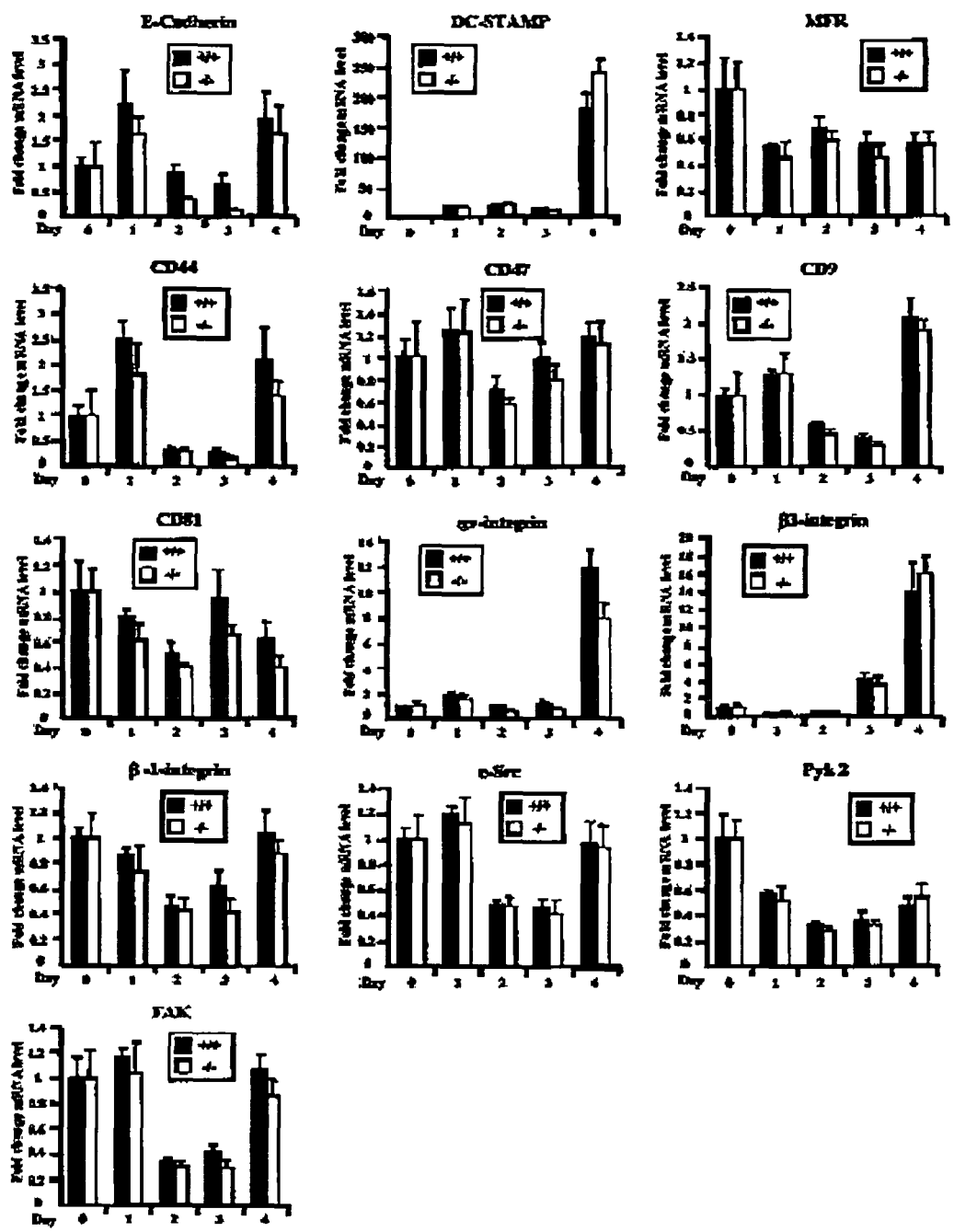
FIG. 13 shows real-time PCR of ADAM family genes from wild-type and Atp6v0d2$^{-/-}$ osteoclasts. The assay was carried out as described in the supplementary FIG. 8.
Figure 14:
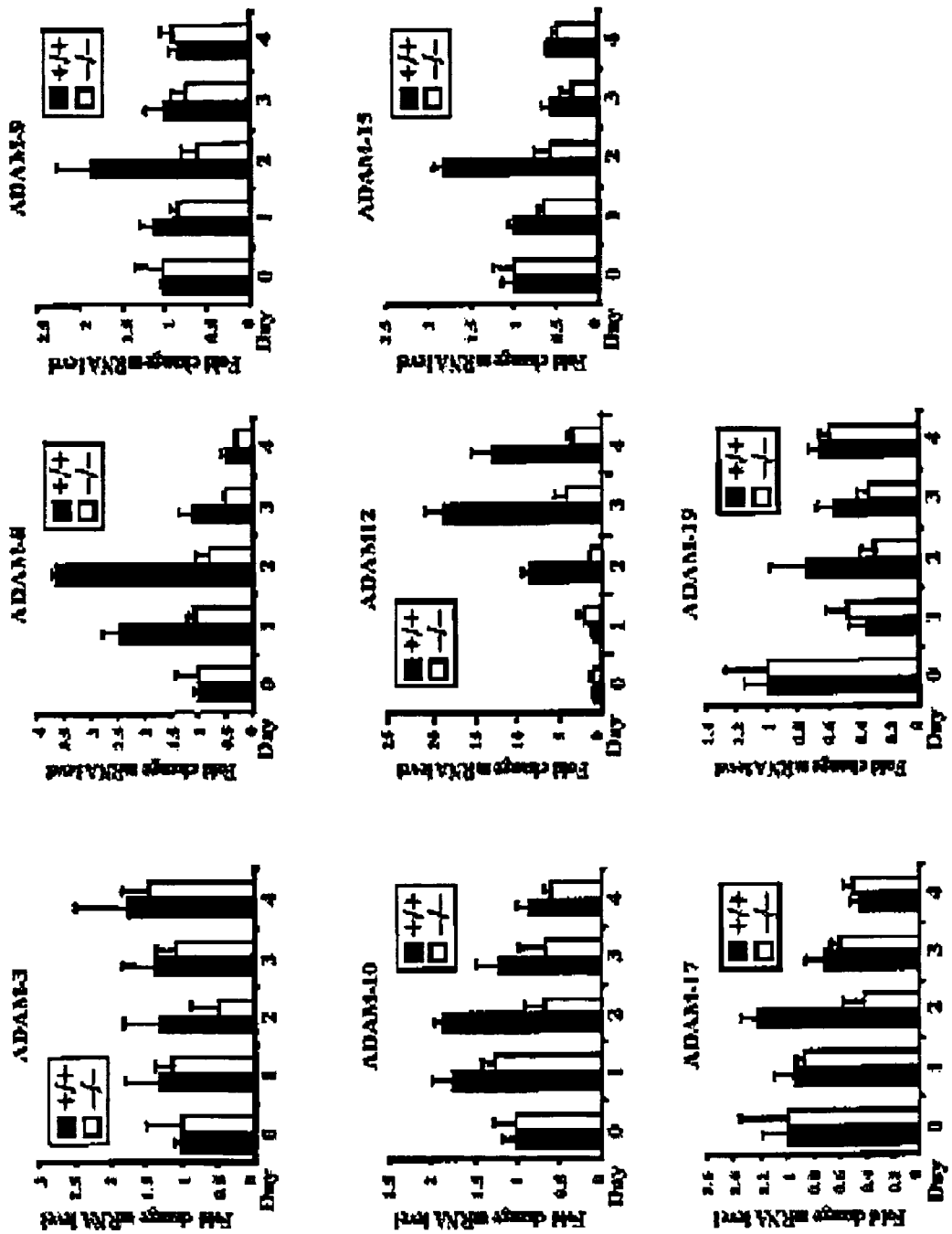
FIG. 14 shows Atp6v0d2 does not interact with ADAM12, ADAM8 or DC-STAMP. (a) 293 cells were co-transfected with FLAG-Atp6v0d2 and FLAG-ADAM12. Lane 1: whole cell lysate probed with anti-FLAG, Lane 2: cell lysate was immunoprecipitated with rabbit polyclonal anti-Atp6v0d2, then probed with anti-FLAG (b) 293 cells were co-transfected with FLAG-Atp6v0d2 and FLAG-ADAM8. Lane 1: whole cell lysate probed with anti-FLAG, Lane 2: cell lysate was immunoprecipitated with rabbit polyclonal anti-Atp6v0d2, then probed with anti-FLAG (c) 293 cells were co-transfected with FLAG-Atp6v0d2 and V5-DC-STAMP. Lane 1: whole cell lysate was probed with anti-V5 (top) and anti-FLAG (bottom), Lane 2: cell lysate was immunoprecipitated with rabbit polyclonal anti-Atp6v0d2, to then probed with anti-V5 (top) and anti-FLAG (bottom).
Figure 15:
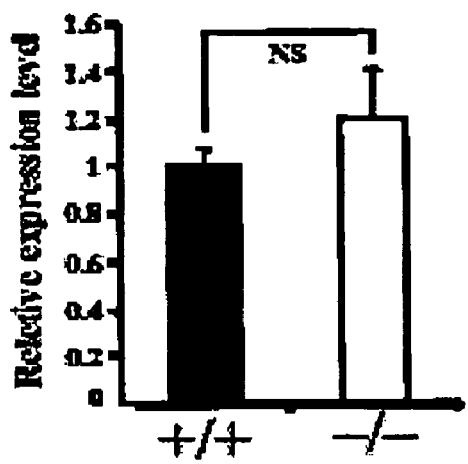
FIG. 15 shows (a) DC-STAMP deficient cells express Atp6v0d2 mRNA and protein at levels similar to wild-type cells. BMs isolated from wild-type and DC-STAMP$^{-/-}$ mice were induced to become osteoclasts by treatment with M-CSF and TRANCE. RNA and protein was isolated, and analyzed by real-time PCR and western analysis. (b) MFR (Macrophage fusion receptor, SHPS-1/SIRPalpha) does not regulate the expression of Atp6v0d2. BM cells were transfected with control (N.C) or siRNA for MFR (MFR) as described in the supplementary methods, and induced to differentiate by TRANCE. mRNA level was measured by semi-quantitative RT-PCR, normalized to 18S RNA. TRAP$^+$ MNCs are counted, and TRAP stained cells are shown.
Figure 15:
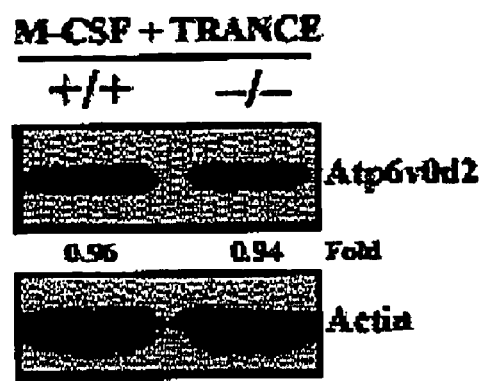
Figure 15:
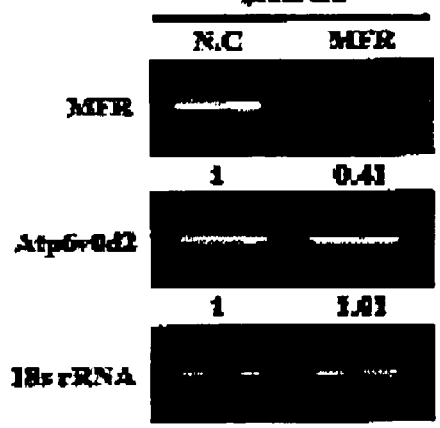
Figure 15:
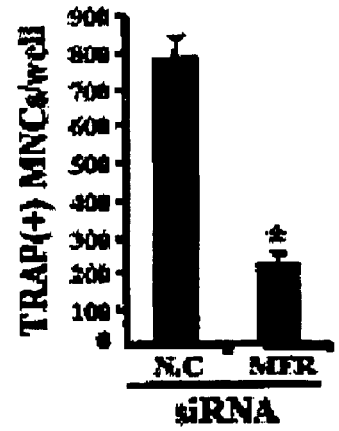
Figure 15:
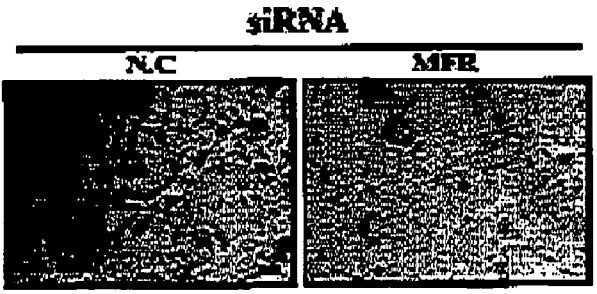
Figure 16:
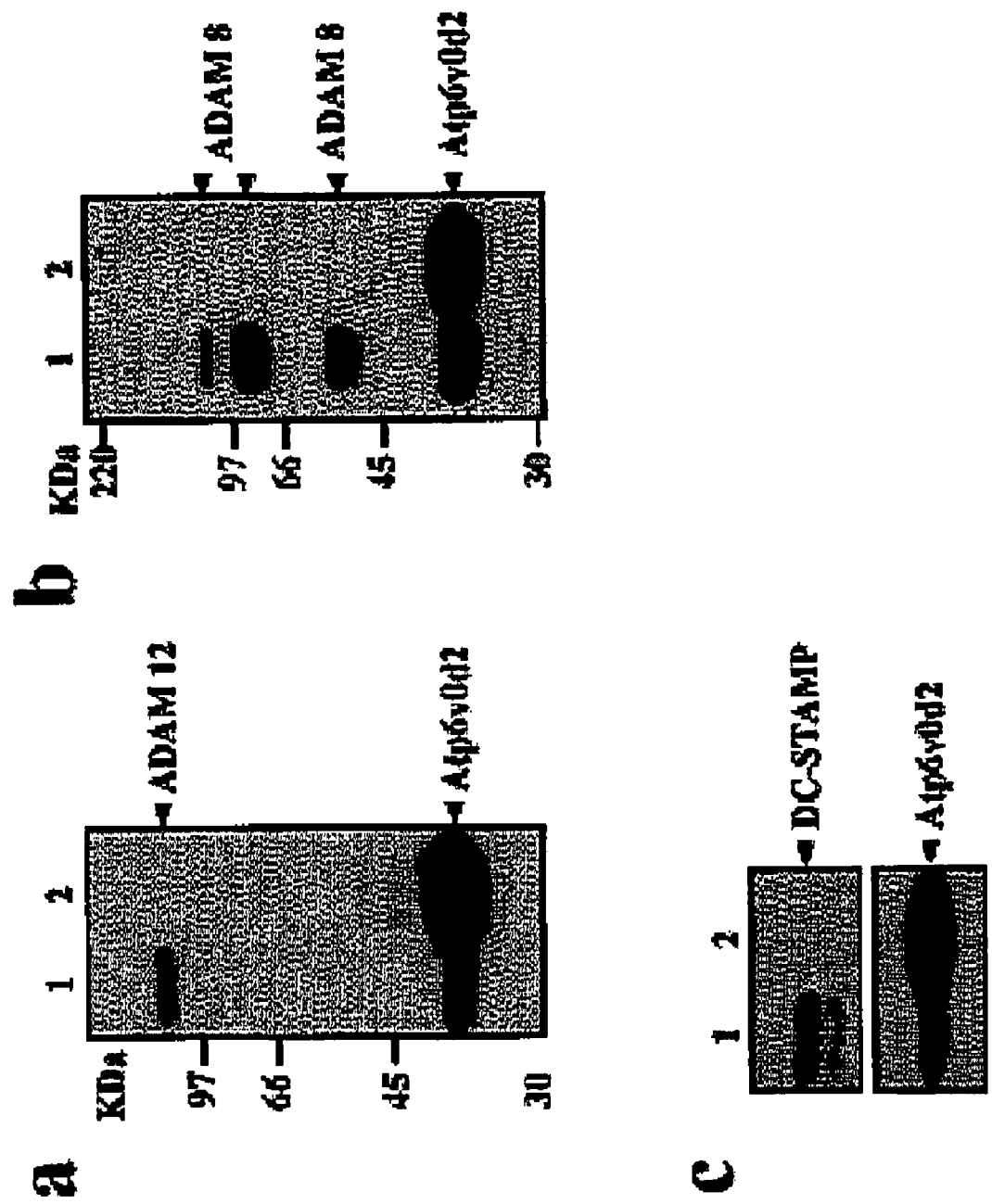
FIG. 16 shows Atp6v0d2 does not interact with ADAM12, ADAM8 or DC-STAMP. (a) 293 cells were co-transfected with FLAG-Atp6v0d2 and FLAG-ADAM12. Lane 1: whole cell lysate probed with anti-FLAG, Lane 2: cell lysate was immunoprecipitated with rabbit polyclonal anti-Atp6v0d2, then probed with anti-FLAG (b) 293 cells were co-transfected with FLAG-Atp6v0d2 and FLAG-ADAM8. Lane 1: whole cell lysate was probed with anti-FLAG, Lane 2: cell lysate was immunoprecipitated with rabbit polyclonal anti-Atp6v0d2, then probed with anti-FLAG (c) 293 cells were co-transfected with FLAG-Atp6v0d2 and V5-DC-STAMP. Lane 1: whole cell lysate was probed with anti-V5 (top) and anti-FLAG (bottom), Lane 2: cell lysate was immunoprecipitated with rabbit polyclonal anti-Atp6v0d2, then probed with anti-V5 (top) and anti-FLAG (bottom).
Figure 17:
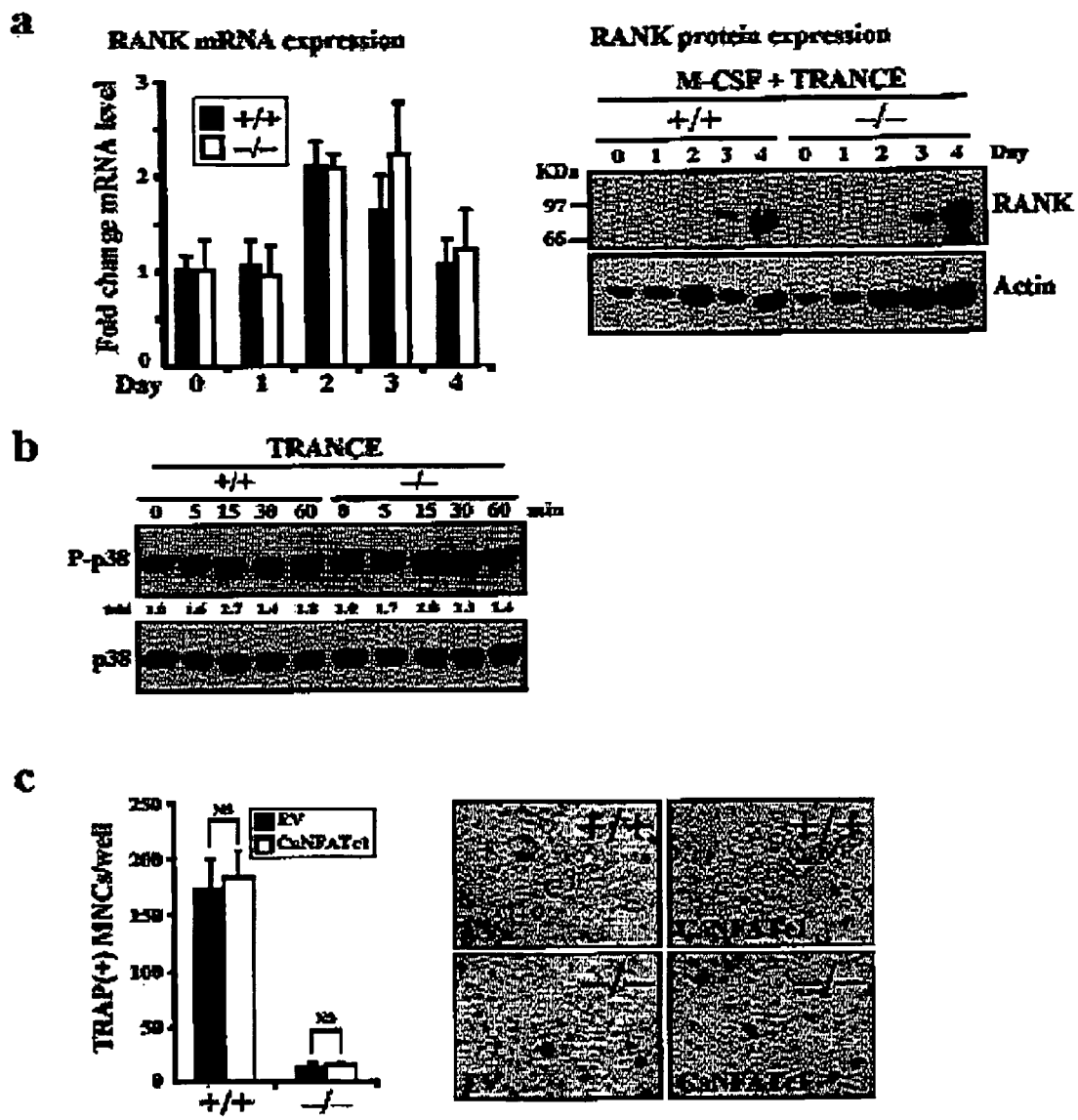
FIG. 17 shows (a) RANK expression or its signaling is not affected in the absence of Atp6v0d2. BMMs from wild-type and Atp6v0d2$^{-/-}$ mice were treated with M-CSF (30 ng/ml) and TRANCE (150 ng/ml) for 4 days. Total RNA was isolated each day after treatment. Expression of RANK was determined by northern blot and western analysis. (+/+) wild-type cells, (−/−) (b) RANK-mediated signaling is not affected in the absence of Atp6v0d2. Cells were treated with TRANCE for the indicated period, harvested, and analyzed by Western analysis as described in the supplementary methods. (c) Overexpression of constitutive active NFATc1 does not complement the defects in Atp6v0d2 deficient cells. Rescue of TRAP$^+$ MNC formation by retrovirus-mediated expression of CaNFATc1 in Atp6v0d2$^{-/-}$ BMMs. EV, empty vector; CaNFATc1, constitutive active NFATc1 (CaNFATc1) TRAP$^+$ MNCs were counted as described above.

The data indicates that Atp6v0d2 deficiency most likely causes the reduction of factors necessary for fusion. To elaborate this further, mRNA expression of molecules previously implicated in cell-cell fusion was measured in various systems: E-cadherin, DC-STAMP, integrins, Src-family kinases and ADAM family proteins[3,15,16]. RNA levels of most genes were remarkably similar between wild-type and Atp6v0d2$^{-/-}$ cells during the entire course of osteoclast differentiation and maturation (FIGS. 13, 14). Conversely, DC-STAMP or MFR does not appear to regulate Atp6v0d2 expression (FIG. 15). However, mRNA level of ADAM8 and ADAM12 in Atp6v0d2$^{-/-}$ cells was dramatically reduced (4-5 fold) (FIG. 4c). Although ADAM8 or 12 does not mediate fusion by themselves, they have been shown to support osteoclast fusion in vitro. To examine whether increased ADAM8 or 12 expression can compensate decreased fusion of Atp6v0d2$^{-/-}$ osteoclasts, Atp6v0d2$^{-/-}$ BMMs were infected with either empty vector (EV), ADAM8 or ADAM12 retroviruses. Positively transduced cells were selected for drug resistance and subjected to osteoclast differentiation assays. When analyzed for the presence of mature osteoclasts, ADAM8 or ADAM12 transduced Atp6v0d2$^{-/-}$ BMMs generated significantly greater numbers of actin-ring positive, large TRAP$^+$ MNCs that resorbed bone, when compared to EV-infected Atp6v0d2$^{-/-}$ BMMs (FIG. 4d, e). The rescue of Atp6v0d2$^{-/-}$ BMMs by ADAM8 or ADAM12 transduction, however, was less efficient (~30-40%) than that by wild-type Atp6v0d2 transduction (FIG. 4d, e). These results indicate that the increased level of ADAM8 or ADAM12 complements, at least in part, defective fusion of Atp6v0d2$^{-/-}$ osteoclasts.

Having described preferred embodiments as provided hereinwith reference to the accompanying drawings, it is to be understood that the invention is not limited to the precise embodiments, and that various changes and modifications may be effected therein by those skilled in the art without departing from the scope or spirit as provided hereinas defined in the appended claims.

---

SEQUENCE LISTING

```
<160> NUMBER OF SEQ ID NOS: 8

<210> SEQ ID NO 1
<211> LENGTH: 1410
<212> TYPE: DNA
<213> ORGANISM: Mouse

<400> SEQUENCE: 1
aggactcgga gccacttcag cctgagcagt atgcttgaga ctgcagagct gtacttcaat      60
gtggaccatg gctacctgga gggcctggtt cgaggatgca aagccagcct cctaactcag     120
caggactatg tcaacctagt gcagtgtgag accttggaag acctgaaaat tcatctccag     180
accacggact atggcaactt cctggctaat gaaacaaatc ctctcactgt ttccaaaatt     240
gacacggaga tgaggaagaa gctctgcaga gagtttgact atttccggaa tcattccttg     300
gagcccctga gcacatttct cacctacatg acatgcagct atatgataga caatataatt     360
ctacttatga atggggcctt gcaaaagaaa tctgtgaaag aagttctagc caagtgtcac     420
ccactgggcc gtttcacaga gatggaagct gtcaacattg cagagacccc ctcagatctc     480
ttcaaggctg tgctggttga aacaccatta gctccattct ttcaagattg tatgtctgaa     540
aacactcttg atgaactgaa tattgaatta ctgcgcaata aactatacaa gtcttacctt     600
gaggcattct acaaattctg caaggatcac ggtgatgtca cagcagacgt tatgtgtccc     660
attcttgagt ttgaggccga cagacgcgct ttaatcatca ctctgaactc atttggcact     720
gaactaagca aagaagacag ggagaccctc ttccccacct gcggcaggct ctatccagag     780
gggttgcggt tgttagctca agctgaagac tttgagcaga tgaagagagt ggcagataat     840
```

```
tatggagttt acaagccttt gtttgacgct gtcggtggca gtgggggaa gacactggaa        900 gacgttttct atgagagaga ggtacagatg aatgtgctgg cattcaacag gcaattccat        960
tatggtgtgt tttatgcgta tgtaaagttg aaggagcaag agatgagaaa tatcgtgtgg       1020
atagcagaat gcatctcaca gaggcatcga actaaaatca acagctacat tccaattta        1080 taagccagtg tacagaagat catacatgtt gccatgaagt tattgaggaa aggaaggggg       1140
attgtgtcac attatctaga ttatataaaa gtaagtcata ccacctttcc ataaactaca       1200
tgtccactgg aagcccaagt aaacagaact tgaaacaaaa tatgcctttc ttggtttcca       1260
acaagcccca gtggtttttt cacatttatg acttcctgct cactggcctc atacgttcat       1320
tttcattgac cctgtggcac ttttgtatt ctcattgggt cagactaaaa tcataggtaa        1380
tcaggttcaa aaaaaaaaaa aaaaaaaaaa                                        1410

<210> SEQ ID NO 2
<211> LENGTH: 2487
<212> TYPE: DNA
<213> ORGANISM: Mouse

<400> SEQUENCE: 2
aggactcgga gccacttcag cctgagcagt atgcttgaga ctgcagagct gtacttcaat         60
gtggaccatg gctacctgga gggcctggtt cgaggatgca aagccagcct cctaactcag        120
caggactatg tcaacctagt gcagtgtgag accttggaag acctgaaaat tcatctccag        180
accacggact atgcaacttc ctggctaat gaaacaaatc ctctcactgt tccaaaatt         240 gacacggaga tgaggaagaa gctctgcaga gagtttgact atttccggaa tcattccttg        300
gagcccctga gcacatttct cacctacatg acatgcagct atatgataga caatataatt        360
ctacttatga atggggcctt gcaaaagaaa tctgtgaaag aagttctagc caagtgtcac        420
ccactgggcc gtttcacaga gatggaagct gtcaacattg cagagacccc ctcagatctc        480
ttcaaggctg tgctggttga acaccatta gctccattct ttcaagattg tatgtctgaa         540
aacactcttg atgaactgaa tattgaatta ctgcgcaata actatacaa gtcttacctt         600 gaggcattct acaaattctg caaggatcac ggtgatgtca cagcagacgt tatgtgtccc        660
attcttgagt ttgaggccga cagacgcgct ttaatcatca ctctgaactc atttggcact        720
gaactaagca aagaagacag ggagaccctc ttccccacct gcggcaggct ctatccagag        780
gggttgcggt tgttagctca agctgaagac tttgagcaga tgaagagagt ggcagataat        840
tatggagttt acaagccttt gtttgacgct gtcggtggca gtgggggaa gacactggaa        900 gacgttttct atgagagaga ggtacagatg aatgtgctgg cattcaacag gcaattccat        960
tatggtgtgt tttatgcgta tgtaaagttg aaggagcaag agatgagaaa tatcgtgtgg       1020
atagcagaat gcatctcaca gaggcatcga actaaaatca acagctacat tccaattta        1080 taagccagtg tacagaagat catacatgtt gccatgaagt tattgaggaa aggaaggggg       1140
attgtgtcac attatctaga ttatataaaa gtaagtcata ccacctttcc ataaactaca       1200
tgtccactgg aagcccaagt aaacagaact tgaaacaaaa tatgcctttc ttggtttcca       1260
acaagcccca gtggtttttt cacatttatg acttcctgct cactggcctc atacgttcat       1320
tttcattgac cctgtggcac ttttgtatt ctcattgggt cagactaaaa tcataggtaa        1380
tcaggttctt cacgagttct tttccgttct tctccccaag ctcaaacact gctttgcctt       1440
ttacgtgttt ggtccttcca tgcattcacg aaaatgcaaa gctggggta gctaacatac        1500 accatgcttg gtgaagacac gttccttcc tttcccccaa gacttttgag aaagatagat        1560
```

-continued

| | |
|---|---|
| tccccaaatg caagcattgt taaatttatt actaaattag attatcaacg cacacataga | 1620 |
| gacagagaga gagagagaga gacagacaga cagacagaca gaaggatgaa taacttatat | 1680 |
| cgatatgtat accagtggtt ctgtcatact ttattccaga aaatccaact aattgtactt | 1740 |
| tattccttca gatagatgta gatacagcat ggttgctaca taaagttgaa acaatgcaga | 1800 |
| ggttgctcag aaaagaaaa atagcaaaat gtgtctccaa tcttttcttt aaataggaaa | 1860 |
| ttttcttaa atatagtcta tgcttgctct gcttcacaaa ttaaatctgt gcagtcaaca | 1920 |
| tgatgactca gcaggtaaga gcttgaagtc aactccatga gttcgattcc tggaatctca | 1980 |
| catatggaag gagggaactg caaaactaca agatcatctt taatcctta atctttactt | 2040 |
| atgcacccca ccactacaca cacttacaaa agaattttaa agaagggcac agaaataatg | 2100 |
| tgaactaatt ttactataca ctctctatat acacatgcta tgtagaatag tatgcataaa | 2160 |
| ctaaggagca caacatttt atgtagaata atcatttata aatataacaa aataatgtt | 2220 |
| ttgttgaact aagaagaaag ccaagtgcct actccttgac tgcagatgca atttacccag | 2280 |
| ctgcctcctg cccagaccaa cacaccttct caaccacctt agactgtcct ctcaaaccct | 2340 |
| gacccaaaag aaaccccttcc ctttctaaac tgttgtttca ggtattttgt ggcagcaaca | 2400 |
| caacaaagta actaatacag aaaactgata ctgccattgc tacaataaac ttgattttgg | 2460 |
| gattgccaaa aaaaaaaaa aaaaaaa | 2487 |

<210> SEQ ID NO 3
<211> LENGTH: 1306
<212> TYPE: DNA
<213> ORGANISM: Human

<400> SEQUENCE: 3

| | |
|---|---|
| ggaaactagt cacaaaaacc ctgactatca cctgatagat tgcttgtgct gcctgataat | 60 |
| tactcgcact tttcccaggc tagtgcaaat cttcaggggc cgtccaggac tacagagctg | 120 |
| tttcacccta ccttggcttc aatctcttcc cccatgctcg aaggtgcgga gctgtacttc | 180 |
| aacgtggacc atggctacct ggagggcctg gttcgaggat gcaaggccag cctcctgacc | 240 |
| cagcaagact atatcaacct ggtccagtgt gagaccctag aagacctgaa aattcatctc | 300 |
| cagactactg attatggtaa ctttttggct aatcacacaa atcctcttac tgtttccaaa | 360 |
| attgacactg agatgaggaa aagactatgt ggagaatttg agtatttccg gaatcattcc | 420 |
| ctggagcccc tcagcacatt tctcacctat atgacgtgca gttatatgat agacaatgtg | 480 |
| attctgctga tgaatggtgc attgcagaaa aaatctgtga agaaattct ggggaagtgc | 540 |
| cacccccttgg gccgtttcac agaaatggaa gctgtcaaca ttgcagagac accttcagat | 600 |
| ctctttaatg ccattctgat cgaaacgcca ttagctccat tcttccaaga ctgcatgtct | 660 |
| gaaaatgctc tagatgaact gaatattgaa ttgctacgca ataaactata caagtcttac | 720 |
| cttgaggcat tctataaatt ctgtaagaat catggtgatg tcacagcaga agttatgtgt | 780 |
| cccattcttg agtttgaggc cgacagacgt gcttttatca tcactcttaa ctcctttggc | 840 |
| actgaattga gcaaagaaga ccgagagacc ctctatccaa ccttcggcaa actctatcct | 900 |
| gaggggttgc ggctgttggc tcaagcagaa gactttgacc agatgaagaa cgtagcggat | 960 |
| cattacggag tatacaaacc tttatttgaa gctgtaggtg gcagtggggg aaagacattg | 1020 |
| gaggacgtgt tttacgagcg tgaggtacaa atgaatgtgc tggcattcaa cagacagttc | 1080 |
| cactacggtg tgtttttatgc atatgtaaag ctgaaggaac aggaaattag aaatattgtg | 1140 |
| tggatagcag aatgtatttc acagaggcat cgaactaaaa tcaacagtta cattccaatt | 1200 |

-continued

```
ttataaccca agtaaggttc tcaaatgtag aaaattataa atgttaaaag gaagttattg    1260
aagaaaataa aagaaattat gttatattaa aaaaaaaaaa aaaaaa                   1306

<210> SEQ ID NO 4
<211> LENGTH: 2481
<212> TYPE: DNA
<213> ORGANISM: Human

<400> SEQUENCE: 4
ggaaactagt cacaaaaacc ctgactatca cctgatagat tgcttgtgct gcctgataat     60
tactcgcact tttcccaggc tagtgcaaat cttcaggggc cgtccaggac tacagagctg    120
tttcacccta ccttggcttc aatctcttcc cccatgctcg aaggtgcgga gctgtacttc    180
aacgtggacc atggctacct ggagggcctg gttcgaggat gcaaggccag cctcctgacc    240
cagcaagact atatcaacct ggtccagtgt gagaccctag aagacctgaa aattcatctc    300
cagactactg attatggtaa ctttttggct aatcacacaa atcctcttac tgtttccaaa    360
attgacactg agatgaggaa aagactatgt ggagaatttg agtatttccg gaatcattcc    420
ctggagcccc tcagcacatt tctcacctat atgacgtgca gttatatgat agacaatgtg    480
attctgctga tgaatggtgc attgcagaaa aaatctgtga agaaaattct ggggaagtgc    540
caccccttgg gccgtttcac agaaatggaa gctgtcaaca ttgcagagac accttcagat    600
ctctttaatg ccattctgat cgaaacgcca ttagctccat tcttccaaga ctgcatgtct    660
gaaaatgctc tagatgaact gaatattgaa ttgctacgca ataaactata caagtcttac    720
cttgaggcat tctataaatt ctgtaagaat catggtgatg tcacagcaga agttatgtgt    780
cccattcttg agtttgaggc cgacagacgt gcttttatca tcactcttaa ctcccttggc    840
actgaattga gcaaagaaga ccgagagacc ctctatccaa ccttcggcaa actctatcct    900
gaggggttgc ggctgttggc tcaagcagaa gactttgacc agatgaagaa cgtagcggat    960
cattacggag tatacaaacc tttatttgaa gctgtaggtg gcagtggggg aaagacattg   1020
gaggacgtgt tttacgagcg tgaggtacaa atgaatgtgc tggcattcaa cagacagttc   1080
cactacggtg tgttttatgc atatgtaaag ctgaaggaac aggaaattag aaatattgtg   1140
tggatagcag aatgtatttc acagaggcat cgaactaaaa tcaacagtta cattccaatt   1200
ttataaccca agtaaggttc tcaaatgtag aaaattataa atgttaaaag gaagttattg   1260
aagaaaataa aagaaattat gttatattat ctagactaca caaaagtaag ccacactata   1320
tcttcatgag ttgcaaatcc atggaaacac agtaaaccag ccctgaaaca aagcatttcc   1380
ttgttttcag tggtattaga tcttgttttcc acatgtctgt ctcattcttc actgggcctt   1440
acaggttagt tttaattaac tctatggtat ttttcttatt cttgtttgat catgttaaaa   1500
attggaccta ataaaagtat tttattcttg cttttccatg cttctctaca ggtccaaata   1560
ctgaatgtct cctttacttt ttctctttta aattttttttc tagacagggt ctcactctgt   1620
cacctaggct acagtgcagt ggtgtgatca cagctcactg cagcctcgac ttcccaggct   1680
caagtgatcc tcccagctct cagcctccaa agtagctggc actacaagtg taccccccca   1740
cacaaggcta agttttgtat ttttttgtaga gacagggttt caacatatta tccaggctgg   1800
tgtcgaattc ctgggctcca gggatccaca gtcccccttg gcctcccaaa gtgttgggat   1860
tacatgcatg agccactgtg ctgggcttca tttacatttt aactgtctgt tccttgccta   1920
gattcacaga aatccaaagc tgtatgtagt caacatggtt cacaagtgtt ggaaaatgtg   1980
ttttttgttt tgttttgttt tgtttcgttt tgttttgaga cagagtttcc ctctgtcgcc   2040
```

-continued

```
caggctagag tgcaatggcg tgatctcggc tcactgcaac ctccacctcc cagattcaag    2100
caactctctg cctcagcctc ccgagtagct gggattacaa gcacccacca ctacactcag    2160 ctaattttt gtattttag tagagccggg gtttcaccat cttggccagg ctgatcttga      2220
actcctgagc tcatgatcca cccgcctcag cctcccaaag tgctgggatt acaggcccct    2280
tgttcagcca ctgcacctgg cccttatt tgttttgtt ttctaatata ctttgatgta       2340
atcagcttga gaaagcaaca caatttcaaa tcctatcttc tagatgcaag cagtgttaaa    2400
tttgttaata aatttgcttt tcacacctt ctttaaataa aaggtatatc tctctttaaa     2460
aaaaaaaaaa aaaaaaaaaa a                                              2481
```

<210> SEQ ID NO 5
<211> LENGTH: 350
<212> TYPE: PRT
<213> ORGANISM: Mouse

<400> SEQUENCE: 5

```
Met Leu Glu Thr Ala Glu Leu Tyr Phe Asn Val Asp His Gly Tyr Leu
1               5                   10                  15

Glu Gly Leu Val Arg Gly Cys Lys Ala Ser Leu Leu Thr Gln Gln Asp
            20                  25                  30

Tyr Val Asn Leu Val Gln Cys Glu Thr Leu Glu Asp Leu Lys Ile His
        35                  40                  45

Leu Gln Thr Thr Asp Tyr Gly Asn Phe Leu Ala Asn Glu Thr Asn Pro
    50                  55                  60

Leu Thr Val Ser Lys Ile Asp Thr Glu Met Arg Lys Lys Leu Cys Arg
65                  70                  75                  80

Glu Phe Asp Tyr Phe Arg Asn His Ser Leu Glu Pro Leu Ser Thr Phe
                85                  90                  95

Leu Thr Tyr Met Thr Cys Ser Tyr Met Ile Asp Asn Ile Ile Leu Leu
            100                 105                 110

Met Asn Gly Ala Leu Gln Lys Lys Ser Val Lys Glu Val Leu Ala Lys
        115                 120                 125

Cys His Pro Leu Gly Arg Phe Thr Glu Met Glu Ala Val Asn Ile Ala
    130                 135                 140

Glu Thr Pro Ser Asp Leu Phe Lys Ala Val Leu Val Glu Thr Pro Leu
145                 150                 155                 160

Ala Pro Phe Phe Gln Asp Cys Met Ser Glu Asn Thr Leu Asp Glu Leu
                165                 170                 175

Asn Ile Glu Leu Leu Arg Asn Lys Leu Tyr Lys Ser Tyr Leu Glu Ala
            180                 185                 190

Phe Tyr Lys Phe Cys Lys Asp His Gly Asp Val Thr Ala Asp Val Met
        195                 200                 205

Cys Pro Ile Leu Glu Phe Glu Ala Asp Arg Arg Ala Leu Ile Ile Thr
    210                 215                 220

Leu Asn Ser Phe Gly Thr Glu Leu Ser Lys Glu Asp Arg Glu Thr Leu
225                 230                 235                 240

Phe Pro Thr Cys Gly Arg Leu Tyr Pro Glu Gly Leu Arg Leu Leu Ala
                245                 250                 255

Gln Ala Glu Asp Phe Glu Gln Met Lys Arg Val Ala Asp Asn Tyr Gly
            260                 265                 270

Val Tyr Lys Pro Leu Phe Asp Ala Val Gly Gly Ser Gly Gly Lys Thr
        275                 280                 285

Leu Glu Asp Val Phe Tyr Glu Arg Glu Val Gln Met Asn Val Leu Ala
    290                 295                 300
```

```
Phe Asn Arg Gln Phe His Tyr Gly Val Phe Tyr Ala Tyr Val Lys Leu
305                 310                 315                 320

Lys Glu Gln Glu Met Arg Asn Ile Val Trp Ile Ala Glu Cys Ile Ser
            325                 330                 335

Gln Arg His Arg Thr Lys Ile Asn Ser Tyr Ile Pro Ile Leu
        340                 345                 350

<210> SEQ ID NO 6
<211> LENGTH: 350
<212> TYPE: PRT
<213> ORGANISM: Human

<400> SEQUENCE: 6

Met Leu Glu Gly Ala Glu Leu Tyr Phe Asn Val Asp His Gly Tyr Leu
1               5                   10                  15

Glu Gly Leu Val Arg Gly Cys Lys Ala Ser Leu Leu Thr Gln Gln Asp
            20                  25                  30

Tyr Ile Asn Leu Val Gln Cys Glu Thr Leu Glu Asp Leu Lys Ile His
        35                  40                  45

Leu Gln Thr Thr Asp Tyr Gly Asn Phe Leu Ala Asn His Thr Asn Pro
50                  55                  60

Leu Thr Val Ser Lys Ile Asp Thr Glu Met Arg Lys Arg Leu Cys Gly
65                  70                  75                  80

Glu Phe Glu Tyr Phe Arg Asn His Ser Leu Glu Pro Leu Ser Thr Phe
                85                  90                  95

Leu Thr Tyr Met Thr Cys Ser Tyr Met Ile Asp Asn Val Ile Leu Leu
            100                 105                 110

Met Asn Gly Ala Leu Gln Lys Lys Ser Val Lys Glu Ile Leu Gly Lys
        115                 120                 125

Cys His Pro Leu Gly Arg Phe Thr Glu Met Glu Ala Val Asn Ile Ala
130                 135                 140

Glu Thr Pro Ser Asp Leu Phe Asn Ala Ile Leu Ile Glu Thr Pro Leu
145                 150                 155                 160

Ala Pro Phe Phe Gln Asp Cys Met Ser Glu Asn Ala Leu Asp Glu Leu
                165                 170                 175

Asn Ile Glu Leu Leu Arg Asn Lys Leu Tyr Lys Ser Tyr Leu Glu Ala
            180                 185                 190

Phe Tyr Lys Phe Cys Lys Asn His Gly Asp Val Thr Ala Glu Val Met
        195                 200                 205

Cys Pro Ile Leu Glu Phe Glu Ala Asp Arg Arg Ala Phe Ile Ile Thr
210                 215                 220

Leu Asn Ser Phe Gly Thr Glu Leu Ser Lys Glu Asp Arg Glu Thr Leu
225                 230                 235                 240

Tyr Pro Thr Phe Gly Lys Leu Tyr Pro Glu Gly Leu Arg Leu Leu Ala
                245                 250                 255

Gln Ala Glu Asp Phe Asp Gln Met Lys Asn Val Ala Asp His Tyr Gly
            260                 265                 270

Val Tyr Lys Pro Leu Phe Glu Ala Val Gly Gly Ser Gly Gly Lys Thr
        275                 280                 285

Leu Glu Asp Val Phe Tyr Glu Arg Glu Val Gln Met Asn Val Leu Ala
290                 295                 300

Phe Asn Arg Gln Phe His Tyr Gly Val Phe Tyr Ala Tyr Val Lys Leu
305                 310                 315                 320

Lys Glu Gln Glu Ile Arg Asn Ile Val Trp Ile Ala Glu Cys Ile Ser
            325                 330                 335
```

```
Gln Arg His Arg Thr Lys Ile Asn Ser Tyr Ile Pro Ile Leu
        340                 345                 350

<210> SEQ ID NO 7
<211> LENGTH: 17
<212> TYPE: DNA
<213> ORGANISM: Human

<400> SEQUENCE: 7
tatggcaact tcctggc                                                  17

<210> SEQ ID NO 8
<211> LENGTH: 24
<212> TYPE: DNA
<213> ORGANISM: Human

<400> SEQUENCE: 8
gcataaaacg acaccaataa tgga                                          24
```

What is claimed is:

1. An isolated mammalian osteoclast-specific nucleic acid sequence comprising the nucleic acid sequence set forth in SEQ ID NO:2, a functional variant, or a functional fragment thereof, wherein said isolated nucleic acid sequence encodes an amino acid sequence that functions to regulate the formation of large mononuclear cells (MNCs).

2. A vector comprising the isolated nucleic acid sequence of claim 1.

3. A host cell comprising the vector of claim 2.

4. The vector of claim 2, wherein the vector is a plasmid, cosmid, yeast artificial chromosome (YAC), BAC, adenovirus, lentivirus, adeno-associated virus, retrovirus, P1, bacteriophage or eukaryotic viral DNA.

5. The isolated nucleic acid sequence of claim 1, wherein the nucleic acid sequence comprises a nucleic acid sequence having about 85 to about 99% sequence similarity with the nucleic acid coding sequence of SEQ ID NO. 2.

6. An isolated nucleic acid sequence set forth in SEQ ID NO: 2 or an isolated nucleic acid sequence that is at least 85% identical to SEQ ID NO: 2, wherein said nucleic acid sequence encodes an amino acid sequence that functions to regulate the formation of large mononuclear cells (MNCs).

7. A vector comprising the isolated nucleic acid sequence of claim 6.

8. A host cell comprising the vector of claim 7.

* * * * *